United States Patent
Mueller et al.

(10) Patent No.: US 6,747,149 B2
(45) Date of Patent: Jun. 8, 2004

(54) GLUCAMINE SALTS FOR TREATING HEPATITIS VIRUS INFECTIONS

(75) Inventors: Richard A. Mueller, Glencoe, IL (US); Martin L. Bryant, Carisle, MA (US); Richard A. Partis, Evanston, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 10/322,045

(22) Filed: Dec. 17, 2002

(65) Prior Publication Data

US 2003/0195229 A1 Oct. 16, 2003

Related U.S. Application Data

(63) Continuation of application No. 09/503,865, filed on Feb. 14, 2000, now Pat. No. 6,515,028.
(60) Provisional application No. 60/119,858, filed on Feb. 12, 1999, and provisional application No. 60/119,836, filed on Feb. 12, 1999.

(51) Int. Cl.$^7$ .................. C07D 295/22; C07D 409/00; C07D 211/70
(52) U.S. Cl. .................. 544/162; 546/334; 549/13; 564/305; 564/428; 564/440; 564/442; 564/443; 564/454; 564/462; 564/501; 564/502; 564/503; 564/504; 564/505
(58) Field of Search .................. 549/13; 544/162; 546/334; 564/305, 440, 442, 443, 454, 428, 501, 502, 503, 504, 505, 462

(56) References Cited

U.S. PATENT DOCUMENTS

| | | |
|---|---|---|
| 3,590,028 A | 6/1971 | Arcamone et al. |
| 4,012,448 A | 3/1977 | Smith et al. |
| 4,065,562 A | 12/1977 | Ohata et al. |
| 4,182,767 A | 1/1980 | Murai et al. |
| 4,260,622 A | 4/1981 | Junge et al. |
| 4,269,857 A | 5/1981 | Tokuda et al. |
| 4,327,725 A | 5/1982 | Cortese et al. |
| 4,524,060 A | 6/1985 | Mughal et al. |
| 4,533,668 A | 8/1985 | Matsumura et al. |
| 4,611,058 A | 9/1986 | Koebernick |
| 4,612,008 A | 9/1986 | Wong et al. |
| 4,639,436 A | 1/1987 | Junge et al. |
| 4,765,989 A | 8/1988 | Wong et al. |
| 4,783,337 A | 11/1988 | Wong et al. |
| 4,806,650 A | 2/1989 | Schröder et al. |
| 4,849,430 A | 7/1989 | Fleet et al. |
| 4,880,830 A | 11/1989 | Rhodes |
| 4,940,705 A | 7/1990 | Böshagen et al. |
| 4,957,926 A | 9/1990 | Jacob et al. |
| 5,003,072 A | 3/1991 | Partis et al. |
| 5,011,829 A | 4/1991 | Hirsch et al. |
| 5,030,638 A | 7/1991 | Partis et al. |
| 5,041,441 A | 8/1991 | Radin et al. |
| 5,051,407 A | 9/1991 | Böshagen et al. |
| 5,068,112 A | 11/1991 | Samejima et al. |
| 5,144,037 A | 9/1992 | Partis et al. |
| 5,151,519 A | 9/1992 | Behling et al. |
| 5,190,765 A | 3/1993 | Jao et al. |
| 5,221,746 A | 6/1993 | Partis et al. |
| 5,264,356 A | 11/1993 | Rohrschneider |
| 5,281,724 A | 1/1994 | Behling et al. |
| 5,310,745 A | 5/1994 | Partis et al. |
| 5,331,096 A | 7/1994 | Koszyk et al. |
| 5,411,970 A | 5/1995 | Partis et al. |
| 5,451,679 A | 9/1995 | Barta et al. |
| 5,472,969 A | 12/1995 | Platt et al. |
| 5,491,135 A | 2/1996 | Blough |
| 5,525,616 A | 6/1996 | Platt et al. |
| 5,536,732 A | 7/1996 | Lesur et al. |
| 5,595,981 A | 1/1997 | Barta et al. |
| 5,612,480 A | 3/1997 | Barta et al. |
| 5,622,972 A | 4/1997 | Bryant et al. |
| 5,663,342 A | 9/1997 | Barta et al. |
| 5,703,058 A | 12/1997 | Schinazi et al. |
| 6,093,702 A | 7/2000 | Malley et al. |

FOREIGN PATENT DOCUMENTS

| | | |
|---|---|---|
| DE | 4307883 A1 | 9/1993 |
| EP | 0 324 328 A2 | 7/1989 |
| EP | 0 350 012 A2 | 1/1990 |
| EP | 0 367 748 A2 | 5/1990 |
| EP | 0 401 194 A1 | 12/1990 |
| EP | 0 449 026 A2 | 10/1991 |
| EP | 0 477 160 B1 | 3/1992 |
| EP | 0 494 850 A2 | 7/1992 |
| EP | 0 566 556 A1 | 10/1993 |
| EP | 0 691 327 A1 | 1/1996 |
| EP | 0 729 747 A1 | 9/1996 |
| FR | 2700267 A1 | 7/1994 |
| GB | 2020278 | 11/1979 |
| WO | WO 87/03903 A1 | 7/1987 |
| WO | WO 91/03242 A1 | 3/1991 |
| WO | WO 91/17145 A1 | 11/1991 |
| WO | WO 93/18763 A1 | 9/1993 |
| WO | WO 94/04546 A1 | 3/1994 |
| WO | WO 95/06061 A1 | 3/1995 |
| WO | WO 95/19172 A1 | 7/1995 |
| WO | WO 95/22975 A1 | 8/1995 |
| WO | WO 96/40110 A1 | 12/1996 |
| WO | WO 97/00881 A1 | 1/1997 |
| WO | WO 98/35685 A1 | 8/1998 |
| WO | WO 99/29321 A1 | 6/1999 |
| WO | WO 99/40916 A1 | 8/1999 |
| WO | WO 00/47198 A2 | 8/2000 |

OTHER PUBLICATIONS

Abe et al., "Improved Inhibitors of Glucosylceramide Synthase," J. Biochem., 1992, pp. 191–196, vol. 111.

(List continued on next page.)

*Primary Examiner*—Amelia Owens
(74) *Attorney, Agent, or Firm*—Senniger, Powers, Leavitt & Roedel; J. Timothy Keane; Scott J. Meyer

(57) ABSTRACT

N-Substituted glucamine compounds of formula I are effective in treatment of hepatitis infections, including hepatitis B and hepatitis C. In treating hepatitis infections the compounds of formular I may be used alone, or in combinatioin with another antiviral agent selected from among nucleosides, nucleotides, immunomodulators, immunostimulants or various combination of such other agents.

13 Claims, 3 Drawing Sheets

OTHER PUBLICATIONS

Abe et al., "Structural and Stereochemical Studies of Potent Inhibitors of Glucosylceramide Synthase and Tumor Cell Growth," Journal of Lipid Research, 1995, pp. 611–621, vol. 36.

Abe et al., "Induction of Glycosylceramide Synthase by Synthase Inhibitors and Ceramide," Biochemica et Biophysica Acta, 1996, pp. 333–341, vol. 1299.

Acosta et al., "Agents for Treating Human Immunodeficiency Virus Infection," Am. J. Hosp. Pharm., vol. 51, Sep. 15, 1994, pp. 2251–2287.

Ardalan et al., "Mechanism of Action of a New Antitumor Agent, Carbetimer," Cancer Research, 1986, pp. 5473–5476, vol. 46.

Arends, "Recueil des Travaux Chimiques des Pays–Bas," Journal of the Royal Netherlands Chemical Society, Feb. 1994, Recl. Trav. Chim. Pays–Bas 113, 63–114, contents page only.

Beketic–Oreskovic et al., "Decreased Mutation Rate for Cellular Resistance to Doxorubicin and Suppression of mdr1 Gene Activation by the Cyclosporin PSC 833," Journal of the National Cancer Institute, 1995, pp. 1593–1602, vol. 87, No. 21.

Block et al., "The Secretion of Human Hepatitis B Virus is Inhibited by the Imino Sugar, N–Butyl–Deoxynojirimycin," undated, Jefferson Cancer Institute, et al., No. 81, one page.

Block et al., "Treatment of Chronic Hepadnavirus Infection in a Woodchuck Animal Model with an Inhibitor of Protein Folding and Trafficking," May 1998, Nature Medicine, vol. 4, No. 5, pp. 610–614.

Block et al., "Secretion of Human Hepatitis B Virus is Inhibited by the Imino Sugar N–butyldeoxynojirimycin," Mar. 1994, Proc. Natl. Acad. Sci., vol. 91, pp. 2235–2239.

Blum et al., "Antiviral Therapy of Hepatitis B Virus Infection: Blocking Viral Gene Expression," Elsevier Science, B.V., Advanced Drug Delivery Reviews, 1995, pp. 321–331, vol. 17.

Bolhuis et al., "Mechanisms of Multidrug Transporters," 1997, FEMS Microbiology Reviews, vol. 21, pp. 55–84.

Bradley et al., "Mechanism of Multidrug Resistance," 1988, Biochimica et Biophysica Acta, vol. 948, pp. 87–128.

Bradley et al., "P–glycoprotein, Multidrug Resistance and Tumor Progression," 1994, Cancer and Metastasis Reviews, vol. 13, pp. 223–233.

Bruyneel et al. "Effect of Glycosylation Inhibitors on N–Glycosylpeptides and on Invasion of Malignant Mouse $MO_4$ Cells in Vitro," Journal of Cell Science, vol. 95, 1990, pp. 279–286.

Cabot et al., "Tamoxifen Retards Glycosphingolipid Metabolism in Human Cancer Cells," FEBS Letters, 1996, pp. 129–131, vol. 394.

Carbohydrate Chemistry, "Chapter 20: Nucleosides," undated, pp. 242–276.

Chabner et al., "Reversal of Multidrug Resistance," Jan. 1991, Journal of Clinical Oncology, vol. 9, No. 1, pp. 4–6.

Coates et al., "Developments in Viral Hepatitis During 1994," Exp. Opin. Ther. Patents, 1995, pp. 747–756, vol. 5, No. 8.

Dalton et al., "A Phase III Randomized Study of Oral Verapamil as a Chemosensitizer to Reverse Drug Resistance in Patients with Refractory Myeloma," Cancer, 1995, pp. 815–820, vol. 75, No. 3.

Dicato et al., "Multidrug Resistance: Molecular and Clinical Aspects," Cytokines, Cellular & Molecular Therapy, 1997, pp. 91–100, vol. 3, No. 2.

Dienstag et al., "A Preliminary Trial of Lamivudine for Chronic Hepatitis B Infection," The New England Journal of Medicine, 1995, pp. 1657–1661, vol. 333, No. 25.

Doige et al., "The Effects of Lipids and Detergents on ATPase–Active P–Glycoprotein," 1993, Biochimica et Biophysica Acta, vol. 1146, pp. 65–72.

Doong et al., "Inhibition of the Replication of Hepatitis B Virus In Vitro by 2',3'–dideoxy–3'–thiacytidine and Related Analogues," Oct. 1991, Proc. Natl. Acad. Sci., vol. 88, pp. 8495–8499.

Dusheiko, "Treatment and Prevention of Chronic Viral Hepatitis," 1995, Pharmac. Ther., vol. 65, pp. 47–73.

Dwek, R., "Glycobiology: Toward Understanding the Function of Sugars," Chem. Rev. 1996, 96, pp. 683–720.

Elbein, "Inhibitors of the Biosynthesis and Processing of N–Linked Oligosaccharide Chains," 1987, Ann. Rev. Biochem., 56:497–534.

Fischl et al., "The Preliminary Efficacy and Safety of N–Butyl–Deoxynojirimycin (SC–48334), an alpha–Glucosidase I Inhibitor, in Combination with Zidovudine (ZDA)," International Conference on AIDS, Berlin, Jun. 6–11, 1993, one page.

Fischl et al., "The Safety and Efficacy of Combination N–Butyl–Deoxynojirimycin (SC–48334) and Zidovudine in Patients with HIV–1 Infection and 20–500 CD4 Cells/$mm^3$," 1994, Journal of Acquired Immune Deficiency Syndromes, vol. 7, pp. 139–147.

Fisher et al., "Clinical Studies with Modulators of Multidrug Resitance," Drug Resistance in Clinical Oncology and Hematology, 1995, pp. 363–382, vol. 9, No. 2.

Fiume et al., "Targeting of Antiviral Drugs to the Liver Using Glycoprotein Carriers," Advanced Drug Delivery Reviews, vol. 14, 1994, pp. 51–65.

Fleet et al., "Inhibition of HIV Replication by Amino–Sugar Derivatives," Sep. 1988, Federation of European Biochemical Societies, vol. 237, No. 1,2, pp. 128–132.

Gasparini et al., "Clinical Importance of the Determination of Tumor Angiogenesis in Breast Carcinoma: Much More Than a New Prognostic Tool," Journal of Clinical Oncology, vol. 13, No. 3, Mar. 1995, pp. 765–782.

Gish et al., "Recent Developments in the Treatment of Chronic Hepatitis B Virus Infection," 1995, Exp. Opin. Invest. Drugs, 4(2), pp. 95–115.

Goss et al., "Inhibitors of Carbohydrate Processing: A New Class of Anticancer Agents," Clinical Cancer Research, vol. 1, Sep. 1995, pp. 935–944.

Hardman et al., "Goodman & Gilman's The Pharmacological Basis of Therapeutics," 1996, McGraw–Hell, Ninth Edition, Chapter 32: Drugs Used for the Treatment of Myocardial Ischemica, Verepemil, pp. 767–774, 780–781, 799–801, and 829.

Holleran et al., "Characterization of Cellular Lipids in Doxorubicin–Sensitive and –Resistnat P388 Mouse Leukemia Cells," 1986, Cancer Chemother Pharmaocl, 17:11–15.

Hollinger, "Hepatitis B Virus," Field Virology, Third Edition, Chapter 86, pp. 2739–2807.

Hui et al., "Reduced $p21^{WAF1/CIP1}$ Expression and p53 Mutation in Hepatocellular Carcinomas," Mar. 1997, Hepatology, vol. 25, No. 3, pp. 575–579.

Hoofnagel et al., "The Treatment of Chronic Viral Hepatitis," Drug Therapy, vol. 336, No. 5, pp. 347–356.

Iino, "Treatment of Chronic Viral Hepatitis," Mol. Med. (Tokyo), 1996, vol. 33, No. 3, pp. 276–286 (English language abstract only).

Inokuchi et al., "Antitumor Activity Via Inhibition of Glycosphingolipid Biosynthesis," 1987, Cancer Letters, vol. 38, pp. 23–30.

Inokuchi et al., "Stimulation of Glycosphingolipid Biosynthesis by L–threo–1–Phenyl–2–Decanoylamino–1–Propanal and Its Homologs in B16 Melanoma Cells," 1995, J. Biochem., vol. 117, No. 4, pp. 766–773.

Isom et al., "Molecular Pathology of Human Oncogenic Viruses," Cellular and Molecular Pathogenesis, Chapter 14, 1996, pp. 341–387.

Jacob et al., "Aminosugar Attenuation of HIV Infection," 1992, Natural Products as Antiviral Agents, pp. 137–152.

Jacob et al., "Iminosugar alpha–Glucosidase Inhibitors as Drugs and Pro–Drugs for Treatment of HIV Infections," Washington Book of Abstracts, 208th ACS National Meeting, Aug. 21–25, 1994, one page.

Jacob, "Glycosylation Inhibitors in Biology and Medicine," Current Opinion in Structural Biology, No. 5, 1995, pp. 605–611.

Jezowska–Bojczuk et al., "Copper(II) Interactions with an Experimental Antiviral Agent, 1–Deoxynojirimycin, and Oxygen Activation by Resulting Complexes," 1996, Journal of Inorganic Biochemistry, vol. 64, pp. 231–246.

Jones et al., "Use of the Topliss Scheme for the Design of More Effective Chelating Agents for Cadmium Decorporation," Chem. Res. Toxicol., vol. 1, 1988, pp. 234–237.

Karpas et al., "Aminosugar Derivatives as Potential Anti-Human Immunodeficiency Virus Agents," Dec. 1988, Proc. Natl. Acad. Sci., vol. 85, pp. 9229–9233.

Karrer et al., "Zur Kenntis der Reduktionsprodukte aus Aromatischen Aminen und Zuckern," 1935, p. 1338–1340.

Kawakami et al., "Monoclonal Antibodies with Affinity to Self–Complementary Left–Handed DNA Containing Cyclonucleosides with High Anti Conformation," 1994, Nucleosides & Nucleotides, vol. 13(1–3), pp. 421–427.

Kers et al., "Nucleoside Phosphonates. Development of Synthetic Methods and Reagents," 1996, Nucleosides & Nucleotides, 15(1–3), pp. 361–378.

Korba B., "In Vitro Evaluation of Combination Therapies Against Hepatitis B Virus Replication," 1995, Antiviral Research, vol. 29, pp. 49–51.

Korba et al., "Antiviral Effectiveness of 3TC, Famciclovir, and Interferon Against Chronic WHV Replication–Potential for Combination Therapy," 1996, Molecular Biology of Hepatitis B Viruses Meeting, p. 201.

Korba et al., "Effectiveness of Combination Therapies with 3TC, Famiciclovir, and Alpha Interferon Against Woodchuck Hepatitis Virus Replication in Chronically–infected Woodchucks: Model for Potential Anti–HBV Treatments," Apr. 1997, Antiviral Research, vol. 34, No. 2, p. A52.

Lavie et al., "Agents that Reverse Multidrug Resistance, Tamoxifen Verapamil, and Cyclosporin A, Block Glycosphingolipid Metabolism by Inhibiting Ceramide Glycosylation in Human Cancer Cells," Aug. 20, 1996, The Journal of Biological Chemistry, vol. 272, No. 3, pp. 1682–1687.

Lavie et al., "Accumulation of Glucosylceramides in Multidrug–Resistant Cancer Cells," Aug. 9, 1996, The Journal of Biological Chemistry, Vo. 271, No. 32, pp. 19530–19536.

Legler et al., "Glycosylceramidase from Calf Spleen: Characterization of its Active Site with 4–n–Alkylurnbelliferyl β–glucoside and N–alkyl Derivatives of 1–Deoxynojirimycin," Dec. 1985, Bio–ChemHoppe–Seyler, vol. 366, pp. 1113–1122.

Locarnini et al., "Hepatitis B: New Approaches for Antiviral Chemotherapy," 1996 Antiviral Chemistry & Chemotherapy, 7(2), pp. 53–64.

Lu et al., "Evidence That N–Linked Glycosylation is Necessary for Hepatitis B Virus Secretion," Nov. 10, 1995, Virology, vol. 213, No. 2, pp. 660–665.

Lu et al., "Aberrant Trafficking of Hepatitis B Virus Glycoproteins in Cells in Which N–glycan Processing is Inhibited," Mar. 1997, Proc. Natl. Acad. Sci., vol. 94, pp. 2380–2385.

May et al., "Plasma Membrane Lipid Composition of Vinblastine Sensitive and Resistant Human Leukaemic Lymphoblasts," 1988, Int. J. Cancer, vol. 42, pp. 728–733.

Mehta et al., Hepatitis B Virus (HBV) Envelope Glycoproteins Vary Drastically in Their Sensitivity to Glycan Processing: Evidence that Alteration of a Single N–Linked Glycosylation Site Can Regulate HBV Secretion, Mar. 1997, Proc. Natl. Acad. Sci., vol. 94, pp. 1822–1827.

Mitts et al., "The Reaction of Glucose with Some Amines," Journal of the American Chemical Society, vol. 66, Mar. 1944, pp. 483–486.

Mueller, R., et al., Chem. Abst. 135:175348.

Mülder et al., "Multidrug Resistance–Modifiying Components in Human Plasma with Potential Clinical Significance," Jan. 1996, Journal of Experimental Therapeutics & Oncology, vol. 1, No. 1 pp. 13–22.

Mutchnick et al., "Thymosin Treatment of Chronic Active Hepatitis B (CAHB): A Preliminary Report on a Controlled, Double Blind Study," 1988, Hepatology, vol. 8, No. 5, Article 208, p. 1270.

Mutchnick et al., "Thymosin Treatment of Chronic Active Hepatitis B (CAHB): Results of a Pilot Study," Hepatology, vol. 10, No. 4, 1989.

Mutchnick et al., "Thymosin Treatment of Chronic Hepatitis B: A Placebo–controlled Pilot Trial," 1991, Hepatology, vol. 14, No. 3, pp. 409–415.

Mutchnick et al., "Prospectives on the Treatment of Chronic Hepatitis B and Chronic Hepatitis C with Thymic Peptides and Antiviral Agents," 1994, Antiviral Research, vol. 24, pp. 245–257.

Mutchnick et al., "Thymosin $\alpha_1$ Treatment of Chronic Hepatitis B: A Multicenter, Randomized, Placebo–Controlled Double Blind Study," Apr. 1995, AASLD, A1127, one page.

Myers, "New Antiretroviral Agents in the Clinic," Reviews of Infectious Diseases, vol. 12, No. 5, Sep./Oct. 1990, pp. 944–950.

Newbrun et al., "Inhibition by Acarbose, Nojirimycin and 1–Deoxynojirimycin of Glucosyltransferase Produced by Oral Stroptococci," 1983, Archs Oral Biol., vol. 28, No. 6, pp. 531–536.

Ogawa et al., "Synthesis of Potent β–D–Glucocerebrosidase Inhibitors: N–Alkyl–β–Valienamines," 1996, Bioorganic & Medicinal Chemistry Letters, vol. 6, No. 8, pp. 929–932.

Platt et al., "Modulation of Cell–Surface Transferrin Receptor by the Imino Sugar N–butyldeoxynojirimycin,"1992, Eur. J. Biochem., vol. 208, pp. 187–193.

Platt et al., "N–Butyldeoxynojirimycin is a Novel Inhibitors of Glycolipid Biosynthesis: Secretion of Human Hepatitis B Virus Is Inhibited by the Imino Sugar N–Butyldeoxynojirimycin," 1994, Chemtracts–Organic Chemistry, vol. 7, pp. 106–107.

Platt et al., "N–Butyldeoxynojirimycin Is a Novel Inhibitor of Glycolipid Biosynthesis," Mar. 18, 1994, The Journal of Biological Chemistry, vol. 269, No. 11, pp. 8362–8364.

Platt et al., "N–Butyldeoxygalactonojirimycin Inhibits Glycolipid Biosynthesis but Does Not Affect N–Linked Oligosaccharide Processing," Oct. 28, 1994, The Journal of Biological Chemistry, vol. 269, No. 43, pp. 27108–27114.

Platt et al., "Inhibitors of Glycosphingolipid Biosynthesis," Trends in Glycoscience and Glycotechnology, vol. 7, No. 38, Nov. 1995, pp. 495–511.

Platt et al., "New Approach for the Treatment of Guachers Disease," Mar. 1996, Gauchers Association Newsletter, one page.

Platt et al., "Prevention of Lysosomal Storage in Tay–Sachs Mice Treated with N–Butyldeoxynojirimycin," Apr. 18, 1997, Science, vol. 276, pp. 428–431.

Prence et al., "In Vitro Accumulation of Glucocerebroside in Neuroblastoma Cells: A Model for Study of Gaucher Disease Pathobiology," 1996, Journal of Neuroscience Research, 43:365–371.

Raderer et al., "Clinical Trials of Agents that Reverse Multidrug Resistance," Dec. 15, 1993, Cancer, vol. 72, No. 12, pp. 3553–3563.

Radin et al., "Inhibitors of Cerebroside Metabolism," 1981, Methods in Enzymology, vol. 72, pp. 673–684.

Radin, "Rationales for Cancer Chemotherapy with PDMP, a Specific Inhibitor of Glucosylceramide Synthase," 1994, Molecular and Chemical Neuropathology, vol. 21, pp. 111–127.

Radin et al., "Treatment of Gaucher Disease with an Enzyme Inhibitor," 1996, Glycoconjugate Journal, vol. 13, pp. 153–157.

Ramu et al., "Differences in Lipid Composition of Doxorubicin–Sensitive and –Resitant P388 Cells," Apr. 1984, Cancer Treatment Reports, vol. 68, No. 4, pp. 637–641.

Ratner et al., "Mechanism of Action of N–Butyl Deoxynojirimycin in Inhibiting HIV–1 Infection and Activity in Combination with Nucleoside Analogs," AIDS Research and Human Retroviruses, vol. 9, No. 4, 1993, pp. 291–297.

Repp et al., "The Effects of Processing Inhibitors of N–Linked Oligosaccharides on the Intracellular Migration of Glycoprotein E2 of Mouse Hepatitis Virus and the Maturation of Coronavirus Particles," Dec. 15, 1986, The Journal of Biological Chemistry, vol. 260, No. 29, pp. 15873–15879.

Rhodes "Therapeutic Potential of Schiff Base–forming Drugs," 1996, Exp. Opin. Invest. Drugs, 5(3), pp. 257–268.

Ries et al., "Treatment of Advanced and Refractory Breast Cancer with Doxorubicin, Vincristine and Continuous Infusion of Verapamil. A Phase I–II Clinical Trial," 1991, Med. Oncol. & Tumor Pharmacother, vol. 8, No. 1, pp. 39–43.

Rosina et al., "Recent Developments in the Treatment of Hepatits D Infection," 1996, Anti–infectives—Section Review, Exp. Opin. Invest. Drugs, No. 5(2), pp. 197–205.

Rusconi et al., "Inhibition of Human Immunodeficiency Virus Type I Replication in Cytokine–Stimulated Monocytes/Macrophages by Combination Therapy," Journal of Infectious Diseases, vol. 170, 1994, pp. 1361–1366.

Sachs, "Antiretroviral Chemotherapy of Human Immunodeficiency Virus Infections Other Than with Azidothymidine," Arch. Inter. Med., vol. 152, Mar. 1992, pp. 485–501.

Saunier et al., "Inhibition of N–Linked Complex Oligosaccharide Formation by 1–Deoxynojirimycin, An Inhibitor of Processing Glucosidases," Dec. 10, 1982, The Journal of Biological Chemistry, vol. 257, No. 2, pp. 14155–14161.

Senuma et al., "Highly Effective Resolution of 1,3–Dibensl–6–hydroxy–3,3a,6,6a–tetrahydro–1H–furo[3,4–d]imidazole–2,4–dione, and Intermediate for Biotin, with Optically Active Amines and Reutilization of the Unwanted Epimer," Chem. Pharm. Bull., vol. 38, No. 4, 1990, pp. 882–887.

Shukla et al., "Rapid Kidney Changes Resulting from Glycosphingolipid Depletion by Treatment with a Glycosyltransferase Inhibitor," 1991, Biochemica et Biophysca Acta., vol. 1083, pp. 101–108.

Simon et al., "Treatment of Chronic Hepatits C with Interferon Alfa–n3: A Multicenter, Randomized, Open–Label Trial," Feb. 1997, Hepatology, vol. 25, No. 2, pp. 445–448.

Sobrero et al., "Sequential Dichloromethotrexate (DCM) and 5–Fluorouracil (FU): A Synergistic Combination Potentially Valuable for Hepatic Artery Infusion Therapy," Mar. 1983, ASCO Abstracts, Clinical Pharmacology, vol. 2, Article C–102, p. 26.

Tan et al., "Chemical Modification of the Glucosidase Inhibitor 1–Deoxynojirimycin," Aug. 5, 1991, The Journal of Biological Chemistry, Vo. 266, No. 22, pp. 14504–14510.

Tan et al., "Introduction of Oxygen into the Alkyl Chain of N–decyl–dNM Decreases Lipophilicity and Results in Increased Retention of Glucose Residues on N–Linked Oligosaccharides," 1994, Glycobiology, vol. 4, No. 2, pp. 141–149.

Tennant et al., "Animal Models in the Preclinical Assessment of Therapy for Viral Hepatitis," Antiviral Therapy, vol. 1, (Suppl. 4), 1996, pp. 47–52.

Tsuruo et al., "Overcoming of Vincristine Resistance in P388 Leukemis In Vivo and In Vitro Enhanced Cytotoxitity of Vincristine and Vinblastine by Verapamil," May 1981, Cancer Research, vol. 41, pp. 1967–1972.

van den Broek et al., "Synthesis of Oxygen–Substitited N–alkyl 1–deoxynojirimycin derivatives: asa sugar α–glucosidase inhibitors showing antiviral (HIV–1) and immunosuppressive activity," Recl. Trav. Chim. Pays–Bas 113, 1994, pp. 507–516.

Volm et al., "Expression of Resistance Factors (P–Glycoprotein, Glutathione S–Transferase–II, and Topoisomerase II) and Their Interrelationship to Proto–Oncogene Products in Renal Cell Carcinomas," Jun. 15, 1993, Cancer, vol. 71, No. 12, pp. 3981–3987.

Vorbrüggen et al., "Some Recent Trends and Progress in Nucleoside Synthesis," 1996, Acta Biochimica Polonica, vol. 43, No. 1, pp. 25–36.

Wadkins et al., "The Role of Drug–Lipid Interactions in the Biological Activity of Modulators of Multi–Drug Resistance," 1993, Biochimica et Biophysica Acta, vol. 1153, pp. 225–236.

Wang et al., "Chemo–enzymatic Synthesis of Five–membered Azasugars as Inhibitors of Fucosidase and Fucosyltransferase: An Issue Regarding The Stereochemistry Discrimination at Transition States," 1993, Tetrahedron Letters, vol. 34, No. 3, pp. 403–406.

Welsh et al., "Accumulation of Fatty Alcohol in MCF–7 Breast Cancer Cells," Nov. 15, 1994, Archives of Biochemistry and Biophysics, vol. 315, No. 1, pp. 41–47.

Wilson et al., "Nitrogen Glycosylation Reactions Involving Pyrimidine and Purine Nucleoside Bases with Furanoside Sugars," Dec. 1995, Synthesis, Department of Chemistry, Emory University, pp. 1465–1479.

Wiltnik, "Future Prospects in Antiviral Therapy," Jun. 1992, Pharmaceutisch Weekblad Scientific Edition, 14(4A), pp. 268–274.

Wishart et al., "Quinidine as Resistance Modulator of Epirubicin in Advanced Breast Cancer: Mature Results of a Placebo–Controlled Randomzied Trial," Sep. 1994, Journal of Clinical Oncology, vol. 12, No. 9, pp. 1771–1777.

Wright et al., "Phospholipid and Ether Linked Phospholipid Content Alter with Cellular Resistance to Vinblastine," Dec. 17, 1985, Biochemical and Biophysical Research Communications, vol. 133, No. 2, pp. 539–545.

Yangco et al., "Pilot Safety and Efficacy of Combination SC–48334 (N–Butyl–Deoxynojirimycin (NB–DNJ) and Zidovudine (ZDA) in Symptomatic HIV–1 Infected Patients with $\geq 200-\leq 500$ CD4 Cells/mm$^3$," Abstracts of the 1st National Conference on Human Retroviruses, Session 86, Abstract No. 574, p. 160.

Zitzmann et al., "Imino Sugars Inhibit the Formation and Secretion of Bovine Viral Diarrhea Virus, a Pestivirus Model of Hepatitis C Virus: Implications for the Development of Broad Spectrum Anti–Hepatitis Virus Agents," PNAS, vol. 96, No. 21, Oct. 12, 1999, pp. 11878–11882.

GLUCAMINE SALTS FOR TREATING HEPATITIS VIRUS INFECTIONS

RELATED APPLICATION INFORMATION

This application is a continuation of Ser. No. 09/503,865, filed Feb. 14, 2000 now U.S. Pat. No. 6,515,028, which claims from Ser. No. 60/119,858, filed Feb. 12, 1999 and from Ser. No. 60/119,836, filed Feb. 12, 1999.

BACKGROUND OF THE INVENTION

1. Field of Invention

The present invention relates to methods and compositions for treating hepatitis virus infections, especially hepatitis B virus infections, in mammals, especially humans. The methods comprise administering glucamine compounds in combination with nucleoside antiviral agents, nucleotide antiviral agents, mixtures thereof, or immunomodulating/-immunostimulating agents. Such combinations of anti-hepatitis viral agents show unexpected efficacy in inhibiting replication and secretion of hepatitis viruses in cells of mammals infected with these viruses.

2. Background of Invention

Over half the biologically important proteins are glycosylated and that glycosylation may vary with disease. Based upon this information, the use of drugs to control of glycosylation patterns, glycoforms, changes or rates of change will have a biochemical effect and may provide a beneficial therapeutic result. Control of glycolipid and glycoprotein sugar patterns as well as their synthesis and degradation leads to basic physiological effects on mammals including humans, agricultural animals and pets. Possibly, this is through influences on, for example, N-linked glycans, O-linked glycans, glucosoaminoglycans, glycosphingolipids, glycophospholipids, lectins, immuneoglobulin molecules, antibodies, glycoproteins and their biochemical intermediates or conversion products. Modification of glycosalation site occupancy influences receptor and enzyme binding site specificity, selectivity, capacity, protein folding, enzyme activity, kinetics and energetics. Glycosidase and glycosyltransferase systems are two biochemical mechanisms that are suggested to affect such systems (Dwek, Raymond A., Glycobiology: Toward Understanding the Function of Sugars, Chemical Reviews, 96, 683–720 (1996).

Iminosugars are anti-viral drugs that can induce the inhibition of viral interactions with and within mammalian cells such as attachment to cells, penetration of cells, maturation within cells and release from cells. The mechanism involved may be glucosidase inhibition, glycosyl transferase inhibition or others as discussed above.

Hepatitis B Virus (HBV, HepB) is a causative agent of acute and chronic liver disease including liver fibrosis, cirrhosis, inflammatory liver disease, and hepatic cancer that can lead to death in some patients (Joklik, Wolfgang K., Virology, Third Edition, Appleton & Lange, Norwalk, Conn., 1988 (ISBN 0-8385-9462-X)). Although effective vaccines are available, there are still more than 300 million people worldwide, i.e., 5% of the world's population, chronically infected with the virus (Locarnini, S. A., et. al., Antiviral Chemistry & Chemotherapy (1996) 7(2) :53–64). Such vaccines have no therapeutic value for those already infected with the virus. In Europe and North America, between 0.1% to 1% of the population is infected. Estimates are that 15% to 20% of individuals who acquire the infection develop cirrhosis or another chronic disability from HBV infection. Once liver cirrhosis is established, morbidity and mortality are substantial, with about a 5-year patient survival period (Blume, H., E., et.al., Advanced Drug Delivery Reviews (1995) 17:321–331). It is therefore necessary and of high priority to find improved and effective anti-hepatitis therapies (Locarnini, S. A., et. al., Antiviral Chemistry & Chemotherapy (1996) 7(2): 53–64)

Other hepatitis viruses significant as agents of human disease include Hepatitis A, Hepatitis B, Hepatitis C, Hepatitis Delta, Hepatitis E, Hepatitis F, and Hepatitis G (Coates, J. A. V., et.al., Exp. Opin. Ther. Patents (1995) 5(8):747–756). Hepatitis C infection is also on the increase and effective treatments are needed. In addition, there are animal hepatitis viruses that are species-specific. These include, for example, those infecting ducks, woodchucks, cattle and mice.

Glucamine Compounds

Glucamine (also known as 1-deoxynojirimycin, DNJ) and its N-alkyl derivatives (together, "imino sugars") are known inhibitors of the N-linked oligosaccharide processing enzymes alpha glucosidase I and II (Saunier et al., J. Biol. Chem. (1982) 257:14155–14161 (1982); Elbein, Ann. Rev. Biochem. (1987) 56:497–534). As glucose analogs, they also have potential to inhibit glucose transport, glucosyltransferases, and/or glycolipid synthesis (Newbrun et al., Arch. Oral Biol. (1983) 28: 516–536; Wang et al., Tetrahedron Lett. (1993) 34:403–406). Their inhibitory activity against glucosidases has led to the development of these compounds as anti-hyperglycemic agents and antiviral agents. See, for example, PCT International Publication WO 87/03903 and U.S. Pat. Nos. 4,065,562; 4,182,767; 4,533,668; 4,639,436; 4,849,430; 4,957,926; 5,011,829; and 5,030,638.

Glucosidase inhibitors such as N-alkyl-glucamine compounds wherein the alkyl group contains between three and six carbon atoms have been shown to be effective in the treatment of Hepatitis B infection (PCT International Publication WO 95/19172). For example, N-(n-butyl)-deoxynojirimycin (N-butyl-DNJ; N-(n-butyl)-1-5-dideoxy-1,5-imino-D-glucitol) is effective for this purpose (Block, T. M., Proc. Natl. Acad. Sci. USA (1994) 91:2235–2239; Ganem, B. Chemtracts: Organic Chemistry (1994) 7(2), 106–107). N-butyl-DNJ has also been tested as an anti-HIV-1 agent in HIV infected patients, and is known to be well tolerated. Another alpha glucosidase inhibitor, deoxynojirimycin (DNJ), has been suggested as an antiviral agent for use in combination with N-(phosphonoacetyl)-L-aspartic acid (PALA) (WO 93/18763). However, combinations of N-substituted-imino-D-glucitol derivatives and other antiviral agents for the treatment of hepatitis virus infections have not been previously disclosed or suggested. From results obtained in a woodchuck animal model of hepatitis virus infection, Block et al. ((1998) Nature Medicine 4(5) :610–614) suggested that glucosidase inhibitors such as N-nonyl DNJ, which interfere with specific steps in the N-linked glycosylation pathway of hepatitis virus glycoproteins, may be useful in targeting glycosylation processing as a therapeutic intervention for hepatitis B virus.

Compounds such as N-butyl-DNJ (N-butyl-deoxynojirimycin) and N-butyl-DGNJ (N-butyl-desoxynogalactonojirimycin) are reported as treatments of lysosomal storage diseases such as Tay-Sachs disease, Gauchers disease and related ailments. In addition, treatment of cholera has been reported (U.S. Pat. No. 5,399,567) via inhibition of the synthesis of glycolipids (U.S. Pat. No.

5,472,969). Inhibition of glycosyl transferase or glycosidase enzymes that affect the catabolism and metabolism of phopholipids, sphingolipids, cerebrosides, gangliosides by or and within mammalian cells or interference with such biochemical processes as attachment to cells, penetration of cells and/or release from cells. In any event, treatments for these diseases are badly needed since "With rare exceptions a treatment of these often lethal diseases is not possible to date." (Kolter, T and Sandhoff, K, Inhibitors of Glycosphingolipid Biosynthesis, Chemical Society Reviews, 371–381 (1996), WO 98/02161

The use of N-butyl-1,5-dideoxy-1,5-imino-D-glucose and certain other imino-glucose compounds for the treatment of diseases caused or induced by human immunodeficincy virus (HIV), cytomeglovirus CMV), hepatitis virus, respiratory syncytial virus (RSV) and herpes virus (HSV) infection has been reported. Again, treatment of these infections is desirable and an important public goal.

Nucleoside and Nucleotide Antiviral Agents

Reverse transcriptase inhibitors, including the class of nucleoside and nucleotide analogs, were first developed as drugs for the treatment of retroviruses such as human immunodeficiency virus (HIV), the causative agent of AIDS. Increasingly, these compounds have found use against other viruses, including both RNA and DNA viruses, via viral screening and chemical modification strategies. Nucleoside and nucleotide analogs exert their antiviral activities by inhibiting the corresponding DNA and RNA polymerases responsible for synthesis of viral DNA and RNA, respectively. Because viruses contain different forms of polymerases, the same nucleoside/nucleotide compound can have a dramatically different effect against different viruses. For example, lamivudine (3TC) appears to be useful against HBV infection, whereas zidovudine (AZT) appears to have little use against the same virus (Gish, R. G., et al., *Exp. Opin. Invest. Drugs* (1995) 4(2):95–115).

AZT is an example of a nucleoside/nucleotide analog that can effect glycosylation processes at clinically achievable concentrations rather than interfere with DNA replication or protein synthesis (Yan, J., et.al., J. Biol. Chem., 270, 22836 (1995).

Toxicity has been significant with some nucleoside analog antivirals. For example, clinical tests on the use of the nucleoside analog fialuridine (FIAU) for treatment of chronic hepatitis B were suspended recently due to drug-related liver failure leading to death in some patients. Consequently, there is still a need for safer drug regimens for the treatment of hepatitis B infections and hepatitis (Mutchnick, M. G., et. al., *Antiviral Research* (1994) 24:245–257).

Immunomodulators and Immunostimulants

Immunomodulators/immunostimulators such as interferon alpha and other cytokines have been used for the treatment of HBV infection with promising results. Unfortunately, the response rates are lower than desired. Interferon treatment is currently approved by the FDA for the treatment of Hepatitis B. Other immune system-affecting drug candidates are presently being investigated. These include thymic peptides for use in the treatment of chronic hepatitis B (CHB), isoprinosine, steroids, Schiff base-forming salicylaldehyde derivatives such as Tucaresol, levamisol, and the like (Gish, R. G., et.al., *Exp. Opin. Invest. Drugs* (1995) 4(2):95–115; Coates, J. A. V., et.al., *Exp. Opin. Ther. Patents* (1995) 5(8):747–765).

SUMMARY OF THE INVENTION

As noted above, the use of the substituted-glucamine compounds and derivatives thereof disclosed herein alone, or in combination with other anti-hepatitis virus compounds has, to the present inventor's knowledge, neither been suggested nor disclosed. The use of two or more anti-viral agents to provide improved therapy for the treatment of hepatitis B virus and hepatitis C virus infections is desirable due to the morbidity and mortality of the disease. Combination therapy is also desirable since it can reduce toxicity in patients as it enables the physician to administer lower doses of one or more of the drugs being given to a patient. Combination therapy can also help to prevent the development of drug resistance in patients (Wiltink, E. H. H., *Pharmaceutish Weekblads Scientific Edition* (1992) 14(4A):268–274). The result of an improved efficacy configuration combined with a relative lack of toxicity and development of resistance would provide a much improved drug treatment profile.

Substituted glucamine compounds disclosed herein are effective in treating hepatitis virus infections. Furthermore, the use of these compounds in combination with nucleoside or nucleotide antiviral compounds, or combinations thereof, and/or immunomodulators/immunostimulants, results in unexpectedly greater anti-hepatitis virus effectiveness of the compounds compared to the combined antiviral activities expected of the individual compounds alone. Whether this is due to different mechanisms of action of the different classes of drugs employed or some other biological phenomenon is presently unclear.

Accordingly, in a first aspect, the present invention provides a method of treating a hepatitis virus infection in a mammal, comprising administering to said mammal an anti-hepatitis virus effective amount of at least one substituted-glucamine compound of Formula I or a pharmaceutically acceptable salt thereof:

The compound of Formula I corresponds to the structure:

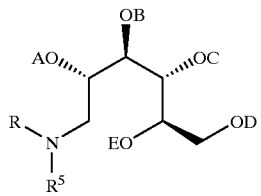

Formula I wherein:

R and $R^5$ are independently selected from the group consisting of H, aryloxyalkoxyalkyl, alkylcarbonyloxyalkyl, alkyl, arylcarbonyloxyalkyl, aminoalkyl, alkylcarbonylaminoalkyl, arylcarbonylaminoalkyl, alkoxycarbonylaminoalkyl, aminocarbonylaminoalkyl, aminothiocarbonylaminoalkyl, alkenyl, alkynyl, alkoxyalkyl, hydroxyalkyl, arylalkyl, arylalkenyl, carboxyalkyl, alkoxycarbonylalkyl, aminocarbonylalkyl, aminothiocarbonylalkyl, aminosulfonealkyl, arylalkynyl, heterocycloalkyl, heteroarylalkyl, heteroaryloxyalkyl, heteroarylthiaalkyl, heterocyclooxyalkyl, heterocyclothiaalkyl, aryloxyalkyl, arylthiaalkyl, haloalkyl, haloalkyloxyalkyl, carbonyl, cycloalkyloxyalkyl, cycloalkylalkyloxyalkyl, alkenylcarbonyl, alkynylcarbonyl, arylalkylcarbonyl, aryloxyalkylcarbonyl, haloalkylcarbonyl, hydroxyalkylcarbonyl, haloalkyloxyalkylcarbonyl, cycloalkyloxyalkylcarbonyl, alkoxyalkylcarbonyl, cycloalkylalkylcarbonyl, alkoxycarbonyl, alkylcarbonyl, aryloxyalkoxyalkylcarbonyl, alkylcarbonyloxyalkylcarbonyl, arylcarbonyloxyalkylcarbonyl, aminoalkylcarbonyl, alkylcarbonylaminoalkylcarbonyl, arylcarbonylaminoalkylcarbonyl, alkoxycarbonylaminoalkylcarbonyl, aminocarbonylaminoalkylcarbonyl, aminothiocarbonyl, aminoalkylcarbonyl, arylalkenylcarbonyl, carboxyalkylcarbonyl, alkoxycarbonylalkylcarbonyl, aminocarbonylalkylcarbonyl, aminothiocarbonylalkylcarbonyl, aminosulfonealkylcarbonyl, arylalkynylcarbonyl, heterocycloalkylcarbonyl, heteroarylalkyl, heteroaryloxyalkyl, heteroarylthiaalkylcarbonyl, heterocyclooxyalkylcarbonyl, heterocyclothiaalkylcarbonyl, arylthiaalkylcarbonyl, monohaloalkylcarbonyl, haloalkyloxyalkylcarbonyl, cycloalkylalkyloxyalkylcarbonyl, perhaloalkylaralkylt cycloalkyl, cycloalkylalkyl, cycloalkenyl, aryl, cycloalkenylalkyl, cycloalkenylalkenyl, cycloalkenylalkynyl, bicycloalkenylalkyl, tricycloalkenylalkyl, tetracycloalkenylalkyl, bicycloalkenoxyalkyl, tricycloalkenoxyalkyl, tetracycloalkenyloxyalkyl, cycloalkylalkenyl, cycloalkylalkynyl, aralkyl, aralkoxyalkyl, aralkoxyalkenyl, aralkoxyalkynyl, aralkenoxyalkyl, aralkenoxyalkenyl, heterocycloalkenyl, heteroarylakenyl, heteroarylalkynyl, aryloxyalkenyl, aryloxyalkynyl, hydroxyalkyl, dihydroxyalkyl, hydroxyalkenyl, dihydroxyalkenyl, hydroxyalkynyl, haloalkoxyalkenyl, haloalkoxyalkynyl, alkylcarbonyl, alkenylcarbonyl, alkynylcarbonyl, arylalkylcarbonyl, aryloxyalkylcarbonyl, hydroxyalkylcarbonyl, amino (alkyl), alkanoyl(amino)alkyl, (amino)carbonylalkyl, hydroxysulfonealkyl, (amino)carbonylaminoalkyl, cycloalkylcarbonyl, cycloalkylalkylcarbonyl, cycloalkenylcarbonyl, arylcarbonyl, cycloalkenylalkylcarbonyl, cycloalkenylalkenylcarbonyl, cycloalkenylalkynylcarbonyl, bicycloalkenylalkylcarbonyl, tricycloalkenylalkylcarbonyl, tetracycloalkenylalkylcarbonyl, bicycloalkenoxyalkylcarbonyl, tricycloalkenoxyalkylcarbonyl, tetracycloalkenyloxyalkylcarbonyl, cycloalkylalkenylcarbonyl, cycloalkylalkynylcarbonyl, aralkylcarbonyl, aralkoxyalkylcarbonyl, aralkoxyalkenylcarbonyl, aralkoxyalkynylcarbonyl, aralkenoxyalkylcarbonyl, aralkenoxyalkenylcarbonyl, heterocycloalkenylcarbonyl, heteroarylakenylcarbonyl, heteroarylalkynylcarbonyl, aryloxyalkenylcarbonyl, aryloxyalkynylcarbonyl, dihydroxyalkylcarbonyl, hydroxyalkenylcarbonyl, dihydroxyalkenylcarbonyl, hydroxyalkynylcarbonyl, haloalkoxyalkenylcarbonyl, and haloalkoxyalkynylcarbonyl, hydroxysulfonealkylcarbonyl, $R^7$ or $R^8$, wherein
$R^7=R^1X^1(R^2X^2)_m(R^3X^3)_n(R^4X^4)_pR^{13}$;
$R^8=R^9X^9(R^{10}X^{10})_q(R^{11}X^{11})_r(R^{12}X^{12})R^{13}$
$R^1$ and $R^9$ are independently selected from the group consisting of alkyl, aryl, alkenyl, alkynyl, hydrogen or haloalkyl;

$R^2$, $R^3$, $R^4$, $R^{10}$, $R^{11}$, $R^{12}$ and $R^{13}$ are independently selected from the group consisting of alkylene, alkenylene, alkynylene or haloalkylene;

$X^1$, $X^2$, $X^3$, $X^4$, $X^9$, $X^{10}$, $X^{11}$ and $X^{12}$ are independently oxygen, sulfur, sulfoxide or sulfone;

m, n, p, q, r and s are independently 0, 1, 2 or 3;

$m+n+p \leq 3$.

$q+r+s \leq 3$

A, B, C, D and E are independently hydrido, lower alkyl or acyl;

A and B taken together with the atoms to which they are attached may form a five or six membered heterocyclic ring;

B and C taken together with the atoms to which they are attached may form a five or six membered heterocyclic ring;

C and D taken together with the atoms to which they are attached may form a five or six membered heterocyclic ring;

C and E taken together with the atoms to which they are attached may form a five or six membered heterocyclic ring;

D and E taken together with the atoms to which they are attached may form a five or six membered heterocyclic ring.

In a second aspect, the present invention provides a method for treating a hepatitis virus infection in a mammal, comprising administering to said mammal an antiviral composition consisting essentially of an antiviral effective amount of at least one substituted-glucamine compound of Formula I as defined above, or a pharmaceutically acceptable salt thereof. In a third aspect, the present invention provides a method for treating a hepatitis virus infection in a mammal, comprising administering to said mammal an antiviral composition containing an antiviral effective amount of at least one substituted-glucamine compound of Formula I, as defined above or a pharmaceutically acceptable salt thereof, as above, substantially exclusive of the administration of any antiviral agent comprising a nucleoside, a nucleotide, an immunomodulator, or an immunostimulant.

In a fourth aspect, the present invention provides a method for treating a hepatitis virus infection in a mammal, consisting essentially of administering to said mammal an antiviral composition comprising an antiviral effective amount of at least one substituted-glucamine compound of Formula I, as defined above, or a pharmaceutically acceptable salt thereof, as above. In this method, the antiviral composition can consist essentially of an antiviral effective amount of the substituted-glucamine compound of Formula I, or a pharmaceutically acceptable salt thereof.

In a fifth aspect, the present invention provides a method of treating a hepatitis virus infection in a mammal, comprising administering to said mammal a first amount of at least one substituted-glucamine compound of Formula I, as defined above, or a pharmaceutically acceptable salt thereof and a second amount of an antiviral compound selected from the group consisting of a nucleoside antiviral compound, a nucleotide antiviral compound, an immunomodulator, an immunostimulant, and mixtures thereof, wherein said first and second amounts of said compounds together comprise an anti-hepatitis virus effective amount of said compounds.

In a sixth aspect the invention is directed to a method for treating a hepatitis virus infection in a mammal, consisting essentially of administering to said mammal an anti-hepatitis virus effective amount of an antiviral composition consisting essentially of at least one N-substituted-glucamine compound of Formula I or a pharmaceutically acceptable salt thereof.

In a seventh aspect, the invention is directed to a method consisting essentially of administering to said mammal an anti-hepatitis virus effective amount of a composition containing an anti-viral agent, said anti-viral agent consisting essentially of at least one N-substituted-glucamine compound of Formula I or a pharmaceutically acceptable salt thereof.

In another aspect, the present invention provides a method of treating a hepatitis virus infection in a mammal, comprising administering to said mammal from about 0.1 mg/kg/day to about 100 mg/kg/day of at least one N-substituted-glucamine compound of Formula I, as above, and from about 0.1 mg/person/day to about 500 mg/person/day of a compound selected from the group consisting of a nucleoside antiviral compound, a nucleotide antiviral compound, and a mixture thereof.

In another aspect, the present invention provides a pharmaceutical composition, consisting essentially of an antiviral effective amount of at least one N-substituted-glucamine compound of Formula I, as defined above, or a pharmaceutically acceptable salt thereof, as above and a pharmaceutically acceptable carrier, excipient, or diluent.

In another aspect, the present invention provides a pharmaceutical composition, containing an antiviral effective amount of at least substituted-glucamine compound of Formula I or a pharmaceutically acceptable salt thereof, as above, substantially exclusive of any antiviral agent comprising a nucleoside, a nucleotide, an immunomodulator, or an immunostimulant and a pharmaceutically acceptable carrier, diluent, or excipient.

In another aspect, the present invention provides a composition, comprising at least substituted-glucamine compound of Formula I, as above, and an antiviral compound selected from the group consisting of a nucleoside antiviral compound, a nucleotide antiviral compound, an immunomodulator, an immunostimulant, and mixtures thereof.

In another aspect, the present invention provides a pharmaceutical composition, comprising a first amount of at least one substituted-glucamine compound of Formula I, as above, a second amount of an antiviral compound selected from the group consisting of a nucleoside antiviral compound, a nucleotide antiviral compound, an immunomodulator, and immunostimulant, and mixtures thereof, and a pharmaceutically acceptable carrier, diluent, or excipient, wherein said first and second amounts of said compounds together comprise an antiviral effective amount of said compounds.

In yet a further aspect, the present invention provides a pharmaceutical composition for treating a hepatitis B virus infection in a mammal, comprising from about 0.1 mg to about 100 mg of at least one substituted-glucamine compound of Formula I, as above, and from about 0.1 mg to about 500 mg of a compound selected from the group consisting of a nucleoside antiviral compound, a nucleotide antiviral, and mixtures thereof, and a pharmaceutically acceptable carrier, diluent, or excipient.

Also provided is a pharmaceutical composition for treating a hepatitis B virus infection in a human patient, comprising from about 0.1 mg to about 100 mg of N-(n-nonenyl)-glucamine, from about 0.1 mg to about 500 mg of (−)-2′-deoxy-3′-thiocytidine-5′-triphosphate, and a pharmaceutically acceptable carrier, diluent, or excipient.

In another aspect, nucleosides and nucleotides and analogs such as AZT that inhibit sugar processing in addition to or instead of interfering with DNA or RNA are of special interest for use in combination therapy with iminosugars of this invention and for us in pharmaceutical formulations with the iminosugars disclosed herein. We intend that compounds such as AZT are useful in combination with the iminosugars disclosed herein for the treatment of diseases described with regard to the various aspects of this invention.

Each of the methods of the invention as described hereinabove is effective for treating various forms of infectious hepatitis. Forms of hepatitis which can be treated by administration of the above-described imino sugars include hepatitis B, hepatitis C, hepatitis delta, hepatitis E, hepatitis F and hepatitis G. The methods of the invention are particularly suited and preferred for the treatment of hepatitis B and hepatitis C.

In another aspect, the present invention provides intermediates useful for the preparation of substituted-glucamine compounds or a salt thereof used alone or in combination in the treatment of Hepatitis B infection.

Also provided is a salt, comprising an anti-hepatitis effective amount of an N-substituted-glucamine compound of Formula I, as described above, and a nucleoside having an acidic moiety or a nucleotide.

Also provided is a compound, comprising an N-substituted-glucamine compound selected from:

The compound of Formula I corresponds to the structure:

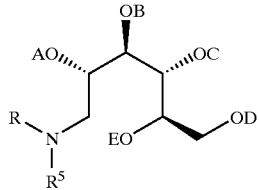

Formula I wherein: R is aryloxyalkyl, monohaloalkyl, haloalkyloxyalkyl, cycloalkyloxyalkyl, cycloalkylalkyloxyalkyl, alkenylcarbonyl, alkynylcarbonyl, arylalkylcarbonyl, arylalkyloxycarbonyl, aryloxyalkylcarbonyl, haloalkylcarbonyl, hydroxyalkylcarbonyl, haloalkyloxyalkylcarbonyl, cycloalkyloxyalkylcarbonyl, alkoxyalkylcarbonyl, perhaloalkylaralkyl, cycloalkyl, cycloalkylalkyl, cycloalkenyl, aryl, cycloalkenylalkyl, cycloalkenylalkenyl, cycloalkenylalkynyl, bicycloalkenylalkyl, tricycloalkenylalkyl, tetracycloalkenylalkyl, bicycloalkenoxyalkyl, tricycloalkenoxyalkyl, tetracycloalkenyloxyalkyl, cycloalkylalkenyl, cycloalkylalkynyl, aralkyl, aralkoxyalkyl, aralkoxyalkenyl, aralkoxyalkynyl, aralkenoxyalkyl, aralkenoxyalkenyl, heterocycloalkenyl, heteroarylakenyl, heteroarylalkynyl, aryloxyalkyl, aryloxyalkenyl, aryloxyalkynyl, hydroxyalkyl, dihydroxyalkyl, hydroxyalkenyl, dihydroxyalkenyl, hydroxyalkynyl, haloalkoxyalkenyl, haloalkoxyalkynyl, alkylcarbonyl, alkenylcarbonyl, alkynylcarbonyl, arylalkylcarbonyl, aryloxyalkylcarbonyl, hydroxyalkylcarbonyl, amino (alkyl), alkanoyl(amino)alkyl, (amino)carbonylalkyl, hydroxysulfonealkyl, (amino)carbonylaminoalkyl, or $R^5$, wherein $R7 = R^1X^1(R^2X^2)_m(R^3X^3)_n(R^4X^4)_pR^{13}$;
$R8 = R^9X^9(R^{10}X^{10})_q(R^{11}X^{11})_r(R^{12}X^{12}) R^{13}$ $R^1$ and $R^9$ are independently selected from the group consisting of alkyl, aryl, alkenyl, alkynyl, hydrogen or haloalkyl;

$R^2$, $R^3$, $R^4$, $R^{10}$, $R^{11}$, $R^{12}$ and $R^{13}$ are independently selected from the group consisting of alkylene, alkenylene, alkynylene or haloalkylene;

$X^1$, $X^2$, $X^3$, $X^4$, $X^9$, $X^{10}$, $X^{11}$ and $X^{12}$ are independently oxygen, sulfur, sulfoxide or sulfone;

m, n, p, q, r and s are independently 0, 1, 2 or 3;

$m+n+p \leq 3$ $q+r+s \leq 3$

A, B, C, D and E are independently hydrido, lower alkyl or acyl;

A and B taken together with the atoms to which they are attached may form a five or six membered heterocyclic ring;

B and C taken together with the atoms to which they are attached may form a five or six membered heterocyclic ring;

C and D taken together with the atoms to which they are attached may form a five or six membered heterocyclic ring;

C and E taken together with the atoms to which they are attached may form a five or six membered heterocyclic ring;

D and E taken together with the atoms to which they are attached may form a five or six membered heterocyclic ring;

wherein the main chain in R or $R^5$ contains between one and twenty atoms;

the main chain of each of $R^7$ and $R^8$ contains between four and twenty atoms and either of $R^1X^1$ or $R^9X^9$; provided that R and $R^5$ are not both hydrido.

Further scope of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

Figure 1:
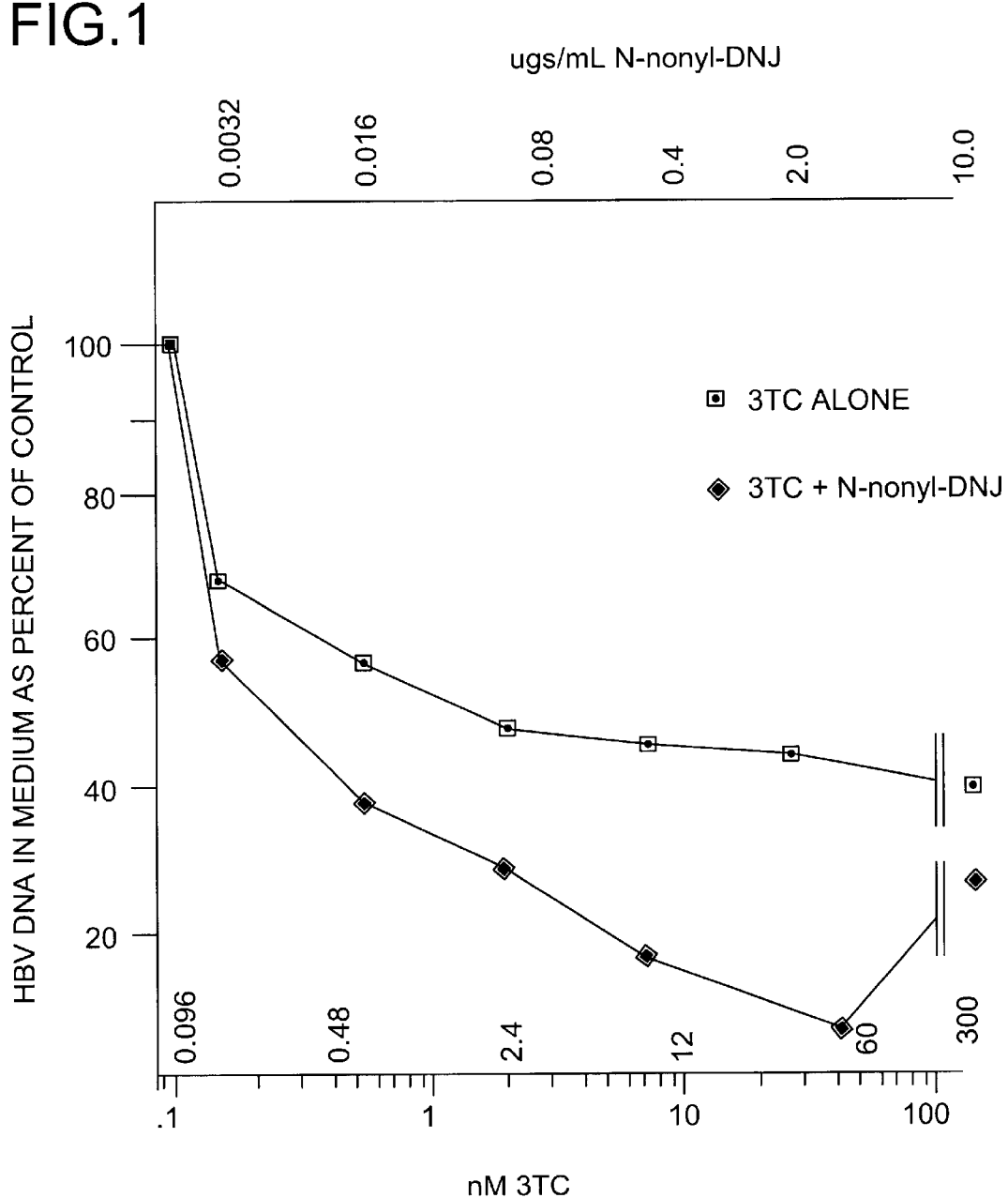
FIG. 1 shows the anti-hepatitis B virus activity of (−)-2'-deoxy-3'-thiocytidine-5'-triphosphate (3TC) alone and in combination with N-nonyl-DNJ in vitro.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the patent documents and other references cited herein, including the contents of the references cited within these primary references, are herein incorporated by reference in their entirety.

It has been discovered that the use of substituted-glucamine compounds is effective when such compounds are used alone for treating hepatitis virus infections. In accordance with the present invention, it has additionally been discovered that combinations of substituted-glucamine compounds with anti-hepatitis virus nucleosides or nucleotides, and/or immunomodulators/immunostimulants, are also effective for this purpose. There is some evidence that certain combinations may be more effective in inhibiting hepatitis virus replication than would have been expected via the combined use of the individual compounds.

The present invention thus provides pharmaceutical compositions and methods of treating hepatitis virus infections, especially hepatitis B and C virus infections, in humans, other mammals, and cells using substituted-glucamine compounds alone or in combination with either an antiviral nucleoside, an antiviral nucleotide, mixtures thereof, and/or an immunomodulating or immunostimulating agent. The substituted-glucamine compounds may have basic nitrogen atoms and may be used in the form of a pharmaceutically acceptable salt. Nucleosides and nucleotides useful in the present invention are substituted purine or pyrimidine heterocycles further substituted with $R^1$ in Formulas II–VI at the 9 position in the case of purines or with $R^1$ at the 1 position in the case of pyrimidines. The immunomodulating and immunostimulating agents useful in the present invention include those that stimulate immune responses effective in controlling or eliminating viruses or other infectious agents. Non-limiting examples of such immunomodulating and immunostimulating agents, include cytokines, peptide agonists, steroids, and classic drugs such as levamisol. The drug combinations of this invention may be provided to a cell or cells, or to a human or other mammalian patient, either in separate pharmaceutically acceptable formulations administered simultaneously or sequentially, formulations containing more than one therapeutic agent, or by an assortment of single agent and multiple agent formulations. However administered, these drug combinations form an anti-hepatitis virus effective amount of components.

As used herein, the term "anti-hepatitis-virus effective amount" refers to an amount of an N-substituted-glucamine compound alone, or a combined amount of (1) an N-substituted-glucamine compound with either an antiviral nucleoside, an antiviral nucleotide, a mixture of an antiviral nucleoside and an antiviral nucleotide, or an immunomodulating/-immunostimulating agent (or mixtures thereof), or (2) a combined amount of an N-substituted-glucamine compound with an antiviral nucleoside, an antiviral nucleotide, or a mixture thereof, and an immunomodulating/-immunostimulating agent (or mixtures thereof) effective in treating hepatitis virus infection. The antiviral effectiveness of the aforementioned combinations may involve a variety of different phenomena associated with viral replication and assembly. These may include, for example, blocking hepatitis viral DNA synthesis; blocking viral transcription; blocking virion assembly; blocking virion release or secretion from infected cells; blocking or altering viral protein function, including the function of viral envelope protein(s); and/or the production of immature or otherwise non-functional virions. The overall effect is an inhibition of viral replication and infection of additional cells, and therefore inhibition of the progress of infection in the patient.

Substituted-Glucamine Compounds

Substituted-glucamine compounds useful in the present invention are represented by structure Formula I above or salts thereof.

As utilized herein, the term "alkyl", alone or in combination, means a straight-chain or branched-chain alkyl radical containing from 1 to and including 20 carbon atoms. Substituted alkyl, alone or in combination, means an alkyl radical which is optionally substituted as defined herein with respect to the definitions of aryl and heterocyclo. Alkylene means a saturated aliphatic hydrocarbyl attached at two or more positions such as methylene (—$CH_2$—). Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "lower alkyl", alone or in combination, means alkyl containing from 1 to and including 6 carbon atoms.

The phrase "in the main chain" means the longest contiguous or adjacent chain of carbon atoms starting at the point of attachment of a group to the compounds of this invention.

The phrase "linear chain of atoms" means the longest straight chain of atoms independently selected from carbon, nitrogen, oxygen and sulfur.

The term "hydrido" means a hydrogen substituent, i.e., —H.

The term "alkenyl", alone or in combination, means a straight-chain or branched-chain hydrocarbon radical having one or more double bonds and containing from 2 to 20 carbon atoms. Substituted alkenyl, alone or in combination, means an alkyl radical which is optionally substituted as defined herein with respect to the definitions of aryl and heterocyclo. Alkenylene means a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like.

The term lower "alkenyl", alone or in combination, means alkyl containing from 1 to and including 6 carbon atoms.

The term "alkynyl", alone or in combination, means a straight-chain or branched chain hydrocarbon radical having one or more triple bonds and containing preferably from 2 to 20 carbon atoms. Substituted alkynyl, alone or in combination, means an alkyl radical which is optionally substituted as defined herein with respect to the definitions of aryl and heterocyclo. Alkynylene means a carbon-carbon triple bond attached at two positions such as ethynylene (—C:::C—). Examples of alkynyl radicals include ethynyl, propynyl (propargyl), butynyl and the like.

The term lower "alkynyl", alone or in combination, means alkyl containing from 1 to and including 6 carbon atoms.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, isobutoxy, sec-butoxy, tert-butoxy, ethoxyethoxy, methoxypropoxyethoxy, ethdxypentoxyethoxyethoxy and the like.

The term "cycloalkyl", alone or in combination, means a saturated or partially saturated monocyclic, bicyclic or tricyclic alkyl radical wherein each cyclic moiety contains preferably from 3 to 10 carbon atom ring members and which may optionally be a benzo fused ring system which is optionally substituted as defined herein with respect to the definition of aryl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2,2,2]octane, bicyclo[2,2,2]octane, bicyclo[1,1,1]pentane, camphor and bicyclo[3,2,1]octane.

The term "cycloalkylalkyl" means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The terms "benzo" or "benz", alone or in combination, means the divalent radical $C_6H_4$= derived from benzene. Examples include benzothiophene and benzimidazole.

The term "aryl", alone or in combination, or "ara" or" "ar" in combination, means a phenyl (-Ø) or naphthyl radical which is optionally substituted with one or more substituents selected from the group consisting of alkyl, alkylcarbonyl, alkoxy, halogen, hydroxy, amino, nitro, cyano, haloalkyl, haloalkylthio, haloalkyloxy, carboxy, alkoxycarbonyl, cycloalkyl, heterocyclo, alkylcarbonylamino, aminoalkanoyl, amido, aminocarbonyl, arylcarbonyl, arylcarbonylamino, aryl, aryloxy, alkyloxycarbonyl, arylalkyloxycarbonyl alkoxycarbonylamino, disubstituted amino, aminocarbonyl, disubstituted aminocarbonyl, amido, disubstitutedamido, aralkoxycarbonylamino, alkylthio, alkylsulfinyl, alkylsulfonyl, haloalkylthio, haloalkylsulfinyl, haloalkylsulfonyl, arylthio, arylsulfinyl, arylsulfonyl, alkylsulfinylamino, alkylsulfonylamino, haloalkylsulfinylamino, haloalkylsulfonylamino, arylsulfinylamino, arylsulfonylamino, heterocyclo, sulfonate, sulfonic acid, trisubstitutedsilyl and the like. Examples of aryl radicals are phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 4-$CF_3$-phenyl, 2-methyl-3-aminophenyl, 4-$CF_3$O-phenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like.

The terms "aralkyl" and "aralkoxy", alone or in combination, means an alkyl or alkoxy radical as defined above in which at least one hydrogen atom is replaced by an aryl radical as defined above. Thus, "aryl" includes substituents such as benzyl, 2-phenylethyl, dibenzylmethyl, hydroxyphenylmethyl, methylphenylmethyl, and diphenylmethyl, and "aryloxy" includes substituents such as benzyloxy, diphenylmethoxy, 4-methoxyphenylmethoxy and the like.

The term "aralkoxycarbonyl", alone or in combination, means a radical of the formula aralkyl-O—C(O)— in which the term "aralkyl", has the significance given above. Examples of an aralkoxycarbonyl radical are benzyloxycarbonyl (Z) and 4-methoxyphenylmethoxycarbonyl (MOS).

The term "aryloxy" means a radical of the formula aryl-O-in which the term aryl has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "alkylcarbonyl" (alkyl-(C=O)—) means alkanoyl. The term "cycloalkylcarbonyl" means an acyl radical of the formula cycloalkyl-(C=O)— in which the term "cycloalkyll" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like.

The term "aralkanoyl" means an acyl radical derived from an aryl-substituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" means an acyl radical derived from an arylcarboxylic acid, "aryl" having the meaning given above. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "arylcarbonyl" is aroyl.

Where substituents are recited without qualification as to substitution, both substituted and unsubstituted forms are encompassed. Where a substituent is qualified as "substituted," the substituted form is specifically intended.

The term "substituted", when used in combination and not otherwise defined in this paragraph, means one to four substituents attached that are independently selected from the group comprising alkyl, alkylcarbonyl, alkoxy, halogen, hydroxy, amino, nitro, cyano, thiol, haloalkyl, carboxy, alkoxycarbonyl, cycloalkyl, heterocyclo, alkanoylamino, aminoalkanoyl, amido, aminocarbonyl, arylcarbonyl, aryl, aryloxy, alkyloxycarbonyl, arylalkyloxycarbonyl, alkoxycarbonylamino, amino, disubstituted amino, substituted aminocarbonyl, disubstituted aminocarbonyl, substituted amido, disubstitutedamido, aralkoxycarbonylamino, alkylthio, alkylsulfinyl, alkylsulfonyl, arylthio, arylsulfinyl, arylsulfonyl, heterocyclo, sulfonate, sulfonic acid and trisubstitutedsilyl.

The term "carbonyl", alone includes formyl [—(C=O)—H] and in combination is a —C=O— group.

The term "oxo" means the double bonded oxygen.

The term "thiocarbonyl", alone includes thioformyl [—(C=S)—H] and in combination is a —C=S— group.

The term "oxy" or "oxa" means a —O— group.

The term "carboxy" is —COOH or the corresponding "carboxylate" anion such as is in a carboxylic acid salt.

The term "heterocyclo," alone or in combination, means a saturated or partially unsaturated monocyclic, bicyclic or tricyclic heterocycle radical containing at least one, preferably 1 to 4, more preferably 1 to 2, nitrogen, oxygen or sulfur atom ring members and having preferably 3 to 8 ring members in each ring, more preferably 3 to 7 ring members in each ring and most preferably 5 to 6 ring members in each ring. "Heterocyclo" is intended to include sulfones, sulfoxides, N-oxides of tertiary nitrogen ring members, and carbocyclic fused and benzo fused ring systems. Such heterocyclo radicals may be optionally substituted on at least one, preferably 1 to 4, more preferably 1 to 2, carbon atoms by halogen, alkyl, alkoxy, hydroxy, oxo, aryl, aralkyl, heteroaryl, heteroaralkyl, amidino, N-alkylamidino, alkoxycarbonylamino, alkylsulfonylamino and the like, and/or on a secondary nitrogen atom (i.e., —NH—) by hydroxy, alkyl, aralkoxycarbonyl, alkanoyl, heteroaralkyl, phenyl or phenylalkyl, and/or on a tertiary nitrogen atom (i.e., =N—) by oxido.

The term "heterocycloalkyl" means an alkyl radical as defined above in which at least one hydrogen atom is replaced by a heterocyclo radical as defined above, such as pyrrolidinylmethyl, tetrahydrothienylmethyl, pyridylmethyl and the like.

The term "heteroaryl", alone or in combination, means an aromatic heterocyclo radical as defined above, which is optionally substituted as defined above with respect to the definitions of aryl and heterocyclo. Examples of such heterocyclo and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl, etc.), pyrazinyl, pyrimidinyl, furyl, tetrahydrofuryl, thienyl, tetrahydrothienyl and its sulfoxide and sulfone derivatives, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, methylenedioxyphen-4-yl, methylenedioxyphen-5-yl, ethylenedioxyphenyl, benzothiazolyl, benzopyranyl, benzofuryl, 2,3-dihydrobenzofuryl, benzoxazolyl, thiopheneyl and the like.

The term "cycloalkylalkoxycarbonyl" means an acyl group derived from a cycloalkylalkoxycarboxylic acid of the formula cycloalkylalkyl-O—COOH wherein cycloalkylalkyl has the meaning given above.

The term "aryloxyalkanoyl", means an acyl radical of the formula aryl-O-alkanoyl wherein aryl and alkanoyl have the meaning given above.

The term "heterocycloalkoxycarbonyl" means an acyl group derived from heterocycloalkyl-O—COOH wherein heterocycloalkyl is as defined above.

The term "heterocycloalkanoyl" is an acyl radical derived from a heterocycloalkylcarboxylic acid wherein heterocyclo has the meaning given above.

The term "heterocycloalkanoyl" is an acyl radical derived from a heterocycloalkylcarboxylic acid wherein heterocyclo has the meaning given above.

The term "heterocycloalkoxycarbonyl" means an acyl radical derived from a heterocycloalkyl-O—COOH wherein heterocyclo has the meaning given above.

The term "heteroaryloxycarbonyl" means an acyl radical derived from a carboxylic acid represented by heteroaryl-O—COOH wherein heteroaryl has the meaning given above.

The term "trisubstitutedsilyl", alone or in combination, means a silicone group substituted at its three free valences with groups as listed herein under the definition of substituted amino. Examples include trimethysilyl, tert-butyldimethylsilyl, triphenylsilyl and the like.

The terms "sulfonate", "sulfonic acid" and "sulfonic", alone or in combination, mean the —SO$_3$H group and its anion as the sulfonic acid is used in salt formation.

The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like.

The term "amido", alone or in combination, means the product of the combination of a carboxylic acid with an amine as defined herein.

The term "amino", alone or in combination, means an —N= group wherein the amino group can be a primary, secondary or tertiary amino group containing substituents selected from alkyl, aryl, aralkyl, cycloalkyl, cycloalkylalkyl radicals and the like. Primary amino has two free valences as hydrogen, i.e., —NH$_2$. Secondary amino, which is also mono-substituted amino or N-substituted amino, has one free valence substituted as above. Tertiary amino, which is also disubstituted amino or N,N-disubstituted amino, has two free valences substituted as above. For example, —NH$_2$ is unsubstituted amino, —N(H)(CH$_3$) is mono-substituted amino (N-methylamino) and —N(CH3)(CH$_2$phenyl), is disubstituted amino (N-methyl-N-benzylamino).

The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like.

The term "halogen" means fluorine, chlorine, bromine or iodine.

The term "haloalkyl", alone or in combination, means an alkyl radical having the meaning as defined above wherein one or more hydrogens are replaced with a halogen. Haloalkylene means a halohydrocarbyl group attached at two or more positions. Examples include fluoromethylene (—CFH—), difluoromethylene (—CF$_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "lowerhaloalkyl", alone or in combination, means haloalkyl containing from 1 to and including 6 carbon atoms.

The terms "thia" and "thio", alone or in combination, mean a —S— group or an ether wherein the oxygen is replaced with a sulfur. The oxidized derivatives of the thio function are included. Examples include alkylthia groups such as methylthia and oxidation products such as the sulfoxide [—(S—O)—] and sulfone [—(S—O$_2$)—] derivatives.

The term "thiol" means an —SH group. The term "leaving group" (L or W) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The definitions above apply except where are specified otherwise. For example, monohaloalkyl specifically means an alkyl group with one halogen substituent.

Compounds disclosed herein are those expected to be sufficiently stable to be used as presented herein or to be used in the preparation of the materials shown herein.

This specifically includes temporary or transient intermediates in chemical reactions and compounds that may exist in different forms depending upon their environment. It is well known in the art that stability is partially defined in relation to use. For illustration, aldehydes may be hydrated when in an aqueous system but not hydrated in a non-aqueous system and various solvates may be used in pharmaceutical compositions rather than an anhydrous compound. The pharmaceutical chloral is a material wherein the soporific is conveniently administered as the hydrate (chloral hydrate) whereas the anhydrous form (trichloroacetaldehyde) is conveniently used (or made in situ) as a reagent or substrate in synthetic reactions such Wittig reactions.

The present invention comprises any tautomeric forms of compounds of Formula I. The present invention also comprises compounds of Formula I having one or more asymmetric carbons. It is known to those skilled in the art that those imino sugars of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

Representative glucamine compounds useful in the present invention include, but are not limited to compounds in the Tables:

TABLE 1
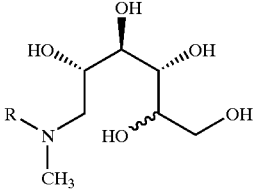
| | R |
|---|---|
| 1. | 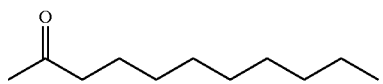 |
| 2. | 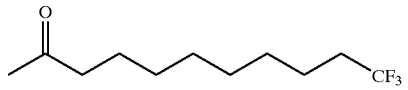 |
| 3. | 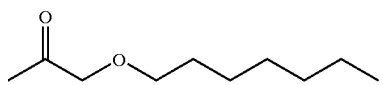 |
| 4. | 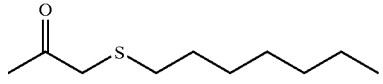 |
| 5. | 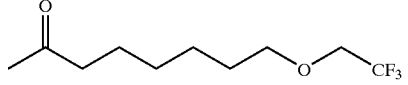 |
| 6. | 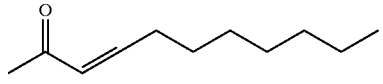 |
| 7. | 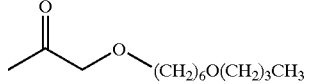 |
| 8. | 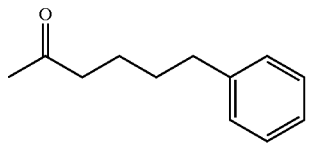 |
| 9. | 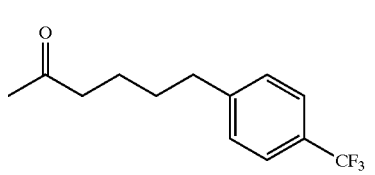 |
| 10. | 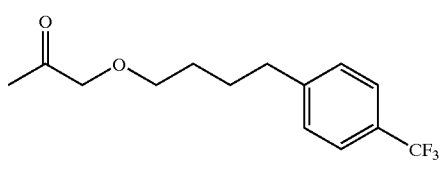 |
| 11. | 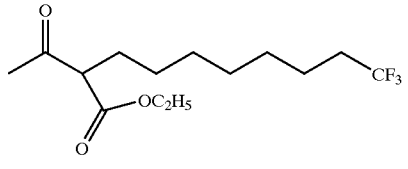 |
TABLE 1-continued
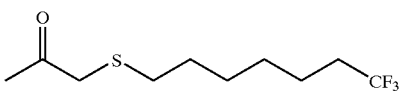
| | R |
|---|---|
| 12. | 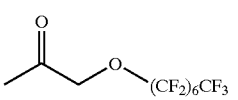 |
| 13. |  |
| 14. |  |
| 15. | 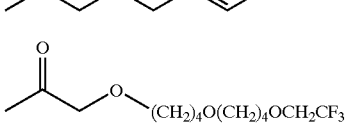 |
| 16. | $\underset{\text{O}}{\overset{\text{O}}{\|}}\!\!\!\!\!\!\!\!\!\!\!\!\!\!\!\!\!\!\!\text{—}\text{O}(CH_2)_4O(CH_2)_4OCH_2CF_3$ |
TABLE 2
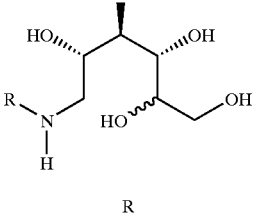
| | R |
|---|---|
| 1. | $-(CH_2)_{11}CF_3$ |
| 2. | $-(CH_2)_7O(CH_2)_2OCH_2CF_3$ |
| 3. | $-(CH_2)_4O(CH_2)_4CF_3$ |
| 4. | $-(CH_2)_4OCH_2$—C$_6$H$_4$—CH$_3$ |
| 5. | $-(CH_2)_4OCH_2$—C$_6$H$_4$—CF$_3$ |
| 6. | $-(CH_2)_4OCH_2$—C$_6$H$_4$—F |
| 7. | $-(CH_2)_5O(CH_2)_3$—C$_6$H$_5$ |

TABLE 2-continued

[Structure: pentitol chain with OH groups and R-NH-CH2- substituent]

R

8. —(CH₂)₂O(CH₂)₃O—C₆H₄—OCH₃

9. —(CH₂)₂O(CH₂)₃O—C₆H₄—CF₃

10. —(CH₂)₂O(CH₂)₂—cyclohexyl

11. —(CH₂)₄O—cyclohexyl

12. —(CF₂)₇CF₃
13. —(CH₂)₇O(CF₂)₇CF₃
14. —CF₂CH₂O(CH₂)₃SCF₃
15. —(CH₂)₄S(CH₂)₄CF₃
16. —(CH₂)₇S(CH₂)₂SCF₃
17. —(CH₂)₇S(CH₂)₂SCH₂CF₃

18. —(CH₂)₄SCH₂—C₆H₄—OCF₃

19. —(CH₂)₂S(CH₂)₃O—C₆H₄—OCH₃

20. —(CH₂)₂O(CH₂)₂S—C₆H₄—CF₃

21. —(CH₂)₂S(CH₂)₂—cyclohexyl

22. —(CH₂)₄S—cyclohexyl

TABLE 3

[Structure: hexitol chain with OH groups and R-NH-CH2- substituent]

R

1. —(CH₂)₂O(CH₂)₆CF₃
2. —(CH₂)₆O(CH₂)₂CF₃
3. —(CH₂)₂O(CH₂)₂O(CH₂)₂OCF₃
4. —(CH₂)₆O(CH₂)₂O(CH₂)₂OCF₃
5. —(CH₂)₂O(CH₂)₂O(CH₂)₃CF₃
6. —(CH₂)₂O(CH₂)₂O(CH₂)₂CF₃

7. —(CH₂)₄O—C₆H₄—OCF₃

8. —(CH₂)₆O—C₆H₄—OCF₃

9. —(CH₂)₆S(CH₂)₂CF₃
10. —(CH₂)₄S(CH₂)₂CF₃
11. —(CH₂)₂S(CF₂)₆CF₃
12. —CH₂(CHOH)CH₂(CHNH₂)(CH₂)₁₂CH₃
13. —(CH₂)₂O(CF₂)₂O(CH₂)₂OCF₃
14. —(CH₂)₆S(CH₂)₂O(CH₂)₂OCF₃
15. —(CH₂)₂O(CH₂)₂O(CH₂)₂CF₂CF₃
16. —(CH₂)₂O(CH₂)₂S(CH₂)₂CF₃

17. —(CH₂)₄S—C₆H₄—OCF₃

18. —(CH₂)₆S—C₆H₄—OCF₃

19 —(CH₂)₆S(CH₂)₂SO₂CF₃
20 —(CH₂)₄O(CH₂)₂SO₂CF₃

TABLE 4

[Structure: hexitol chain with OH groups and R-N(CH₃)-CH2- substituent]

R

1. —(CH₂)₂O(CH₂)₆CF₃
2. —(CH₂)₆O(CH₂)₂CF₃
3. —(CH₂)₂O(CH₂)₂O(CH₂)₂OCF₃
4. —(CH₂)₆O(CH₂)₂O(CH₂)₂OCF₃
5. —(CH₂)₂O(CH₂)₂O(CH₂)₃CF₃
6. —(CH₂)₂O(CH₂)₂O(CH₂)₂CF₃

7. —(CH₂)₄O—C₆H₄—OCF₃

TABLE 4-continued

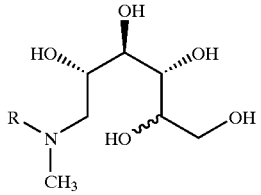

| R |
|---|
| 8. 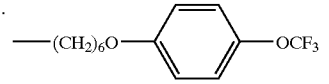 —(CH$_2$)$_6$O—⟨C$_6$H$_4$⟩—OCF$_3$ |
| 9. —(CH$_2$)$_6$S(CH$_2$)$_2$CF$_3$ |
| 10. —(CH$_2$)$_4$S(CH$_2$)$_2$CF$_3$ |
| 11. —(CH$_2$)$_2$S(CF$_2$)$_6$CF$_3$ |
| 12. —CH$_2$(CHOH)CH$_2$(CHNH$_2$)(CH$_2$)$_{12}$CH$_3$ |
| 13. —(CH$_2$)$_2$O(CF$_2$)$_2$O(CH$_2$)$_2$OCF$_3$ |
| 14. —(CH$_2$)$_6$S(CH$_2$)$_2$O(CH$_2$)$_2$OCF$_3$ |
| 15. —(CH$_2$)$_2$O(CH$_2$)$_2$O(CH$_2$)$_2$CF$_2$CF$_3$ |
| 16. —(CH$_2$)$_2$O(CH$_2$)$_2$S(CH$_2$)$_2$CF$_3$ |
| 17. 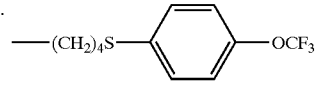 —(CH$_2$)$_4$S—⟨C$_6$H$_4$⟩—OCF$_3$ |
| 18. 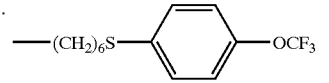 —(CH$_2$)$_6$S—⟨C$_6$H$_4$⟩—OCF$_3$ |
| 19 —(CH$_2$)$_6$S(CH$_2$)$_2$SO$_2$CF$_3$ |
| 20 —(CH$_2$)$_4$O(CH$_2$)$_2$SO$_2$CF$_3$ |

TABLE 5

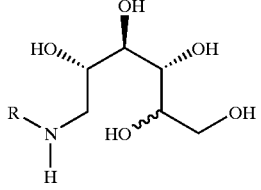

| R |
|---|
| 1. 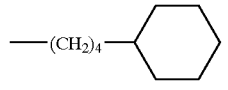 —(CH$_2$)$_4$-cyclohexyl |
| 2. 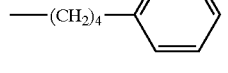 —(CH$_2$)$_4$-phenyl |
| 3. 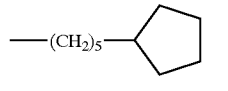 —(CH$_2$)$_5$-cyclopentyl |
| 4. 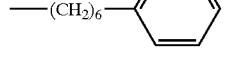 —(CH$_2$)$_6$-phenyl |

TABLE 5-continued

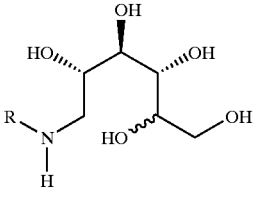

| R |
|---|
| 5. 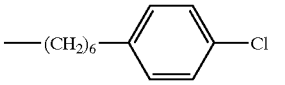 —(CH$_2$)$_6$—⟨C$_6$H$_4$⟩—Cl |
| 6. 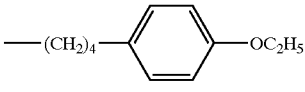 —(CH$_2$)$_4$—⟨C$_6$H$_4$⟩—OC$_2$H$_5$ |
| 7. 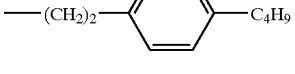 —(CH$_2$)$_2$—⟨C$_6$H$_4$⟩—C$_4$H$_9$ |
| 8. 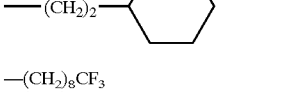 —(CH$_2$)$_2$-cyclohexyl |
| 9. —(CH$_2$)$_8$CF$_3$ |
| 10. —(CH$_2$)$_7$CF$_3$ |
| 11. —(CH$_2$)$_9$CF$_3$ |
| 12. —(CH$_2$)$_8$CH$_3$ |
| 13. —(CH$_2$)$_9$CH$_3$ |
| 14. 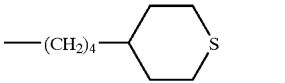 —(CH$_2$)$_4$-tetrahydrothiopyranyl |
| 15. 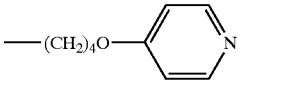 —(CH$_2$)$_4$O-pyridyl |
| 16. 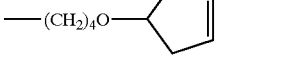 —(CH$_2$)$_4$O-cyclopentenyl |
| 17. 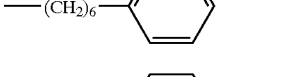 —(CH$_2$)$_6$-pyridyl |
| 18. 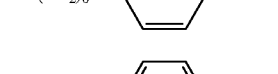 —(CH$_2$)$_6$—⟨C$_6$H$_4$⟩—SCF$_3$ |
| 19. 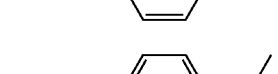 —(CH$_2$)$_4$—⟨C$_6$H$_4$⟩—OCF$_2$CF$_3$ |
| 20. 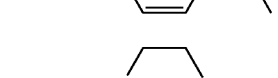 —(CH$_2$)$_2$—⟨C$_6$H$_4$⟩—isopropyl |
| 21. 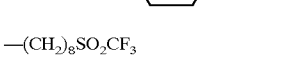 —(CH$_2$)$_2$—morpholinyl |
| 22. —(CH$_2$)$_8$SO$_2$CF$_3$ |

TABLE 5-continued

[Structure: deoxynojirimycin-derived polyol with R-NH- group]

| R | |
|---|---|
| 23. | —(CH$_2$NH(CH$_2$)$_4$SO$_2$CF$_3$ |
| 24. | —(CH$_2$)$_9$NHSO$_2$CF$_3$ |
| 25. | —(CH$_2$)$_8$SO$_2$NHC$_6$H$_5$ |
| 26. | —(CH$_2$)$_9$SO$_2$—[2-naphthyl] |

TABLE 6

[Structure: deoxynojirimycin-derived polyol with R-N(CH$_3$)- group]

| R | |
|---|---|
| 1. | —(CH$_2$)$_4$—cyclohexyl |
| 2. | —(CH$_2$)$_4$—phenyl |
| 3. | —(CH$_2$)$_5$—cyclopentyl |
| 4. | —(CH$_2$)$_6$—phenyl |
| 5. | —(CH$_2$)$_6$—C$_6$H$_4$—Cl |
| 6. | —(CH$_2$)$_4$—C$_6$H$_4$—OC$_2$H$_5$ |
| 7. | —(CH$_2$)$_2$—C$_6$H$_4$—C$_4$H$_9$ |
| 8. | —(CH$_2$)$_2$—cyclohexyl |

TABLE 6-continued

[Structure: deoxynojirimycin-derived polyol with R-N(CH$_3$)- group]

| R | |
|---|---|
| 9. | —(CH$_2$)$_8$CF$_3$ |
| 10. | —(CH$_2$)$_7$CF$_3$ |
| 11. | —(CH$_2$)$_9$CF$_3$ |
| 12. | —(CH$_2$)$_8$CH$_3$ |
| 13. | —(CH$_2$)$_9$CH$_3$ |
| 14. | —(CH$_2$)$_4$—tetrahydrothiopyranyl |
| 15. | —(CH$_2$)$_4$O—(4-pyridyl) |
| 16. | —(CH$_2$)$_4$O—cyclopentenyl |
| 17. | —(CH$_2$)$_6$—(2-pyridyl) |
| 18. | —(CH$_2$)$_6$—C$_6$H$_4$—SCF$_3$ |
| 19. | —(CH$_2$)$_4$—C$_6$H$_4$—OCF$_2$CF$_3$ |
| 20. | —(CH$_2$)$_2$—C$_6$H$_4$—CH(CH$_3$)$_2$ |
| 21. | —(CH$_2$)$_2$—morpholinyl |
| 22. | —(CH$_2$)$_8$SO$_2$CF$_3$ |
| 23. | —CH$_2$NH(CH$_2$)$_4$SO$_2$CF$_3$ |
| 24. | —(CH$_2$)$_9$NHSO$_2$CF$_3$ |
| 25. | —(CH$_2$)$_8$SO$_2$NHC$_6$H$_5$ |
| 26. | —(CH$_2$)$_9$SO$_2$—[2-naphthyl] |

TABLE 7

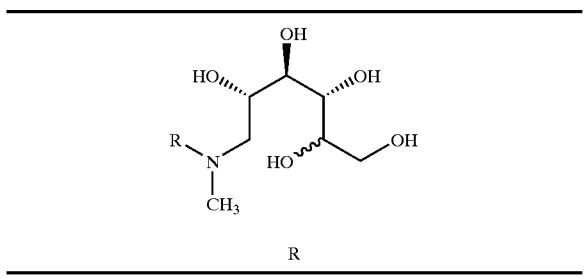

| R |
|---|
| 1. —(CH$_2$)$_{11}$CF$_3$ |
| 2. —(CH$_2$)$_7$O(CH$_2$)$_2$OCH$_2$CF$_3$ |
| 3. —(CH$_2$)$_4$O(CH$_2$)$_4$CF$_3$ |
| 4. —(CH$_2$)$_4$OCH$_2$—C$_6$H$_4$—CH$_3$ |
| 5. —(CH$_2$)$_4$OCH$_2$—C$_6$H$_4$—CF$_3$ |
| 6. —(CH$_2$)$_4$OCH$_2$—C$_6$H$_4$—F |
| 7. —(CH$_2$)$_5$O(CH$_2$)$_3$—C$_6$H$_5$ |
| 8. —(CH$_2$)$_2$O(CH$_2$)$_3$O—C$_6$H$_4$—OCH$_3$ |
| 9. —(CH$_2$)$_2$O(CH$_2$)$_3$O—C$_6$H$_4$—CF$_3$ |
| 10. —(CH$_2$)$_2$O(CH$_2$)$_2$—C$_6$H$_{11}$ |
| 11. —(CH$_2$)$_4$O—C$_6$H$_{11}$ |
| 12. —(CF$_2$)$_7$CF$_3$ |
| 13. —(CH$_2$)$_7$O(CF$_2$)$_7$CF$_3$ |
| 14. —CF$_2$CH$_2$O(CH$_2$)$_3$SCF$_3$ |
| 15. —(CH$_2$)$_4$S(CH$_2$)$_4$CF$_3$ |
| 16. —(CH$_2$)$_7$S(CH$_2$)$_2$SCF$_3$ |
| 17. —(CH$_2$)$_7$S(CH$_2$)$_2$SCH$_2$CF$_3$ |
| 18. —(CH$_2$)$_4$SCH$_2$—C$_6$H$_4$—OCF$_3$ |
| 19. —(CH$_2$)$_2$S(CH$_2$)$_3$O—C$_6$H$_4$—OCH$_3$ |
| 20. —(CH$_2$)$_2$O(CH$_2$)$_2$S—C$_6$H$_4$—CF$_3$ |

TABLE 7-continued

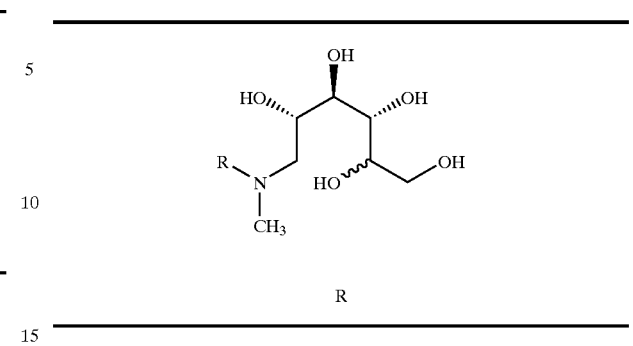

| R |
|---|
| 21. —(CH$_2$)$_2$S(CH$_2$)$_2$—C$_6$H$_{11}$ |
| 22. —(CH$_2$)$_4$S—C$_6$H$_{11}$ |

TABLE 8

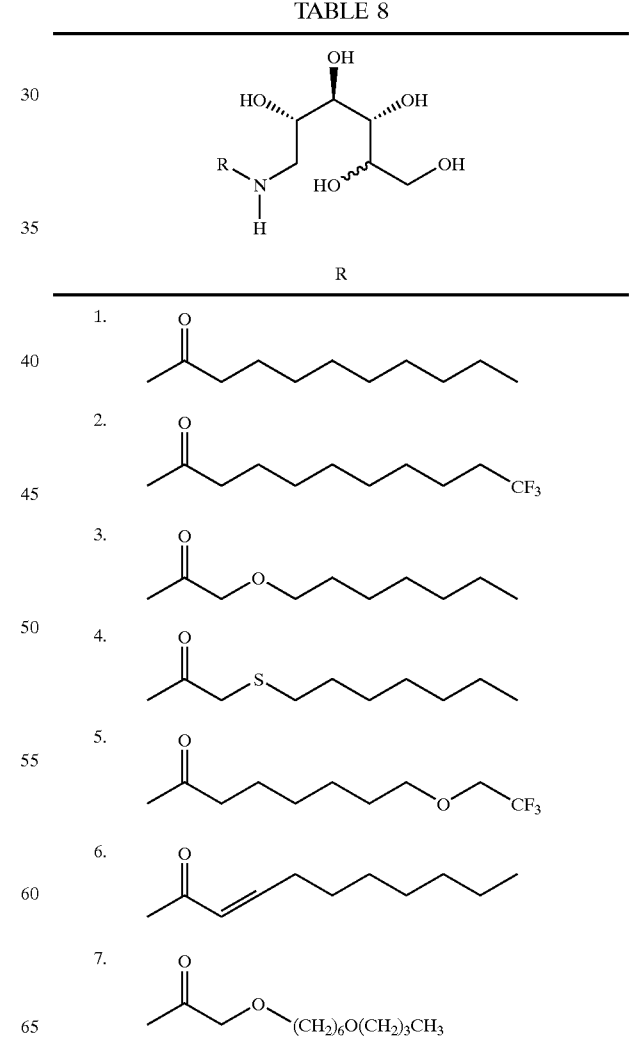

TABLE 8-continued

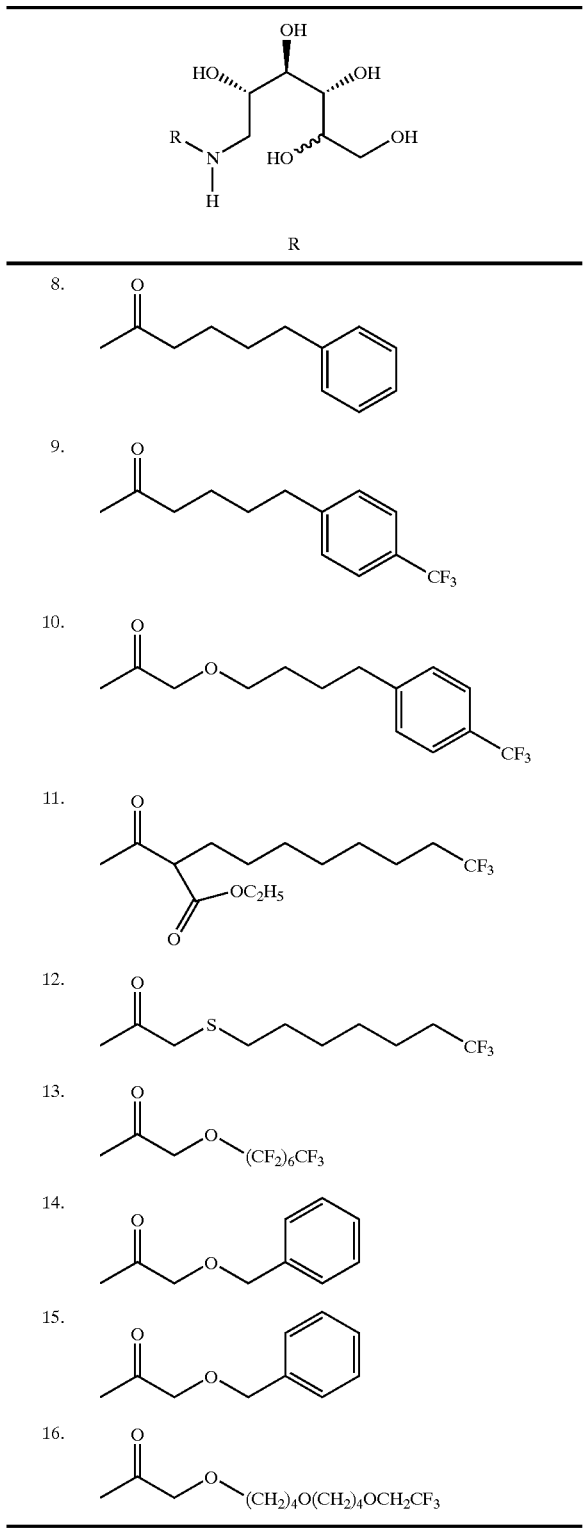

| | R |
|---|---|
| 8. | ![ketone with phenyl group] O, phenyl chain |
| 9. | ketone chain with -C6H4-CF3 |
| 10. | ketone-O-chain-C6H4-CF3 |
| 11. | branched ketone with OC2H5 ester and CF3 terminus |
| 12. | ketone-S-chain-CF3 |
| 13. | ketone-O-(CF2)6CF3 |
| 14. | ketone-O-CH2-phenyl |
| 15. | ketone-O-CH2-phenyl |
| 16. | ketone-O-(CH2)4O(CH2)4OCH2CF3 |

Among the substituents that may constitute R and/or $R^5$ in the compounds of Formula I, certain classes are preferred. A class of $R/R^5$ substituents which includes compounds of anti-hepatitis efficacy and compounds useful as intermediates in preparing therapeutic glucamines is the following:

TABLE 9

| | |
|---|---|
| aryloxyalkoxyalkyl, | alkynylcarbonyl, |
| alkylcarbonyloxyalkyl, | arylalkylcarbonyl, |
| arylcarbonyloxyalkyl, | aryloxyalkyl, |
| alkylcarbonylaminoalkyl, | aryloxyalkylcarbonyl, |
| arylcarbonylaminoalkyl, | haloalkylcarbonyl, |
| alkoxycarbonylaminoalkyl, | hydroxyalkylcarbonyl, |
| aminocarbonylaminoalkyl, | haloalkyloxyalkylcarbonyl, |
| aminothiocarbonylaminoalkyl, | cycloalkyl, |
| alkoxyalkyl, | cycloalkyloxyalkylcarbonyl, |
| hydroxyalkyl, | alkoxyalkylcarbonyl, |
| carboxyalkyl, | cycloalkylalkylcarbonyl, |
| alkoxycarbonylalkyl, | alkoxycarbonyl, |
| aminocarbonylalkyl, | alkylcarbonyl, |
| aminothiocarbonylalkyl, | aryloxyalkoxyalkylcarbonyl, |
| aminosulfonealkyl, | alkylcarbonyloxyalkylcarbonyl, |
| heterocycloalkyl, | arylcarbonyloxyalkylcarbonyl, |
| heteroaryloxyalkyl, | aminoalkylcarbonyl, |
| heteroarylthiaalkyl, | alkylcarbonylaminoalkylcarbonyl |
| heterocyclooxyalkyl, | arylcarbonylaminoalkylcarbonyl, |
| heterocyclothiaalkyl, | alkoxycarbonylaminoalkyl- |
| arylthiaalkyl, | carbonyl, |
| haloalkyl, | aminocarbonylaminoalkylcarbonyl, |
| haloalkyloxyalkyl, | aminothiocarbonylaminoalkyl- |
| carbonyl, | carbonyl, |
| cycloalkyloxyalkyl, | arylalkenylcarbonyl, |
| cycloalkylalkyloxyalkyl, | carboxyalkylcarbonyl, |
| alkenylcarbonyl, | alkoxycarbonylalkylcarbonyl, |
| aminocarbonylalkylcarbonyl, | heterocyclooxyalkylcarbonyl, |
| aminothiocarbonylalkylcarbonyl, | heterocyclothiaalkylcarbonyl, |
| aminosulfonealkylcarbonyl, | arylthiaalkylcarbonyl, |
| arylalkynylcarbonyl, | monohaloalkylcarbonyl, |
| heterocycloalkylcarbonyl, | haloalkyloxyalkylcarbonyl, |
| heteroarylalkyl, | cycloalkylalkyloxyalkylcarbonyl |
| heteroaryloxyalkyl, | |
| heteroarylthiaalkylcarbonyl, | |

Provided that not both of R and $R^5$ are hydrido, the glucamine compounds of Formula I comprising the substituents of Table 9 are believed to be novel compounds.

Another group of glucamine compounds believed to be novel are those in which both R and $R^5$ are selected from the following:

TABLE 10

| | |
|---|---|
| alkyl, | cycloalkylalkyloxyalkyl, |
| aminoalkyl, | alkenylcarbonyl, |
| arylcarbonylaminoalkyl, | alkynylcarbonyl, |
| alkenyl, | arylalkylcarbonyl, |
| alkynyl, | aryloxyalkylcarbonyl, |
| alkoxyalkyl, | haloalkylcarbonyl, |
| hydroxyalkyl, | hydroxyalkylcarbonyl, |
| arylalkyl, | haloalkyloxyalkylcarbonyl, |
| arylalkenyl, | cycloalkyl, |
| arylalkynyl, | cycloalkyloxyalkylcarbonyl, |
| heterocycloalkyl, | alkoxyalkylcarbonyl, |
| heteroarylalkyl, | cycloalkylalkylcarbonyl, |
| heteroaryloxyalkyl, | alkoxycarbonyl, |
| heteroarylthiaalkyl, | alkylcarbonyl, |
| heterocyclooxyalkyl, | aryloxyalkoxyalkylcarbonyl, |
| heterocyclothiaalkyl, | alkylcarbonyloxyalkylcarbonyl, |
| arylthiaalkyl, | arylcarbonyloxyalkylcarbonyl, |
| haloalkyl, | aminoalkylcarbonyl, |
| haloalkyloxyalkyl, | alkylcarbonylaminoalkylcarbonyl, |
| cycloalkyloxyalkyl, | arylcarbonylaminoalkylcarbonyl, |
| alkoxycarbonylaminoalkyl- | heterocycloalkylcarbonyl, |
| carbonyl, | heteroarylalkyl, |
| aminocarbonylaminoalkylcarbonyl, | heteroaryloxyalkyl, |
| aminothiocarbonylaminoalkyl- | heteroarylthiaalkylcarbonyl, |
| carbonyl, | heterocyclooxyalkylcarbonyl, |
| arylalkenylcarbonyl, | heterocyclothiaalkylcarbonyl, |
| carboxyalkylcarbonyl, | arylthiaalkylcarbonyl, |
| alkoxycarbonylalkylcarbonyl, | monohaloalkylcarbonyl, |
| aminocarbonylalkylcarbonyl, | haloalkyloxyalkylcarbonyl, |
| aminothiocarbonylalkylcarbonyl, | cycloalkylalkyloxyalkylcarbonyl |

TABLE 10-continued aminosulfonealkylcarbonyl,
arylalkynylcarbonyl,

Where either or both of R or $R^5$ is lower alkyl, R and $R^5$ are preferably not the same.

Other preferred glucamine compounds of this invention are those in which R is selected from the following substituents:

TABLE 11A

| | |
|---|---|
| aryloxyalkoxyalkyl, | carboxyalkyl, |
| alkylcarbonyloxyalkyl, | alkoxycarbonylalkyl, |
| alkyl, | aminocarbonylalkyl, |
| arylcarbonyloxyalkyl, | aminothiocarbonylalkyl, |
| aminoalkyl, | aminosulfonealkyl, |
| alkylcarbonylaminoalkyl, | arylalkynyl, |
| arylcarbonylaminoalkyl, | heterocycloalkyl, |
| alkoxycarbonylaminoalkyl, | heteroarylalkyl, |
| aminocarbonylaminoalkyl, | heteroaryloxyalkyl, |
| aminothiocarbonylaminoalkyl, | heteroarylthiaalkyl, |
| alkenyl, | heterocyclooxyalkyl, |
| alkynyl, | heterocyclothiaalkyl, |
| alkoxyalkyl, | aryloxyalkyl, |
| hydroxyalkyl, | arylthiaalkyl, |
| arylalkyl, | haloalkyl, |
| arylalkenyl, | haloalkyloxyalkyl, |
| carbonyl, | arylcarbonylaminoalkylcarbonyl, |
| cycloalkyloxyalkyl, | alkoxycarbonylaminoalkyl- |
| cycloalkylalkyloxyalkyl, | carbonyl, |
| alkenylcarbonyl, | aminocarbonylaminoalkylcarbonyl, |
| alkynylcarbonyl, | aminothiocarbonylaminoalkyl- |
| arylalkylcarbonyl, | carbonyl, |
| aryloxyalkyl, | arylalkenylcarbonyl, |
| aryloxyalkylcarbonyl, | carboxyalkylcarbonyl, |
| substituted aryloxyalkyl- | alkoxycarbonylalkylcarbonyl, |
| carbonyl, | aminocarbonylalkylcarbonyl |
| haloalkylcarbonyl, | aminothiocarbonylalkylcarbonyl, |
| hydroxyalkylcarbonyl, | aminosulfonealkylcarbonyl, |
| haloalkyloxyalkylcarbonyl, | arylalkynylcarbonyl, |
| cycloalkyloxyalkylcarbonyl, | heterocycloalkylcarbonyl, |
| alkoxyalkylcarbonyl, | heteroarylalkyl, |
| cycloalkylalkylcarbonyl, | heteroaryloxyalkyl, |
| alkoxycarbonyl, | heteroarylthiaalkylcarbonyl, |
| substituted alkylcarbonyl, | heterocyclooxyalkylcarbonyl, |
| aryloxyalkoxyalkylcarbonyl, | heterocyclothiaalkylcarbonyl, |
| alkylcarbonyloxyalkylcarbonyl, | arylthiaalkylcarbonyl, |
| arylcarbonyloxyalkylcarbonyl, | monohaloalkylcarbonyl, |
| aminoalkylcarbonyl, | haloalkyloxyalkylcarbonyl, |
| alkylcarbonylaminoalkylcarbonyl, | cycloalkylalkyloxyalkylcarbonyl |

TABLE 11B

| | |
|---|---|
| H, | arylalkyl, |
| alkyl, | aryloxyalkyl, |
| alkenyl, | cycloalkyl, |
| alkynyl, | cycloalkylalkyl, |
| alkoxyalkyl, | aryloxyalkyl, |
| haloalkyl, | cycloalkyloxyalkyl, |
| hydroxyalkyl, | cycloalkylalkyloxyalkyl |
| haloalkyloxyalkyl, | |

Additional groups of preferred R and/or $R^5$ substituents include the following:

(a) alkyl, aminoalkyl, alkenyl, alkynyl, alkoxyalkyl, arylalkyl, arylalkenyl, arylalkynyl, heterocycloalkyl, heteroarylalkyl, haloalkyl, haloalkyloxyalkyl, cycloalkyl, cycloalkylalkyl, cycloalkenyl, aryl, cycloalkenylalkyl, cycloalkylalkenyl, cycloalkylalkynyl, heterocycloalkenyl, heteroarylalkenyl, heteroarylalkynyl, hydroxyalkyl, haloalkoxyalkenyl, and haloalkoxyalkynyl;

(b) aryloxyalkoxyalkyl, alkylcarbonyloxyalkyl, arylcarbonyloxyalkyl, alkylcarbonylaminoalkyl, arylcarbonylaminoalkyl, alkoxycarbonylaminoalkyl, aminocarbonylaminoalkyl, aminothiocarbonylaminoalkyl, carboxyalkyl, aminocarbonylalkyl, aminothiocarbonylalkyl, aminosulfonealkyl, heteroaryloxyalkyl, heteroarylthiaalkyl, heterocyclooxyalkyl, heterocyclothiaalkyl, aryloxyalkyl, arylthiaalkyl, cycloalkyloxyalkyl, cycloalkylalkyloxyalkyl, cycloalkenylalkenyl, cycloalkenylalkynyl, aralkoxyalkyl, aralkoxyalkynyl, aralkenoxyalkyl, aralkenoxyalkenyl, aryloxyalkenyl, aryloxyalkynyl, hydroxyalkenyl, and hydroxyalkynyl;

(c) alkyl, alkenyl, alkynyl, alkoxyalkyl, arylalkyl, heterocycloalkyl, heteroarylalkyl, haloalkyl, haloalkyloxyalkyl, cycloalkyl, cycloalkylalkyl, cycloalkenyl, aryl, heterocycloalkenyl, heteroarylalkenyl, haloalkoxyalkenyl, and haloalkoxyalkynyl;

(d) aryloxyalkoxyalkyl, alkylcarbonylaminoalkyl, arylcarbonylaminoalkyl, aminocarbonylaminoalkyl, carboxyalkyl, aminocarbonylalkyl, aminosulfonealkyl, heteroaryloxyalkyl, heteroarylthiaalkyl, heterocyclooxyalkyl, heterocyclothiaalkyl, aryloxyalkyl, arylthiaalkyl, cycloalkyloxyalkyl, cycloalkylalkyloxyalkyl, aralkoxyalkyl, aralkenoxyalkyl, and aryloxyalkenyl;

(e) aryloxyalkoxyalkylcarbonyl, alkylcarbonyloxyalkylcarbonyl, alkylcarbonyl, arylcarbonyloxyalkylcarbonyl, aminoalkylcarbonyl, alkylcarbonylaminoalkylcarbonyl, arylcarbonylaminoalkylcarbonyl, alkoxycarbonylaminoalkylcarbonyl, aminocarbonylaminoalkylcarbonyl, aminothiocarbonylaminoalkylcarbonyl, alkenylcarbonyl, alkynylcarbonyl, alkoxyalkylcarbonyl, arylalkylcarbonyl, arylalkenylcarbonyl, carboxyalkylcarbonyl, aminocarbonylalkylcarbonyl, aminothiocarbonylalkylcarbonyl, aminosulfonealkylcarbonyl, arylalkynylcarbonyl, heterocycloalkylcarbonyl, heteroarylalkylcarbonyl, heteroaryloxyalkylcarbonyl, heteroarylthiaalkylcarbonyl, heterocyclooxyalkylcarbonyl, heterocyclothiaalkylcarbonyl, aryloxyalkylcarbonyl, arylthiaalkylcarbonyl, carbonyl, haloalkylcarbonyl, haloalkyloxyalkylcarbonyl, cycloalkyloxyalkylcarbonyl, cycloalkylalkyloxyalkylcarbonyl, cycloalkylcarbonyl, cycloalkylalkylcarbonyl, cycloalkenylcarbonyl, arylcarbonyl, cycloalkenylalkylcarbonyl, cycloalkenylalkenylcarbonyl, cycloalkenylalkynylcarbonyl, cycloalkylalkenylcarbonyl, cycloalkylalkynylcarbonyl, aralkoxyalkylcarbonyl, aralkoxyalkenylcarbonyl, aralkoxyalkynylcarbonyl, aralkenoxyalkylcarbonyl, aralkenoxyalkenylcarbonyl, heterocycloalkenylcarbonyl, heteroarylalkenylcarbonyl, heteroarylalkynylcarbonyl, aryloxyalkenylcarbonyl, aryloxyalkynylcarbonyl, hydroxyalkylcarbonyl, hydroxyalkenylcarbonyl, hydroxyalkynylcarbonyl, haloalkoxyalkenylcarbonyl, and haloalkoxyalkynylcarbonyl;

(f) alkylcarbonyl, aminoalkylcarbonyl, alkenylcarbonyl, alkynylcarbonyl, alkoxyalkylcarbonyl, arylalkylcarbonyl, arylalkenylcarbonyl, arylalkynylcarbonyl, heterocycloalkylcarbonyl, heteroarylalkylcarbonyl, haloalkylcarbonyl, haloalkyloxyalkylcarbonyl, cycloalkylcarbonyl, cycloalkylalkylcarbonyl, cycloalkenylcarbonyl, arylcarbonyl, cycloalkenylalkylcarbonyl, cycloalkylalkenylcarbonyl, cycloalkylalkynylcarbonyl, heterocycloalkenylcarbonyl, heteroarylalkenylcarbonyl, heteroarylalkynylcarbonyl, hydroxyalkylcarbonyl, haloalkoxyalkenylcarbonyl, and haloalkoxyalkynylcarbonyl;

(g) aryloxyalkoxyalkylcarbonyl, alkylcarbonyloxyalkylcarbonyl, arylcarbonyloxyalkylcarbonyl, alkylcarbonylaminoalkylcarbonyl, arylcarbonylaminoalkylcarbonyl, alkoxycarbonylaminoalkylcarbonyl, aminocarbonylaminoalkylcarbonyl, aminothiocarbonylaminoalkylcarbonyl, carboxyalkylcarbonyl, aminocarbonylalkylcarbonyl, aminothiocarbonylalkylcarbonyl, aminosulfonealkylcarbonyl, heteroaryloxyalkylcarbonyl, heteroarylthiaalkylcarbonyl, heterocyclooxyalkylcarbonyl, heterocyclothiaalkylcarbonyl, aryloxyalkylcarbonyl, arylthiaalkylcarbonyl, cycloalkyloxyalkylcarbonyl, cycloalkylalkyloxyalkylcarbonyl, cycloalkenylalkenylcarbonyl, cycloalkenylalkynylcarbonyl, aralkoxyalkylcarbonyl, aralkoxyalkenylcarbonyl, aralkoxyalkynylcarbonyl, aralkenoxyalkylcarbonyl, aralkenoxyalkenylcarbonyl, aryloxyalkenylcarbonyl, aryloxyalkynylcarbonyl, hydroxyalkenylcarbonyl, and hydroxyalkynylcarbonyl;

(h) alkylcarbonyl, carbonyl, alkenylcarbonyl, alkynylcarbonyl, alkoxyalkylcarbonyl, arylalkylcarbonyl, heterocycloalkylcarbonyl, heteroarylalkylcarbonyl, haloalkylcarbonyl, haloalkyloxyalkylcarbonyl, cycloalkylcarbonyl, cycloalkylalkylcarbonyl, cycloalkenylcarbonyl, arylcarbonyl, heterocycloalkenylcarbonyl, heteroarylalkenylcarbonyl, haloalkoxyalkenylcarbonyl, and haloalkoxyalkynylcarbonyl; and (i) aryloxyalkoxyalkylcarbonyl, alkylcarbonylaminoalkylcarbonyl, arylcarbonylaminoalkylcarbonyl, aminocarbonylaminoalkylcarbonyl, carboxyalkylcarbonyl, aminocarbonylalkylcarbonyl, aminosulfonealkylcarbonyl, heteroaryloxyalkylcarbonyl, heteroarylthiaalkylcarbonyl, heterocyclooxyalkylcarbonyl, heterocyclothiaalkylcarbonyl, aryloxyalkylcarbonyl, arylthiaalkylcarbonyl, cycloalkyloxyalkylcarbonyl, cycloalkylalkyloxyalkylcarbonyl, aralkoxyalkylcarbonyl, aralkenoxyalkylcarbonyl, and aryloxyalkenylcarbonyl.

Other preferred classes of $R/R^5$ substituents are those described as constituting the N-substituent of a 1,5-dideoxy-1,5-amino-D-glucitol compound in copending Ser. No. 09/503,945, filed Feb. 14, 2000 (now U.S. Pat. No. 6,545,021) (attorney's docket number SRL 6189) as also set forth hereinbelow. For example, to provide a compound, which in its free base form, is relatively strongly alkaline, it is advantageous for at least one of R and $R^5$ to be selected from among:

TABLE 12

| | |
|---|---|
| aryloxyalkoxyalkyl | carboxyalkyl |
| alkylcarbonyloxyalkyl | alkoxycarbonylalkyl |
| substituted alkyl | aminocarbonylalkyl |
| arylcarbonyloxyalkyl | aminothiocarbonylalkyl |
| aminoalkyl | aminosulfonealkyl |
| alkylcarbonylaminoalkyl | arylalkynyl |
| arylcarbonylaminoalkyl | heterocycloalkyl |
| alkoxycarbonylaminoalkyl | heteroarylalkyl |
| aminocarbonylaminoalkyl | heteroaryloxyalkyl |
| aminothiocarbonylaminoalkyl | heteroarylthiaalkyl |
| alkenyl | heterocyclooxyalkyl |
| arylalkenyl | heterocyclothiaalkyl |
| aryloxyalkyl | cycloalkyloxyalkyl |
| arylthiaalkyl | cycloalkylalkyloxyalkyl |
| monohaloalkyl | |
| haloalkyloxyalkyl | |

Salts of such compounds with strong pharmaceutically acceptable acids provide highly dissociable compounds that are effective in the method of the invention. Although the primary glucamine is also alkaline, it is generally preferred that at least one of R and $R^5$ not be hydrogen. More preferably, R and/or $R^5$ may be selected from among: substituted aryl, arylcarbonylaminoalkyl, aminocarbonylaminoalkyl, alkenyl, arylalkenyl, arylalkynyl, heterocycloalkyl, heteroarylalkyl, heteroaryloxyalkyl, heterocyclooxyalkyl, aryloxyalkyl, arylthiaalkyl, haloalkyloxyalkyl, cycloalkyloxyalkyl, cycloalkylalkyloxyalkyl and perhaloalkylaralkyl; of which substituted alkyl, alkenyl, arylalkenyl, heterocycloalkyl, heteroarylalkyl, heteroaryloxyalkyl, heterocyclooxyalkyl, aryloxyalkyl, haloalkyloxyalkyl and perhaloalkylaralkyl are particularly preferred, and alkenyl, arylalkenyl, heterocycloalkyl, heteroarylalkyl, aryloxyalkyl haloalkyloxyalkyl, perhaloalkylaralkyl and cycloalkyloxyalkyl.

However, amidoglucamine compounds of Formula I and pharmaceutically acceptable salts thereof are also useful in the treatment of hepatitis infections, or alternatively in the synthesis of other compounds of Formula I that are effective for such treatment. Thus, members of the following group of amido and other substituents may also serve effectively as the R or $R^5$ substituent or both in the compounds of Formula I:

TABLE 13

| | |
|---|---|
| carbonyl | arylcarbonylaminoalkylcarbonyl |
| alkenylcarbonyl | alkoxycarbonylaminoalkylcarbonyl |
| alkynylcarbonyl | aminocarbonylaminoalkylcarbonyl |
| arylalkylcarbonyl | aminothiocarbonylaminoalkyl- |
| aryloxyalkyl | carbonyl |
| aryloxyalkylcarbonyl | arylalkenylcarbonyl |
| substituted aryloxy- | carboxyalkylcarbonyl |
| alkylcarbonyl | alkoxycarbonylalkylcarbonyl |
| haloalkylcarbonyl | aminocarbonylalkylcarbonyl |
| hydroxyalkylcarbonyl | aminothiocarbonylalkylcarbonyl |
| haloalkyloxyalkylcarbonyl | aminosulfonealkylcarbonyl |
| cycloalkyloxyalkyl- | arylalkynylcarbonyl |
| carbonyl | heterocycloalkylcarbonyl |
| alkoxyalkylcarbonyl | heteroarylalkyl |
| cycloalkylalkylcarbonyl | heteroaryloxyalkyl |
| alkoxycarbonyl | heteroarylthiaalkylcarbonyl |
| substituted alkylcarbonyl | heterocyclooxyalkylcarbonyl |
| aryloxyalkoxyalkylcarbonyl | hetercyclothiaalkylcarbonyl |
| alkylcarbonyloxyalkylcarbonyl | arylthiaalkylcarbonyl |
| arylcarbonyloxyalkylcarbonyl | monohaloalkylcarbonyl |
| aminoalkylcarbonyl | haloalkyloxyalkylcarbonyl |
| alkylcarbonylaminoalkylcarbonyl | cycloalkylalkyloxyalkylcarbonyl |

More preferably, R may be selected from among: alkenylcarbonyl, arylalkylcarbonyl, haloalkylcarbonyl, haloalkyloxyalkylcarbonyl, cycloalkyloxyalkylcarbonyl, alkoxyalkylcarbonyl, cycloalkylalkylcarbonyl, substituted alkyl-carbonyl, aminoalkylcarbonyl, arylalkenylcarbonyl, aminosulfonealkylcarbonyl, arylalkynylcarbonyl, heterocycloalkylcarbony, heteroarylalkylcarbonyl, heteroaryloxyalkylcarbonyl, heterocyclooxyalkylcarbonyl, arylthiaalkylcarbonyl, haloalkyloxyalkylcarbonyl, cycloalkylalkyloxyalky; of which alkenylcarbonyl, arylalkylcarbonyl, haloalkylcarbonyl, haloalkyloxyalkylcarbonyl, cycloalkyloxyalkylcarbonyl, alkoxyalkylcarbonyl, cycloalkylalkylcarbonyl, substituted alkyl-carbonyl, aminoalkylcarbonyl, arylalkenylcarbonyl, heterocycloalkylcarbony, heteroarylalkylcarbonyl, heteroaryloxyalkylcarbonyl and haloalkyloxyalkylcarbonyl are particularly preferred, and arylalkylcarbonyl, haloalkylcarbonyl, haloalkyloxyalkylcarbonyl, cycloalkylalkylcarbonyl, aminoalkylcarbonyl and haloalkyloxycarbonyl.

Still other N-substituents which are preferred for purposes of potency, efficacy, formulation ability, toxicity and/or cost include:

TABLE 14

| aryloxyalkoxyalkyl | heteroarylalkyl |
| substituted alkyl | heteroaryloxyalkyl |
| aminoalkyl | heteroarylthiaalkyl |
| arylcarbonylaminoalkyl | heterocyclooxyalkyl |
| alkoxycarbonylaminoalkyl | heterocyclothiaalkyl |
| aminocarbonylaminoalkyl | aryloxyalkyl |
| alkenyl | arylthiaalkyl |
| arylalkenyl | monohaloalkyl |
| aminocarbonylalkyl | haloalkyloxyalkyl |
| aminosulfonealkyl | cycloalkyloxyalkyl |
| arylalkynyl | cycloalkylalkyloxyalkyl |
| heterocycloalkyl | |

Certain compounds of Formula I are novel compounds of this invention. Novel compounds of Formula I include compounds in which R is among the following:

TABLE 15

| aryloxyalkyl | substituted arylalkylcarbonyl |
| substitutedaryloxyalkyl | arylalkyloxycarbonyl |
| monohaloalkyl | aryloxyalkylcarbonyl |
| haloalkyloxyalkyl | substituted |
| carbonyl | aryloxyalkylcarbonyl |
| cycloalkyloxyalkyl | haloalkylcarbonyl |
| cycloalkylalkyloxyalkyl | hydroxyalkylcarbonyl |
| alkenylcarbonyl | haloalkyloxyalkylcarbonyl |
| alkynylcarbonyl | cycloalkyloxyalkylcarbonyl |
| arylalkylcarbonyl | alkoxyalkylcarbonyl |

Of the compounds of Table 15, the substituted alkyls are basic compounds which are advantageous in forming stable, water soluble, non-volatile pharmaceutically acceptable salts, preferably with strong acids. The carbonyl compounds of Table 15, like those of Table 13, are adapted for use either as antiviral therapeutic compounds or as intermediates for the preparation of other N-substituted-glucamine compounds of the invention and/or useful in the methods thereof. Of the carbonyl compounds of Table 15, arylalkylcarbonyl, aryloxyalkylcarbonyl, haloalkylcarbonyl, haloalkyloxyalkylcarbonyl, and cycloalkyloxyalkylcarbonyl are the more preferred.

Particularly preferred are compounds in which at least one of R and $R^5$ conforms to $R^7$ or $R^8$;, and especially compounds wherein R and/or $R^5$ is selected from among aryloxyalkyl, monooalkyl, haloalkyloxyalkyl, cycloalkyloxyalkyl, and cycloalkylalkyloxyalkyl. In another useful group of compounds, R and/or $R^5$ is selected from among alkenylcarbonyl, alkynylcarbonyl, arylalkylcarbonyl, substituted arylalkylcarbonyl, arylalkyloxycarbonyl, aryloxyalkylcarbonyl, substituted aryloxyalkylcarbonyl, haloalkylcarbonyl, hydroxyalkylcarbonyl, haloalkyloxyalkylcarbonyl, cycloalkyloxyalkylcarbonyl, and alkoxyalkylcarbonyl.

Compounds in which R or $R^5$ conforms to $R^7$ or $R^8$ are highly preferred, especially the ethers (where each of any of $X^1$ through $X^4$ are oxygen or sulfur, preferably oxygen), $R^1$ is alkyl or haloalkyl, and each of any of $R^2$ through $R^4$ is independently alkylene or haloalkylene. The di- and tri-ethers are particularly preferred, as are the $R^7/R^8$ substituents in which $R^1$ or $R^9$ is trifluoroalkyl.

Compounds in which A, B, C, and D are hydrido are particularly preferred for administration in the treatment of hepatitis infections. However, compounds with other combinations of A, B, C and D subsituents and configurations (including ring structures as described hereinabove) are useful as therapeutic agents and as intermediates for the synthesis of other compounds of Formula I. Where used as therapeutic agents, many of these substituted glucamines especially the esters and ethers, function as prodrugs.

Non-limiting illustrative preparation procedures are presented below in Examples 1 and 2 and Scheme 1 through and including Scheme 3.

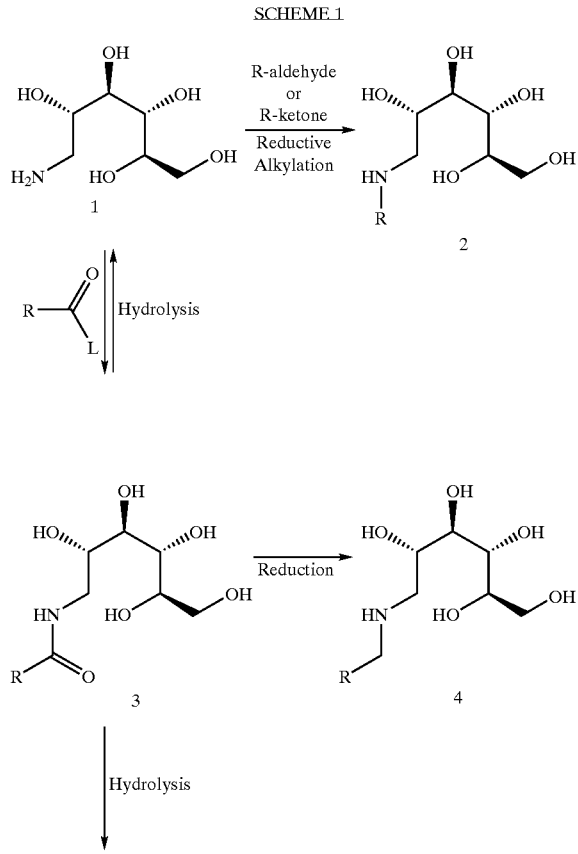

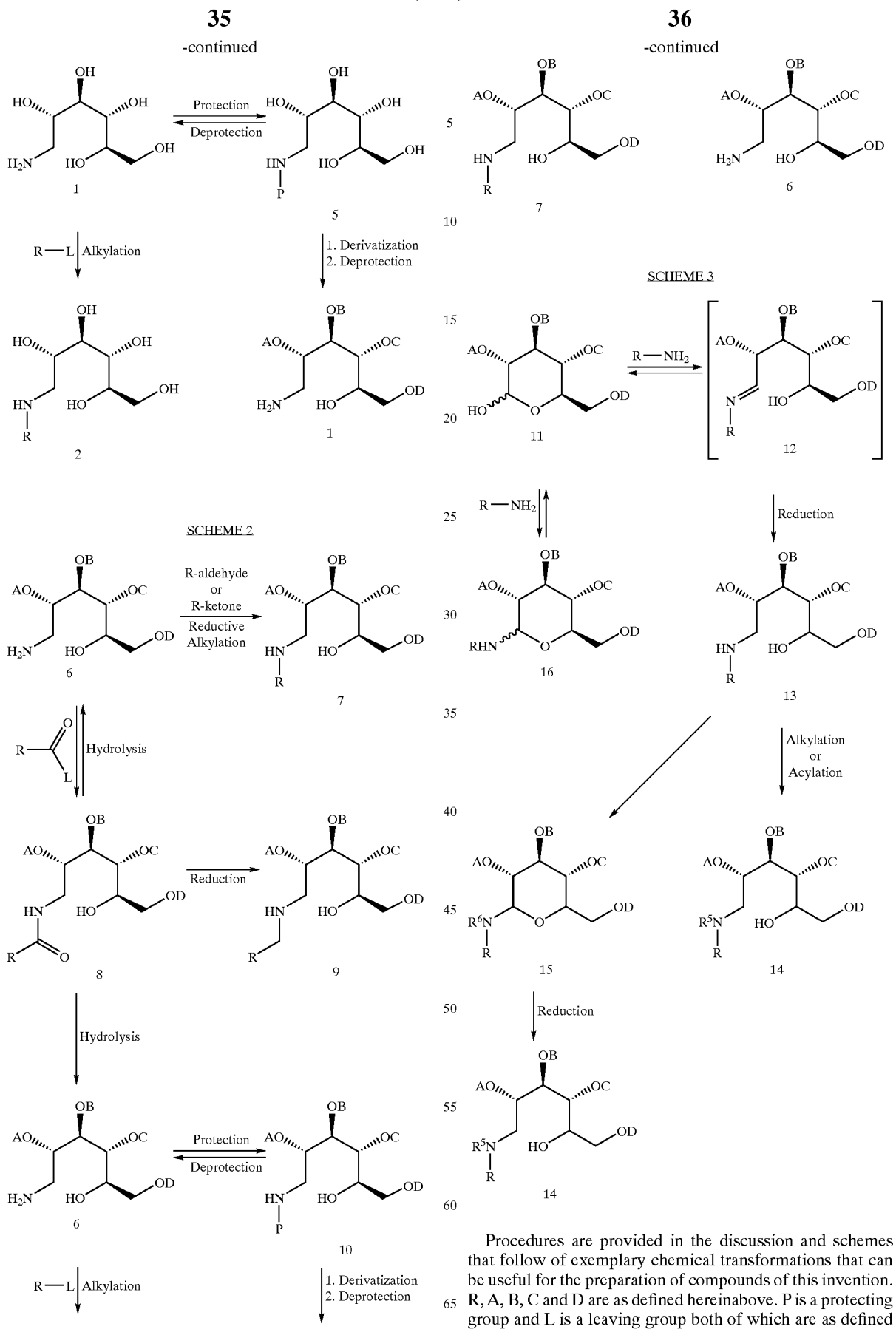
Procedures are provided in the discussion and schemes that follow of exemplary chemical transformations that can be useful for the preparation of compounds of this invention. R, A, B, C and D are as defined hereinabove. P is a protecting group and L is a leaving group both of which are as defined and in book by Green referenced below. These syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under ambient air.

In general, the choices of starting material and reaction conditions can vary as is well know to those skilled in the art. Usually, no single set of conditions is limiting because variations can be applied as required and selected by one skilled in the art. Conditions will also will be selected as desired to suit a specific purpose such as small scale preparations or large scale preparations. In either case, the use of less safe or less environmentally sound materials or reagents will usually be minimized. Examples of such less desirable materials are diazomethane, diethyl ether, heavy metal salts, dimethyl sulfide, some halogenated solvents, benzene and the like. In addition, many starting materials can be obtained from commercial sources from catalogs or through other arrangements.

Reaction media can be comprised of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, iso-propanol and the like.

Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like.

Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention 2,4,5,7, 9,10 and the like.

Room temperature or less or moderate warming (−10° C. to 60° C.) are the preferred temperatures of the synthesis and/or transformations of the compounds of this invention. If desired, the reaction temperature can range from about −78° C. to the reflux point of the reaction solvent or solvents. Colder temperatures such as that of liquid nitrogen may be desired on accasion especially if improved selectivity is required. Higher temperatures may also be used preferably in a pressure container system, i.e., a pressure bomb.

Examples of bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like.

Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N', N', -tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl, phenyl, butyl, iso-butyl, sec-butyl or tert-butyl lithium, sodium or potassium salts of dimethylsulfoxide, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents. Preferred base for use in the alkylation reaction is lithium diisopropyl amide as mentioned above.

A further use of bases is for the preparation of pharmaceutically acceptable salts discussed herein. These include those listed above with metal carbonates, bicarbonates, amines, quaternary amines, hydroxides and various polymeric bases being preferred.

Acids are used in many reactions during various synthesis and for the preparation of pharmaceutical salts. The Schemes as well as this discussion preparative methods illustrate acid use for the removal of the THP protecting group to produce a hydroxamic acid, removal of a tert-butoxy carbonyl group, hydroxylamine/ester exchange and the like. Acid hydrolysis of carboxylic acid protecting groups or derivatives is well known in the art. These methods, as is well known in the art, can use acid or acidic catalysts. The acid can be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like.

Salts of the compounds or intermediates of this invention are prepared in the normal manner wherein acidic compounds are reacted with bases such as those discussed above to produce metal or nitrogen containing cation salts. Basic compounds such as amines can be treated with an acid to form an amine salt. If the acid component of the salt is a weaker acid it is preferred that the base component be a stronger base. If the base component of the salt is with a weaker base it is preferred that the acid component be a stronger acid. Thus, the salts preferably have a relatively low pKa, preferably less than about 4.5. Most preferred are sales of relatively strongly basic imino sugars with strong acids. Pharmaceutically acceptable acids and bases for forming salts are well known in the art. Salts of the glucamines of this invention and anti-viral and anti-cancer nucleosides/ nucleotides are pharmaceutically acceptable salts.

Treatment of an amine in with an aldehyde or ketone under reducing conditions will produce a secondarry or tertiary amine of this invention such as 2, 7, 13, 14 or 15. Preferred solvents include, depending on the reducing agent, alcohols or tetrahydrofurane (THF). An inert atmosphere or dry atmosphere is used again depending upon the reactivity of the reducing agent. Hydrogen gas is the usual atmosphere for catalytic reductions. These reducing agents are well known in the art. Reductive alkylation is carried out by adding R—CHO to an amine such as DNJ and treating with a reducing agent such as sodium cyanoborohydride or carrying out a catalytic reduction with, for example, a metal catalyst and hydrogen gas. Such reducing agents are well known in the art and include such reagents as borane, borane:THF, borane:pyridine, lithium aluminum hydride, aluminum hydride, lithium borohydride, sodium borohydride potassium triacetylborohydride and the like. Alternatively, reductive alkylation can be carried out under hydrogenation conditions in the presence of a metal catalyst. Catalysts, hydrogen pressures and temperatures are discussed and are well known in the art. A desirable "hydride type" reductive alkylation catalyst is borane:pyridine complex. Reductive alkylation or hydrogenation's can be carried out at atmospheric pressure and higher pressures can be used if desired. Catalysts include, for example, Pd, Pd on Carbon, Pt, $PtO_2$ and the like. Less robust catalysts (deactivated) include such thing as Pd on $BaCO_3$ or Pd with quinoline or/and sulfur can be used in situations wherein selectivity is desired.

Acylation of substrates 1, 6, or 13, as shown in the reaction schemes set out above, can be carried out in standard fashion wherein the amine is treated with a carbonyl compound with a leaving group attached as is discussed in textbooks of organic chemistry. The leaving group is designated as "L" in the Schemes and may be different in the case of, for example, carboxylic acid derivatives, $SN_2$ substrates and $SN_1$ substrates and the addition-elimination process with carbonyl type compounds. Well know acylating groups including those with leaving groups include halides, anhydrides, mixed anhydrides, ketenes as well as exchangeable groups such as ester groups. Coupling with an activated ester synthesized in situ is also a useful process for preparing amides and it is discussed below. For example, compound 1, 4, 6, 7, or 13 is treated with an acid chloride in the presence of, preferably, a tertiary amine base under an inert atmosphere at between about −10° C. and 0° C. The product of this reaction is an amide 3 or 8 of this invention. A preferred acid activating group (L) is the chloride prepared by, for example, reaction of an acid with oxalyl chloride, phosphorus trichloride and the like. These carboxylic acids can be derivatized with protecting group or hydrolyzed to the acid as required.

Compounds 3, 8 or 15 are reduced to produce 4 or 9, respectively, as a products of this invention. The reduction is carried out using procedures and reagents as discussed hereinabove and other methods as indicated. Reduction of amides is well known in the art.

Amides such as 3, 8, 13, 14 or 15 can be hydrolyzed if desired. Base hydrolysis or acid hydrolysis methods are well known and the choice of systems will depend upon factors determined by the chemist. For example, the presence of base labile substituents might cause a scientist to select an acid hydrolysis process. Bases that can be used are listed herein. Acids are also discussed above and hydrogen chloride, toluenesulfonic acid and trifluoroacetic acid being preferred. Acid catalyzed exchange processes are also useful for converting compound 3 or 8 into other analogs or into 1 or 6.

Compounds 1, 4, 6, 7, or 13 are also able to be protected as is shown by the preparation of 5, 10, 14 and 15, respectively. The group P in, for example, 5, 10, 14 and 15, is a special case of R wherein the group may be useful for treating disease and also useful for the preparation of other compounds of this invention. Protecting groups, P, are well know in organic chemistry along with protection/ deprotection processes. They are frequently used to control reaction sites, reaction selectivities, help with resolutions such as optical resolutions, aid in purification processes and prevent over reaction in preparation processes. It should be noted that protection of groups other than nitrogen is common in the art with non-limiting examples being hydroxyl groups, thiol groups, carbonyl groups, phosphorus groups, silicon groups and the like and that P is used to indicate protecting groups in these cases also. It should also be noted that protecting groups and protection/deprotection reaction sequences are well know in the art of natural product chemistry including sugar chemistry and amino acid/peptide chemistry. Editions of the books by Thedora Green, e.g., Green, T., *Protecting Groups in Organic Chemistry*, Second ed., John Wiley & Sons, New York (1991), are useful in this regard and are incorporated herein by reference.

As mentioned above, contemplated compounds can include compounds wherein a nitrogen of an amine is acylated to provide, for example, amino acid carbamates. Non-limiting examples of these carbamates are the carbobenzoxycarbonyl (Z, CBZ, benzyloxycarbonyl), isobutoxycarbonyl and tert-butoxycarbonyl (BOC, t-BOC) compounds. The materials can be made at various stages in the synthesis based on the needs and decisions made by a person skilled in the art using methods well know in the art.

Useful synthetic techniques and reagents for the preparation of the compounds of this invention include those used in protein, peptide and amino acid synthesis, coupling and transformation chemistry. The use of the tert-butoxycarbonyl (BOC) and benzyloxycarbonyl (Z) as will as their synthesis and removal are examples of such protection or synthesis schemes. This includes, for example, active ester or mixed anhydride couplings wherein preferred bases, if required, are tertiary amines such as N-methylmorpholine. Reagents for protection of the amine group of the protected amino acids include carbobenzoxy chloride, iso-butylchloroformate, tert-butoxycarbonyl chloride, di-tert-butyl dicarbonate and the like which are reacted with the amine in non-protic or dipolar aprotic solvents such as DMF or THF or mixtures of solvents.

Removal of protecting groups on nitrogen, oxygen, sulfur or other groups such as carbamates, silyl groups, THP ethers, enol ethers, ketals, acetals, hemiacetals, hemi-ketals, methoxymethyl ethers, benzyl, p-methoxybenzyl, or other substituted benzyl groups; acyl or aroyl groups or diphenylmethyl (benzhydryl) or triphenylmethyl (trityl) can be carried out at different stages in the synthesis of the compounds of this invention as required by methods selected by one skilled in the art. These methods are well known in the art including the amino acid, amino acid coupling, peptide synthesis, peptide mimetic synthesis art. Removal methods can include catalytic hydrogenation, base hydrolysis, carbonyl addition reactions, acid hydrolysis, exchange and the like. Both the preparation and removal of protecting groups, for example, carbamates, trifluoroacetate groups, benzyl groups and/or substituted arylalkyl groups is discussed in Green, T., *Protecting Groups in Organic Chemistry*, Second ed., John Wiley & Sons, New York (1991) as discussed above. A preferred method of removal of a BOC group is HCl gas in methylene chloride which, following normal workup, provides directly an HCl salt of an amine of this invention, i.e., an ammoniun salt. A preferred method of removing a Z group is catalpetic reduction.

Alkylation of amines such as 1, 4, 6, 7, 9, 13 or 14 is accomplished by methods well known in the art and discussed in textbooks of organic chemistry. The process is via $SN_2$ or $SN_1$ displacement of a leaving group, L, on a substrate by the amine. The amine is treated in a solvent such as those discussed above like DMSO, DMF, methanol, ethanol, THF, acetone and the like. Leaving groups can include halides, sulfonic acid esters such as tosylates, mesylates, triflates, trifluoroacetates and the like. The reaction can be carried out under an inert atmosphere or dry, non-oxidative conditions. An inert atmosphere is preferred.

Scheme 2 illustrates the application of the methods discussed for the preparation of compounds wherein A, B, C and D are hydrogen. It is to be noted that the syntheses may proceed in the presence of the hydroxyl groups thus the chemist has options in selecting the compound to be synthesized as well as the synthetic route to the compound.

Scheme 3 illustrates the preparation of open chain sugars containing amines 13, 14, or 15, amides 14 and 15 or protected amines 15 and 14 and imine 12. The reductive alkylation, hydrolysis, reduction, protection, deprotection, and alkylation processes have been discussed above. The interconversion of, for example, hydroxyl groups can be carried out by alkyation or acylation by processes discussed above and well know in the art. Treatment with an aldehyde, aldimine, ketone or ketimine under, for example, acid contitions in a non-protic or dipolar aprotic solvent, produces heterocycles such as those presented above.

Scheme 3 illustrates the used of glucose, sorbose other open chain sugars and their derivatives in the preparation of 2. For example, glucose is reacted with a primary amine R—$NH_2$ or a derivative of the R group in R—$NH_2$ to produce a putative imine derivative 12. R is as defined above (including hydrogen with the use of ammonia) and preferably not connected via a carbonyl carbon. Reaction can be with or without heating and with or without a catalyls such as an acid catalyst. Removal of water during imine formation from the putative open chain aldehyde intermediate is possible if desired. Reduction using methods discussed above including metal catalyzed hydrogenations produce the open chain compound 13.

Compounds of the present invention can possess one or more asymmetric carbon atoms and are thus capable of existing in the form of optical isomers such as enantiomers, racemates and diastereoisomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base.

Examples of appropriate acids are tartaric, diacetyltartaric, dibenzoyltartaric, ditoluoyltartaric, natural aminoacids and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient since the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention. Examples include cis isomers, trans isomers, E isomers, Z isomers, syn- isomers, anti- isomers, tautomers, rotamers and the like. Aryl, heterocyclo or heteroaryl tautomers, heteroatom isomers, heterocyclo or heteroaryl heteroatom isomers and ortho, meta or para substitution isomers are also included as isomers as are multicyclic isomers such as those of the phenanthrene/anthracene type and the multicyclic saturated or partially unsaturated type. The latter type of isomer is exemplified in general by bicyclo[2,2,2]octane and bicyclo[3,2,1]octane. Solvates or solvent addition compounds such as hydrates or alcoholates are also specifically included both as chemicals of this invention and in, for example, formulations or pharmaceutical compositions for drug delivery.

Where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

The chemical reactions described above are generally disclosed in terms of their broadest application to the preparation of the compounds of this invention. Occasionally, the reactions can not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Other compounds of this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Prodrugs are drugs that can be chemically converted in vivo or in vitro by biological systems into an active drug or drugs, i.e., it is a pharmaceutically acceptable bioprecursor of a desired pharmaceutical or pharmaceuticals. The prodrug can be a compound having a structural formula different from the active compound but which upon administration to a mammal or in vitro system is converted into a compound of this invention. Such prodrugs are also compounds of this invention useful for the treatment of human, agricultural and general veterinary diseases.

In treating hepatitis B virus or hepatits C virus infections, one can use the present substitututed-glucamine compounds alone or in combination in the form of salts derived from inorganic or organic acids. These salts include but are not limited to the following: acetate, adipate, alginate,

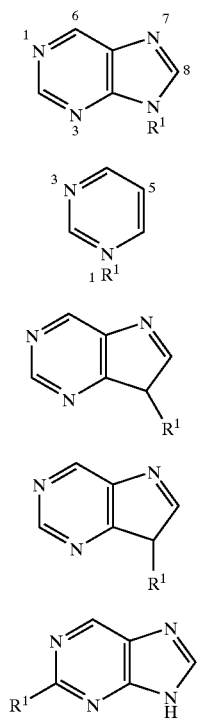

citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others. Water- or oil-soluble or dispersible products are thereby obtained as desired. The salts are formed by combining the basic compounds with the desired acid.

Nucleosides and Nucleotides

Nucleosides and nucleotides useful in the present invention are purine (II) base compounds or pyrimidine (III) base compounds, or analogs such as compounds IV, V or VI.

Position numbering for purines and pyrmidines is as shown in structures II and III. $R^1$ can be selected from hydroxyalkyl, hydroxyalkenyl, carboxyalkyl, carboxyalkenyl, thiolalkyl, alkylthioalkyl, alkoxyalkyl, alkoxyalkenyl, heterocycle, heterocyclo-alkyl, hydroxyalkylalkoxyalkyl, alkoxyalkylalkoxyalkyl, and cycloalkylalkyl. The purine compounds can be further substituted at positions 1, 2, 3, 6, 7, or 8 of the purine heterocycle, and the pyrimidine compounds can be substituted at positions 2, 3, 4, 5, or 6 of the pyrimidine heterocycle. Such substituents can be selected from hydroxy, alkoxy, halo, thiol, amino, carboxyl, mono-substituted amino, di-substituted amino, and alkyl.

The following definitions are applicable only to the structures of Formulas II, III, IV, V and VI of this invention. When used in combination with another radical when referring to the purines and pyrimidines useful in the present invention, the term "alkyl" means a straight or branched chain hydrocarbon radical containing from 1 to 8 carbon atoms, preferably 1 to 4 carbon atoms. When used in combination with another radical, the term "alkenyl" means a straight or branched chain hydrocarbon radical having 1 or more double bonds, containing from 2 to 8 carbon atoms, preferably 1 to 4 carbon atoms. When used alone when referring to purines and pyrimidines useful in the present invention, the term "alkyl" means a straight or branched chain alkyl radical containing from six to 14 carbon atoms, preferably seven to 12 carbon atoms, and most preferably eight to 11 carbon atoms. The term "aryl" alone or in combination with another radical means a phenyl, naphthyl, or indenyl ring, optionally substituted with one or more substituents selected from alkyl, alkoxy, halogen, hydroxy, or nitro. "Alkanoyl" means branched or straight chain alkanecarbonyl having a chain length of $C_1$ to $C_{20}$, preferably $C_2$ to $C_{14}$, more preferably $C_4$ to $C_{10}$; "aroyl" means arylcarbonyl; and "trifluoroalkanoyl", means alkyl containing three fluoro substituents. "Halogen" means fluorine, chlorine, bromine, or iodine. "Thiol" means sulfur substituted with hydrogen (—SH). "Amino" means nitrogen with two hydrogen atoms; "monosubstituted amino" and "disubstituted amino" mean amino groups further independently substituted with one or more alkyl or arylalkyl groups. "Hydroxyalkyl" means an alkyl group substituted with one or more hydroxyl groups; "hydroxy-alkenyl" means an alkenyl group substituted with one or more hydroxyl groups; "thioalkyl" means an alkyl substituted with one or more thiol (SH) groups; "alkoxyalkyl" means an alkyl substituted with one or more alkyl ether groups; "alkoxyalkenyl" means an alkenyl group substituted with one or more alkyl ether groups; "hydroxyalkylalkoxyalkyl" means an alkoxyalkyl group substituted with a hydroxyalkyl group; "alkoxyalkylalkoxyalkyl" means an alkoxyalkyl group substituted with an alkoxyalkyl group; "cycloalkylalkyl" means an alkyl group substituted with a cycloalkyl group. The term "heterocycle," alone or in combination, means a saturated or partially unsaturated 5 or 6-membered ring containing one or more oxygen, nitrogen, and/or sulfur heteroatoms. Said heterocycle can further be substituted with one to four substituents, which can be independently, hydroxy, hydroxyalkyl, thiol, alkoxy, azido, nitro, a halogen atom, amino, mono-substituted amino, or disubstituted amino. Heterocycloalkyl means an alkyl group wherein one or more hydrogen atoms are replaced by a substituted or unsubstituted heterocyclic ring.

Also included are the tautomers of the substituents on the compounds of the invention. Non-limiting examples of tautomers are ketone/enol tautomers, imino/amino tautomers, N-substituted imino/N-substituted amino tautomers, thiol/thiacarbonyl tautomers, and ring-chain tautomers such as the five and six membered ring oxygen, nitrogen, sulfur, or oxygen- and sulfur- containing heterocycles also containing substituents alpha to the heteroatoms. Also specifically included in the present invention are enantiomers and diastereomers, as well as racemates and isomeric mixtures of the compounds discussed herein.

Representative nucleoside and nucleotide compounds useful in the present invention include, but are not limited to:

(+)-cis-5-fluoro-1-[2-(hydroxy-methyl)-[1,3-oxathiolan-5-yl]cytosine;
(−)-2'-deoxy-3'thiocytidine-5'-triphosphate (3TC);
(−)-cis-5-fluoro-1-[2-(hydroxy-methyl)-[1,3-oxathiolan-5-yl]cytosine (FTC);
(−)2',3', dideoxy-3'-thiacytidine [(−)-SddC];
1-(2'-deoxy-2'-fluoro-beta-D-arabinofuranosyl)-5-iodocytosine (FIAC);
1-(2'-deoxy-2'-fluoro-beta-D-arabinofuranosyl)-5-iodocytosine triphosphate (FIACTP);
1-(2'-deoxy-2'-fluoro-beta-D-arabinofuranosyl)-5-methyluracil (FMAU);
1-beta-D-ribofuranosyl-1,2,4-triazole-3-carboxamide;
2',3'-dideoxy-3'-fluoro-5-methyl-dexocytidine (FddMeCyt);
2',3'-dideoxy-3'-chloro-5-methyl-dexocytidine (ClddMeCyt);
2',3'-dideoxy-3'-amino-5-methyl-dexocytidine (AddMeCyt);
2',3'-dideoxy-3'-fluoro-5-methyl-cytidine (FddMeCyt);
2',3'-dideoxy-3'-chloro-5-methyl-cytidine (ClddMeCyt);
2',3'-dideoxy-3'-amino-5-methyl-cytidine (AddMeCyt);
2',3'-dideoxy-3'-fluorothymidine (FddThd);
2',3'-dideoxy-beta-L-5-fluorocytidine (beta-L-FddC);
2',3'-dideoxy-beta-L-5-thiacytidine;
2',3'-dideoxy-beta-L-5-cytidine (beta-L-ddC);
9-(1,3-dihydroxy-2-propoxymethyl)guanine;
2'-deoxy-3'-thia-5-fluorocytosine;
3'-amino-5-methyl-dexocytidine (AddMeCyt);
2-amino-1,9-[(2-hydroxymethyl-1-(hydroxymethyl)ethoxyl methyl]-6H-purin-6-one (gancyclovir);
2-[2-(2-amino-9H-purin-9y)ethyl]-1,3-propandil diacetate (famciclovir);
2-amino-1,9-dihydro-9-[(2-hydroxy-ethoxy)methyl]6H-pur in-6-one (acyclovir);
9-(4-hydroxy-3-hydroxymethyl-but-1-yl)guanine (penciclovir);
9-(4-hydroxy-3-hydroxymethyl-but-1-yl)-6-deoxy-guanine diacetate (famciclovir);
3'-azido-3'-deoxythymidine (AZT);
3'-chloro-5-methyl-dexocytidine (ClddMeCyt);
9-(2-phosphonyl-methoxyethyl)-2',6'-diaminopurine-2',3'-dideoxyriboside;
9-(2-phosphonylmethoxyethyl)adenine (PMEA);
acyclovir triphosphate (ACVTP);
D-carbocyclic-2'-deoxyguanosine (CdG);
dideoxy-cytidine;
dideoxy-cytosine (ddC);
dideoxy-guanine (ddG);
dideoxy-inosine (ddI);
E-5-(2-bromovinyl)-2'-deoxyuridine triphosphate;
fluoro-arabinofuranosyl-iodouracil;
1-(2'-deoxy-2'-fluoro-1-beta-D-arabinofuranosyl)-5-iodo-uracil (FIAU);
stavudine;
9-beta-D-arabinofuranosyl-9H-purine-6-amine monohydrate (Ara-A);
9-beta-D-arabinofuranosyl-9H-purine-6-amine-5'-monopho sphate monohydrate (Ara-AMP);
2-deoxy-3'-thia-5-fluorocytidine;
2',3'-dideoxy-guanine; and
2',3'-dideoxy-guanosine.

A preferred compound is (−)-2'-deoxy-3'-thiocytidine-5'-triphosphate (3TC).

Synthetic methods for the preparation of nucleosides and nucleotides useful in the present invention are likewise well known in the art as disclosed in Acta Biochim. Pol., 43, 25–36 (1996); Swed. Nucleosides Nucleotides 15, 361–378 (1996), Synthesis 12, 1465–1479 (1995), Carbohyd. Chem. 27, 242–276 (1995), Chem. Nucleosides Nucleotides 3, 421–535 (1994), Ann. Reports in Med. Chem., Academic Press; and Exp. Opin. Invest. Drugs 4, 95–115 (1995).

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily preparable from known starting materials.

While nucleoside analogs are generally employed as antiviral agents as is, nucleotides (nucleoside phosphates) must sometimes have to be converted to nucleosides in order to facilitate their transport across cell membranes. An example of a chemically modified nucleotide capable of entering cells is S-1-3-hydroxy-2-phosphonylmethoxypropyl cytosine (HPMPC, Gilead Sciences).

Nucleoside and nucleotide compounds of this invention that are acids can form salts. Examples include salts with alkali metals or alkaline earth metals, such as sodium, potassium, calcium, or magnesium, or with organic bases or basic quaternary ammonium salts.

Immunomodulators and Immunostimulants

A large number of immunomodulators and immunostimulants that can be used in the methods of the present invention are currently available. A list of these compounds is provided in Table 1, below.

TABLE 1

AA-2G
adamantylamide dipeptide
adenosine deaminase, Enzon
adjuvant, Alliance
adjuvants, Ribi
adjuvants, Vaxcel
Adjuvax
agelasphin-11
AIDS therapy, Chiron
algal glucan, SRI
algammulin, Anutech
Anginlyc
anticellular factors, Yeda
Anticort
antigastrin-17 immunogen, Ap
antigen delivery system, Vac
antigen formulation, IDBC
antiGnRH immunogen, Aphton
Antiherpin
Arbidol
azarole
Bay-q-8939
Bay-r-1005
BCH-1393
Betafectin
Biostim
BL-001
BL-009
Broncostat
Cantastim
CDRI-84-246
cefodizime
chemokine inhibitors, ICOS
CMV peptides, City of Hope
CN-5888
cytokine-releasing agent, St
DHEAS, Paradigm
DISC TA-HSV
J07B
I01A
I01Z
ditiocarb sodium
ECA-10-142
ELS-1
endotoxin, Novartis
FCE-20696
FCE-24089
FCE-24578
FLT-3 ligand, Immunex
FR-900483
FR-900494
FR-901235
FTS-Zn
G-proteins, Cadus
gludapcin
glutaurine
glycophosphopeptical
GM-2
GM-53
GMDP
growth factor vaccine, EntreM
H-BIG, NABI
H-CIG, NABI
HAB-439
Helicobacter pylori vaccine,
herpes-specific immune factor
HIV therapy, United Biomed
HyperGAM+CF
ImmuMax
Immun BCG
immune therapy, Connective
immunomodulator, Evans
immunomodulators, Novacell
imreg-1
imreg-2
Indomune TABLE 1-continued inosine pranobex
interferon, Dong-A (alpha2)
interferon, Genentech (gamma)
interferon, Novartis (alpha)
interleukin-12, Genetics Ins
interleukin-15, Immunex
interleukin-16, Research Cor
ISCAR-1
J005X
L-644257
licomarasminic acid
LipoTher
LK-409
LK-410
LP-2307
LT (R1926)
LW-50020
MAF, Shionogi
MDP derivatives, Merck
met-enkephalin, TNI
methylfurylbutyrolactones
MIMP
mirimostim
mixed bacterial vaccine, Tem
MM-1
moniliastat
MPLA, Ribi
MS-705
murabutide
murabutide, Vacsyn
muramyl dipeptide derivative
muramyl peptide derivatives
myelopid
N-563
NACOS-6
NH-765
NISV, Proteus
NPT-16416
NT-002
PA-485
PEFA-814
peptides, Scios
peptidoglycan, Pliva
Perthon, Advanced Plant
PGM derivative, Pliva
Pharmaprojects No. 1099
Pharmaprojects No. 1426
Pharmaprojects No. 1549
Pharmaprojects No. 1585
Pharmaprojects No. 1607
Pharmaprojects No. 1710
Pharmaprojects No. 1779
Pharmaprojects No. 2002
Pharmaprojects No. 2060
Pharmaprojects No. 2795
Pharmaprojects No. 3088
Pharmaprojects No. 3111
Pharmaprojects No. 3345
Pharmaprojects No. 3467
Pharmaprojects No. 3668
Pharmaprojects No. 3998
Pharmaprojects No. 3999
Pharmaprojects No. 4089
Pharmaprojects No. 4188
Pharmaprojects No. 4451
Pharmaprojects No. 4500
Pharmaprojects No. 4689
Pharmaprojects No. 4833
Pharmaprojects No. 494
Pharmaprojects No. 5217
Pharmaprojects No. 530
pidotimod
pimelautide
pinafide
PMD-589
podophyllotoxin, Conpharm
POL-509
poly-ICLC
poly-ICLC, Yamasa Shoyu TABLE 1-continued PolyA-PolyU
Polysaccharide A
protein A, Berlox Bioscience
PS34WO
pseudomonas MAbs, Teijin
Psomaglobin
PTL-78419
Pyrexol
pyriferone
Retrogen
Retropep
RG-003
Rhinostat
rifamaxil
RM-06
Rollin
romurtide
RU-40555
RU-41821
rubella antibodies, ResCo
S-27609
SB-73
SDZ-280-636
SDZ-MRL-953
SK&F-107647
SL04
SL05
SM-4333
Solutein
SRI-62-834
SRL-172
ST-570
ST-789
staphage lysate
Stimulon
suppressin
T-150R1
T-LCEF
tabilautide
temurtide
Theradigm-HBV
Theradigm-HPV
Theradigm-HSV
THF, Pharm & Upjohn
THF, Yeda
thymalfasin
thymic hormone fractions
thymocartin
thymolymphotropin
thymopentin
thymopentin analogues
thymopentin, Peptech
thymosin fraction 5, Alpha
thymostimulin
thymotrinan
TMD-232
TO-115
transfer factor, Viragen
tuftsin, Selavo
ubenimex
Ulsastat
ANGG-
CD-4+
Collag+
COLSF+
COM+
DA-A+
GAST-
GF-TH+
GP-120-
IF+
IF-A+
IF-A-2+
IF-B+
IF-G+
IF-G-1B+
IL-2+
IL-12+
IL-15+

TABLE 1-continued

IM+
LHRH-
LIPCOR+
LYM-B+
LYM-NK+
LYM-T+
OPI+
PEP+
PHG-MA+
RNA-SYN-
SY-CW-
TH-A-1+
TH-5+
TNF+
UN

The substituted glucamine compounds useful in the present invention can be administered to humans in an amount in the range of from about 0.1 mg/kg/day to about 100 mg/kg/day, more preferably from about 1 mg/kg/day to about 75 mg/kg/day, and most preferably from about 5 mg/kg/day to about 50 mg/kg/day.

The nucleoside or nucleotide antiviral compound, or mixtures thereof, can be administered to humans in an amount in the range of from about 0.1 mg/person/day to about 500 mg/person/day, preferably from about 10 mg/person/day to about 300 mg/person/day, more preferably from about 25 mg/person/day to about 200 mg/person/day, even more preferably from about 50 mg/person/day to about 150 mg/person/day, and most preferably in the range of from about 1 mg/person/day to about 50 mg/person/day.

Immunomodulators and immunostimulants useful in the present invention can be administered in amounts lower than those conventional in the art. For example, thymosin alpha 1 and thymosin fraction 5 are typically administered to humans for the treatment of HepB infections in an amount of about 900 g/m$^2$, two times per week (Hepatology (1988) 8:1270; Hepatology (1989) 10:575; Hepatology (1991) 14:409; Gastroenterology (1995) 108:A1127). In the methods and compositions of the present invention, this dose can be in the range of from about 10 g/m$^2$, two times per week to about 750 g/m$^2$, two times per week, more preferably from about 100 g/m$^2$, two times per week to about 600 g/m$^2$, two times per week, most preferably from about 200 g/m$^2$, two times per week to about 400 g/m$^2$, two times per week. Interferon alfa is typically administered to humans for the treatment of HepC infections in an amount of from about $1\times10^6$ units/person, three times per week to about $10\times10^6$ units/person, three times per week (Simon et al., (1997) Hepatology 25:445–448). In the methods and compositions of the present invention, this dose can be in the range of from about $0.1\times10^6$ units/person, three times per week to about $7.5\times10^6$ units/person, three times per week, more preferably from about $0.5\times10^6$ units/person, three times per week to about $5\times10^5$ units/person, three times per week, most preferably from about $1\times10^6$ units/person, three times per week to about $3\times10^6$ units/person, three times per week.

Due to the enhanced hepatitis virus antiviral effectiveness of these immunomodulators and immunostimulants in the presence of the N-substituted-glucamine compounds useful in the present invention, reduced amounts of other immunomodulators/immunostimulants can be employed in the methods and compositions disclosed herein. Such reduced amounts can be determined by routine monitoring of hepatitis virus in infected patients undergoing therapy. This can be carried out by, for example, monitoring hepatitis viral DNA in patients' serum by slot-blot, dot-blot, or PCR techniques, or by measurement of hepatitis surface or other antigens, such as the e antigen, in serum. Methods therefor are discussed in Hoofnagle et al., (1997) New Engl. Jour. Med. 336(5):347–356, and F. B. Hollinger in Fields Virology, Third Ed., Vol. 2 (1996), Bernard N. Fields et al., Eds., Chapter 86, "Hepatitis B Virus," pp. 2738–2807, Lippincott-Raven, Philadelphia, Pa., and the references cited therein.

Patients can be similarly monitored during combination therapy employing N-substituted-glucamine compounds and nucleoside and/or nucleotide antiviral agents to determine the lowest effective doses of each.

The doses described above can be administered to a patient in a single dose or in proportionate multiple sub-doses. In the latter case, dosage unit compositions can contain such amounts of submultiples thereof to make up the daily dose. Multiple doses per day can also increase the total daily dose should this be desired by the person prescribing the drug.

Pharmaceutical Compositions

The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Certain of the pharmaceutical compounds of this invention which are administered in accordance with the methods of the invention can serve as prodrugs to other compounds of this invention. Prodrugs are drugs that can be chemically converted in vivo or in vitro by biological systems into an active derivative or derivatives. Prodrugs are administered in essentially the same fashion as the other pharmaceutical compounds of the invention. Non-limiting examples are the esters of the N-substituted-1,5-dideoxy-1,5-imino-D-glucitol compounds of this invention.

Compounds of the combinations of this invention, for example N-(n-nonenyl)-glucamine and various nucleosides or nucleotides, may be acids or bases. As such, they may be used to form salts with one another. Nucleosides are purine or pyrimidine compounds lacking a phosphate ester. Compounds of Formulas II, III, IV; V, or VI herein without a phosphate ester but containing a carboxylic acid moiety could form a salt with an N-substituted-glucamine compound of the present invention. Nucleotides are purine or pyrimidine compounds that are mono-, di-, or triphosphate esters. These phosphate esters contain free —OH groups that are acidic, and that can form salts with inorganic bases or organic bases. Salt formation with organic bases depends on the pKa of the acid and base. Certain N-substituted-1,5-dideoxy-1,5-imino-D-glucitol compounds disclosed herein are basic and form pharmaceutically acceptable ammonium or quaternary ammonium salts. In the present case, useful salts can be formed not only with pharmaceutically acceptable acids, but also with biologically active acids such as the nucelosides and nucleotides disclosed herein. These salts can be prepared in the conventional manner for preparing salts, as is well known in the art. For example, one can treat the free base of an N-substituted-glucamine compound with a nucleotide analog of Formula II, III, IV, V, or VI to form a salt. This can be performed as a separate chemical reaction, or as part of the formulation process. The limiting reagent in the salt forming reaction is either the acid or base, as selected by the artisan to obtain a suitable biological result. The formulation can contain mixtures of different salts, acids, or free bases as desired. For example, the phosphoric acid form of (−)-2'-deoxy-3'-thiocytidine-5'-triphosphate will form a salt with the base form of N-(n-nonenyl)-glucamine or N-(n-nonenyl)-glucamine tetrabutyrate. This type of salt can then be provided to the patient in a pharmaceutically acceptable formulation, as a pure single salt, or as part of a mixture. These acids and bases can be independantly formulated and maintained in separate compartments in the same formulation if desired.

In some cases, the salts can also be used as an aid in the isolation, purification, or resolution of the compounds of this invention.

Treatment Regimen

The regimen for treating a patient suffering from a hepatitis virus infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized.

Administration of the drug combinations disclosed herein should generally be continued over a period of several weeks to several months or years until virus titers reach acceptable levels, indicating that infection has been controlled or eradicated. As noted above, patients undergoing treatment with the drug combinations disclosed herein can be routinely monitored by measuring hepatitis viral DNA in patients' serum by slot-blot, dot-blot, or PCR techniques, or by measurement of hepatitis antigens, such as hepatitis B surface antigen (HBsAg) and hepatitis B e antigen (HBeAg), in serum to determine the effectiveness of therapy. In chronic hepatitis B, for example, remissions are characterized by the disappearance of hepatitis B viral DNA, i.e., reduction to undetectable levels as measured by hybridization tests capable of detecting levels $10^5$ genomes per ml of serum, and HBeAg from serum despite the continued presence of HBsAg. These serologic events are followed by improvement in the biochemical and histologic features of the disease. The end point of successful treatment in most trials of antiviral therapy is the disappearance of HBeAg and viral DNA from serum. In patients in whom the e antigen disappears, remission is usually sustained, and results in an inactive HBsAg carrier state. Many patients eventually become HBsAg-negative (see Hoofnagle et al., (1997) New Engl. Jour. Med. 336(5):347–356 for a review).

Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis virus effectiveness are administered, and so that administration of such antiviral compounds in combination is continued only so long as is necessary to successfully treat the infection. The following non-limiting examples serve to illustrate various aspects of the present invention.

EXAMPLE 1

Preparation of 1,5-(Butylimino)-1,5-dideoxy-D-glucitol

A solution of 1,5-dideoxy-1,5-imino-D-glucitol (5.14 g, 0.0315 mole), butyraldehyde (3.35 ml, 0.0380 mole) and Pd black (1 g) in 200 ml methanol was hydrogenated (60 psi/29C/21 hrs.). After filtering the resulting mixture, the filtrate was concentrated in vacuo to an oil. The title compound was crystallized from acetone, and recrystallized from methanol/acetone, m.p. ca. 132C. The structure assignment was supported by NMR, infrared spectra and elemental analysis.

Analysis calcd. for $C_{10}H_{21}NO_4$: C, 54.78; H, 9.65; N, 6.39. Found: C, 54.46; H, 9.33; N, 6.46.

EXAMPLE 2

Preparation of 1,5-(Butylimino)-1,5-dideoxy-D-glucitol, Tetraacetate

Acetic anhydride (1.08 g, 0.0106 mole) was added to the title compound of Example 1 (0.50 g, 0.0023 mole) in 5 ml pyridine and stirred for 17 days at room temperature. The product was evaporated under nitrogen gas. The resulting title compound was purified by silica gel chromatography. Structure assignment was supported by NMR, infrared spectra and elemental analysis.

Analysis calcd. for $C_{18}H_{29}NO_8$: C, 55.80; H, 7.54; N, 3.62. Found: C, 55.42; H, 7.50; N, 3.72.

EXAMPLE 3

Anti-Hepatitis B Virus Activity of Various N-Substituted-1,5-Dideoxy-1,5-Imino-D-Glucitol Compounds in vitro The anti-hepatitis B virus activity and effect on cell viability of a number of different N-substituted-1,5-dideoxy-1,5-imino-D-glucitol compounds were assessed using an in vitro assay employing chronically hepatitis B virus secreting HepG2.2.15 cells. The method employed was essentially that described in Block et al. (1994) Proc. Natl. Acad. Sci. USA 91:2235–2239. The results are shown in Tables 2 and 3.

TABLE 2

Effect of N-Substituted-1,5-Dideoxy-1,5-Imino-D-Glucitol Compounds on Hepatitis B Virus Secretion and Viability of HepG2.2.15 Cells

| Compound and % Viable [Concentration][1] of Control[3] | +/− 1 S.D.[2,5] | Relative amount of HBV secreted As A % |
|---|---|---|
| Control | 90 +/− 7 (n = 4) | 100 |
| NBDNJ [200] | 94 +/− 6 (n = 10) | 37.0 +/− 13 (n = 15) |
| NBDNJ [1000] | 88 +/− 8 (n = 10) | 3.2 +/− 5 (n = 15) |

TABLE 2-continued

Effect of N-Substituted-1,5-Dideoxy-1,5-Imino-D-Glucitol Compounds on Hepatitis B Virus Secretion and Viability of HepG2.2.15 Cells

| Compound and % Viable [Concentration][1] of Control[3] | +/- 1 S.D.[2,5] | Relative amount of HBV secreted As A % |
|---|---|---|
| 1 [200] | 90 +/- 2 (n = 4) | 85.0 +/- 5 (n = 8) |
| 1 [1000] | 87 +/- 3 (n = 4) | 35.0 +/- 6 (n = 8) |
| 2 [200] | 90 +/- 6 (n = 4) | 107.0 +/- 12 (n = 3) |
| 2 [1000] | 89 +/- 4 (n = 4) | 38.0 +/- 15 (n = 3) |
| 3 [200] | n.d.[4] | 45.0 +/- 30 (n = 3) |
| 3 [1000] | n.d.[4] | 5.0 +/- 20 (n = 3) |
| 4 [200] | 93 +/- 1 (n = 4) | 60.0 (n = 2) |
| 4 [1000] | 91 +/- 3 (n = 4) | 34.0 (n = 2) |
| 5 [200] | 88 +/- 6 (n = 4) | 0.0 +/- 0 (n = 3) |
| 5 [1000] | 5 +/- 5 (n = 4) | 0.0 +/- 0 (n = 3) |
| 6 [200] | n.d. | 58.0 +/- 20 (n = 3) |
| 6 [1000] | n.d. | 20.0 +/- 15 (n = 3) |

[1]Chronically HBV secreting 2.2.15 cells (approximately 500,000 per well) were incubated in the presence of indicated compound for three days.
[2]After 3 days of culture in the absence or presence of compound, cells were removed by trypsin treatment, incubated with trypan blue, and visually examined for dye exclusion by microscopy. Values are the percentage, relative to the total number of cells examined, of cells excluding trypan blue (trypan blue exclusion was considered equivalent to viability).
[3]After 3 days of incubation in the absence or presence of compound, secreted virions were immunoprecipitated from the culture medium with monoclonal antibody specific for preS1 antigen (Meisel et al. (1995) Intervirology 37:330–339; Lu et al. (1995) Virology 213:660–665). Viral DNA present in the immunoprecipitates was detected by densitrometric quantification of the DNA fragment of the correct size resulting from a polymerase chain reaction. The amount of DNA amplified from control (cells receiving no compound) is assumed to be 100%.
NBDNJ: N-(n-butyl-)-1,5-dideoxy-1,5-imino-D-glucitol; N-butyl DNJ.
[4]Although trypan blue viability staining was not performed, cells appeared unremarkable (healthy) by gross microscopic examination.
[5]S.D.: standard deviation.
Compounds:
1: N-(3-phenylpropyl)-1,5-dideoxy-1,5-imino-D-glucitol
2: N-(n-butyl)-1,5-dideoxy-1,5-imino-D-glucitol, tetrabutyrate
3: N-(2-ethylbutyl)-1,5-dideoxy-1,5-imino-D-glucitol
4: N-(4,4,4-triflourobutyl)-1,5-dideoxy-1,5-imino-D-glucitol
5: N-(8,8,8-triflourooctyl)-1,5-dideoxy-1,5-imino-D-glucitol
6: N-(6,6,6-triflourohexyl)-1,5-dideoxy-1,5-imino-D-glucitol

TABLE 3

Effect of N-Substituted-1,5-Dideoxy-1,5-Imino-D-Glucitol Compounds on Hepatitis B Virus Secretion and Viability of HepG2.2.15 Cells

| Compound | [] for 90% HBV [] for a 50% secretion reduction in inhibition[1] MMT[2] |
|---|---|
| 1 | 0.5–1.0* |
|  | 100–200 |
| 2 | >200*s* |
|  | ND |
| 3 | 200* |
|  | >200 |
| 4 | 200* |
|  | >200 |
| 5 | 200* |
|  | >200 |
| 6 | >200** |
|  | >200 |
| 7 | >200** |
|  | >200 |
| 8 | >200** |
|  | >200 |
| 9 | >200** |
|  | >200 |
| 10 | –200 |
|  | 500 |

[1]in microgs per ml. and based upon duplicate PCR results.
[2]in microgs per ml.; MTT:
[3]Not determined.
*lowest concentration tested.
**there was no inhibition seen at the highest concentration used (200 microgs/ml).
Compounds:
1: N-(n-nonyl)-1,5-dideoxy-1,5-imino-D-glucitol
2: N-(n-butyl)-1,5-dideoxy-1,5-imino-D-glucitol, diacetate
3: 1,5-dideoxy-1,5-imino-D-glucitol, tetracetate
4: N,O-(1,6-carbonyl)-1,5-dideoxy-1,5-imino-D-glucitol
5: N-(n-butyl)-2,3-dimethoxy-1,5-dideoxy-1,5-imino-D-glucitol
6: N-(n-hexyl)-4,6-benzylidine-1,5-dideoxy-1,5-imino-D-glucitol
7: N-(n-butyl)-3-methoxy-1,5-dideoxy-1,5-imino-D-glucitol
8: N-(4,4,4-triflourobutyl)-2,3-dimethoxy-1,5-dideoxy-1,5-imino-D-glucitol, tetracetate
9: N,O-(1,6-methylenecarbonyl)-1,5-dideoxy-1,5-imino-D-glucitol
10: N-(8,8,8-triflourooctyl)-1,5-dideoxy-1,5-imino-D-glucitol
MMT: 3-(4,5-dimethylthiazol-2-yl)-2,5-diphenyltetrazolium bromide. The MTT-based colorimetric assay is a measurement of cell viability (Heo et al. (1990) Cancer Research 50:3681–3690).

EXAMPLE 4

Anti-Hepatitis B Virus Activity of (–)-2'-Deoxy-3'-thiocytidine-5'-triphosphate (3TC) Alone and in Combination with N-nonyl-DNJ The anti-hepatitis B virus effect of (–)-2'-deoxy-3'-thiocytidine-5'-triphosphate (3TC) alone and in combination with N-nonyl-DNJ was determined according to Korba ((1996) Antiviral Research 29(1):49–51), using the "combostat" strategy (Comstat Program, Combostat Corp., Duluth, Minn.). The combostat method involves serially diluting the IC-90 of each compound. The IC-90 of N-nonyl-DNJ has been determined to be between 4 and 10 g/ml (T. Block and G. Jacob, unpublished observation). The accepted IC-90 for 3TC in HepG 2.2.15 (2.2.15) cells is 300 nM to 500 nM (Doong et al. (1991) Proc. Natl. Acad. Sci. USA 88:8495–8499).

2.2.15 cells, described in Sells et al. (1987) Proc. Natl. Acad. Sci. USA 84:1005–1009, were maintained in RPMI 1640 medium (Gibco BRL, #31800–022) supplemented with 10% fetal bovine serum, 200 g/ml G418 (Gibco BRL 066–1811). Cells were seeded into 25 cm[2] flasks at 80% confluency. Five days later, flasks in triplicate received either no compound, serial dilutions of 3TC alone, or serial dilutions of 3TC plus N-nonyl-DNJ. At 2, 4, and 6 days after addition of compound (with medium replacement on those days), the amount of hepatitis B virus (HBV) DNA in the culture medium was determined by PCR analysis of polyethyleneglycol-sedimented particles. Thus, in these experiments, enveloped particles were not distinguished from nucleocapsids. PCR-amplified products were resolved by agarose gel electrophoresis (1.5% agarose), and the 538 nucleotide fragment was quantified by band scanning (HP Jet Imager). The amount of HBV recovered from untreated cells is assumed to be 100%. Data from the 6-day time point are presented in FIG. 1 as the average values from at least three separate flasks, and the standard error was never greater than 20%, with an average error of 12%.

For each of the three time point series tested, the combination of 3TC plus N-nonyl-DNJ was significantly more effective in inhibiting HBV secretion than either compound alone. Conclusions based upon PCR analysis alone make it difficult to assign precise IC-50 values. The extreme sensitivity and delicate nature of PCR, for example, may account for the inability to achieve greater than 90% inhibition of HBV by 3TC alone, even at 300 nM. Every experiment included controls to assure that PCR was performed in a range of concentrations of DNA in which the reaction yields results proportional to the amount of DNA in the sample. Resolution is approximately 3-fold, i.e., 3-fold differences in DNA concentrations can be detected. The inability to consistently detect less than 3-fold differences probably explains the failure of 3TC alone to achieve 90% inhibition. This suggests that a very high standard of inhibition must be met for the PCR to detect inhibition. Consequently, the trend, over three separate time points, is clear: the combined effect of 3TC plus N-nonyl-DNJ is greater than that of either compound alone, or the additive individual effects of each compound. These data suggest that the IC-50 of 3TC has been moved from about 60 nM to about 0.48 nM when 0.016 g/ml N-nonyl-DNJ is present.

EXAMPLE 5

Anti-Hepatitis B Virus Effect of N-nonyl-DNJ Alone in a Woodchuck Model

In order to evaluate the efficacy of N-nonyl-DNJ in combination with 3TC (or other nucleoside or nucleotide analogs) against Hepatitis B virus in a woodchuck animal model, an monotherapy experiment using N-nonyl-DNJ alone was first conducted. This was necessary to determine if N-nonyl-DNJ has any anti-HBV effect in the woodchuck and, if N-nonyl-DNJ has a beneficial effect, to design a combination study based on the dose-response relationship of this drug alone.

Therefore, five groups of four animals each (all groups had both sexes, all but the control had two of each sex) were assigned to 0, 12.5, 25, 50, and 100 mg/kg/day with BID oral dosing. These were lab-reared wild animals. All animals were infected with woodchuck hepatitis virus (WHV) as neonates, and had been tested positive on serological tests for WHV surface antigen. Blood samples were drawn one week prior to dosing (−1 week), immediately before dosing (0 weeks), weekly during dosing (1, 2, 3, and 4 weeks), and after the end of dosing (5, 6, 8, and 10 weeks).

There are two measures of drug efficacy: reduction in total HBV DNA (measured by quantitative PCR), and reduction in HBV DNA from capsids with intact surface glycoproteins, which is the active form of the virus (measured by an ELISA-like immune precipitation assay followed by quantitative PCR). Cell culture experiments with N-nonyl-DNJ demonstrated little or no effect of this compound on total HBV DNA, but a marked effect on the immune precipitated DNA (IPDNA). Not surprisingly, the IPDNA assay is quite variable; as a partial compensation for this, four assay runs were conducted, each containing samples from all animals, but different subsets of the study weeks.

To summarize the results, N-nonyl-DNJ had no effect on total HBV DNA measurements, which were essentially constant for all dose levels over the pre-dose and dosed portions of the study. On the other hand, IPDNA levels were not constant over the study period. The low dose animals tended to have increasing levels of IPDNA over the dosing period (weeks 0–4), while high dose animals tended to have decreasing levels of IPDNA over the same period. Fitting a straight line to each animal's weekly responses gave a significant difference in the slope of these lines due to either dose or plasma level of drug. The plasma levels of drug were also quite variable: animals with the lowest plasma levels in their dose group had lower plasma levels than the animals with the highest plasma levels from the next lower dose group. There were no differences between responses of males and females on any of the measures.

Plasma Levels

Figure 2:
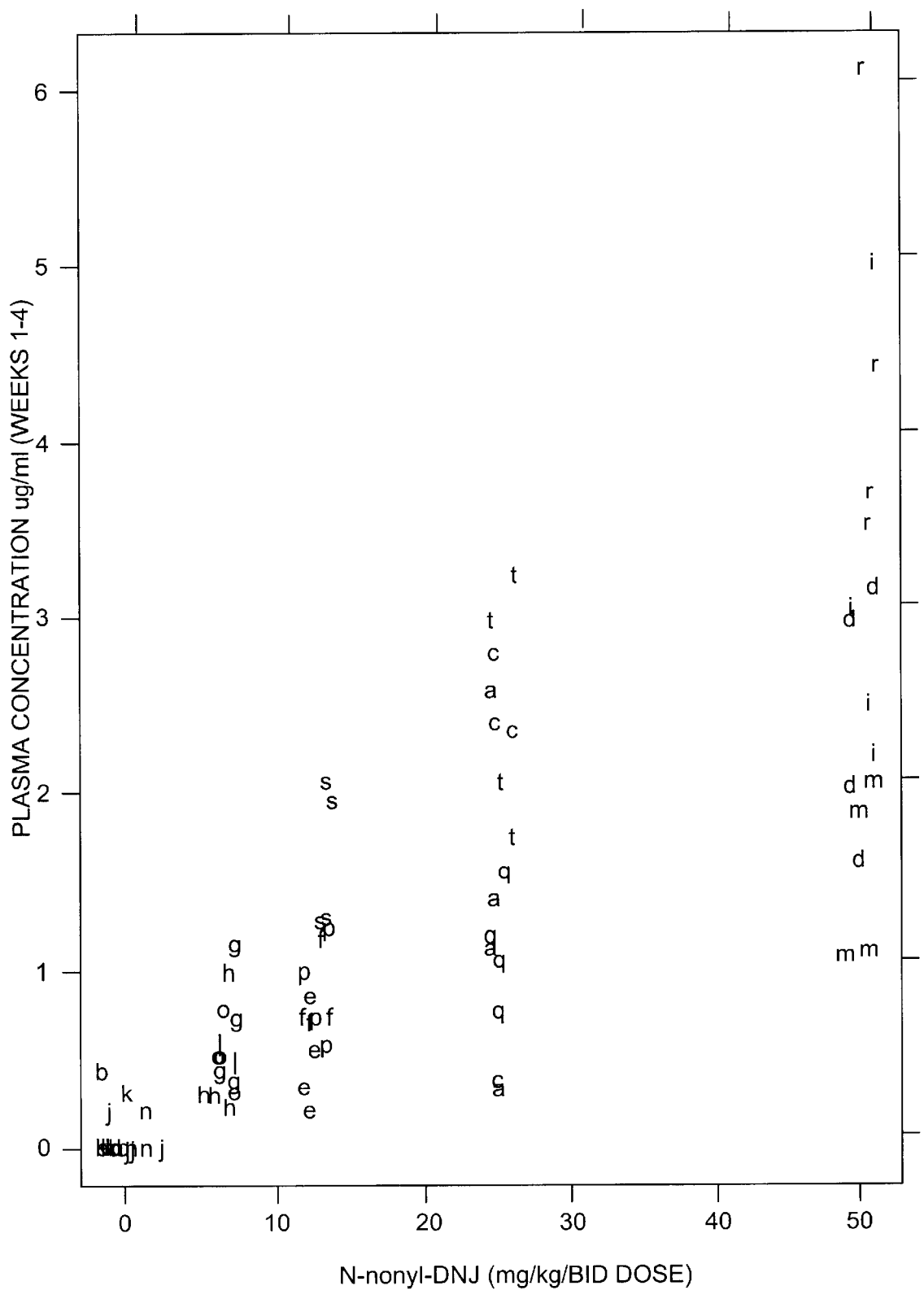
FIG. 2 shows the plasma concentration of N-nonyl-DNJ versus dose of N-nonyl-DNJ for each animal in Example 5, from samples taken during dosing. Animals are indicated by unique letters, and a small amount of random noise has been added to the dose value so that overlapping values can be distinguished.

There were no clear patterns in the changes in plasma levels of N-nonyl-DNJ which could be related to week of dosing or time since previous dose. Because the plasma levels within an animal seemed reasonably consistent during dosing, the median plasma level for each animal was used for subsequent modeling. The plasma levels for each week of the dosing period are plotted for each animal vs. dose (a small amount of random noise is added to the dose level so points which would lie on top of each other on the plot can be distinguished) (FIG. 2).

HBV DNA

The total HBV DNA levels were essentially constant over time within each animal (data not shown). There was a faint hint of a dose-response relationship with decreasing levels of virus with increasing levels of drug, except that three animals at the highest dose had very high virus levels. It is not possible to conclude that there is any relationship between dose of N-nonyl-DNJ and total HBV DNA. It is possible that there are two populations of animals, responders (such as animal r) and non-responders (animals i, m, and d), but more data would be required to permit a firm conclusion on this point.

Immune Precipitated HBV DNA

Substantial variation existed in the IPDNA assay, both between assay runs and within assay runs (data not shown). Even so, it was possible to observe and model a slope over weeks 0–4 which is generally increasing for low dose animals and decreasing for high dose animals. This change in slope was statistically significant ($p<0.005$).

Before models are fitted to the data, a log transform was applied because: 1) the variation in IPDNA increases with increasing IPDNA values; the log transformation gives values with a nearly constant variation, and 2) it is expected that drug effects will appear as a constant multiplier of the IPDNA level. Because there are zero values of IPDNA, a small value (about ½ of the smallest non-zero value) was added to all values before the log transform.

Two approaches were used to model the changes in slope to week with dose of N-nonyl-DNJ: a linear modeling approach and a nonlinear model. Both approaches assume that the (linear) rate of change of the Log(IPDNA) measure over the dosing period is the "right" measure to reflect the effect of the drug on the virus. Both approaches are fit in stages, and the first stage is common to both approaches. First, a simple straight line regression model is fit using weeks 0–4 to predict log(IPDNA_+_10) separately for each animal by run combination. In the second stage, the response variable is the slope fitted in the first stage.

For the linear approach, a model is fit with slope to week as the response where run is considered a block, dose has a significant effect (almost all of this effect is due to a slope to dose), and the relevant error for testing the effect of dose is the variation among animals treated alike (after the adjustment for the runs as blocks). This is similar to using the calibration data within each run to first adjust each run's data to a common virus DNA concentration; the difference is that here the data from the woodchucks are used for the run adjustment rather than only the calibration data.

For the nonlinear approach, a four parameter logistic model is fit with the slope to week as the response and the dose as the predictor. Again, run is considered a block, but because no run has all weeks, it is not possible to fully reflect the blocking in the nonlinear approach. Even so, the nonlinear model yields an EC50 of 7.88 mg/kg/BID dose. The average maximum slope observed was 2.71 additional Log (IPDNA g/mL)/week, or an increase of about 150%/week, the average minimum slope observed with N-nonyl-DNJ is 0.31 fewer Log(IPDNA g/mL)/week), or about a decrease of about 25%/week. The slopes, the fitted model, the parameter estimates from the model, and the approximate standard errors for these parameters are all shown in FIG. 3. The data indicate an approximate effective monotherapy dose of N-nonyl-DNJ in woodchucks of about 16 mg/kg/day. Whether in woodchucks or humans, the effective dose of both the N-alkyl-DNJ and nucleoside or nucleotide antiviral agent administered in combination therewith can be administered in two equal daily subdoses (i.e., B.I.D.).

Figure 3:
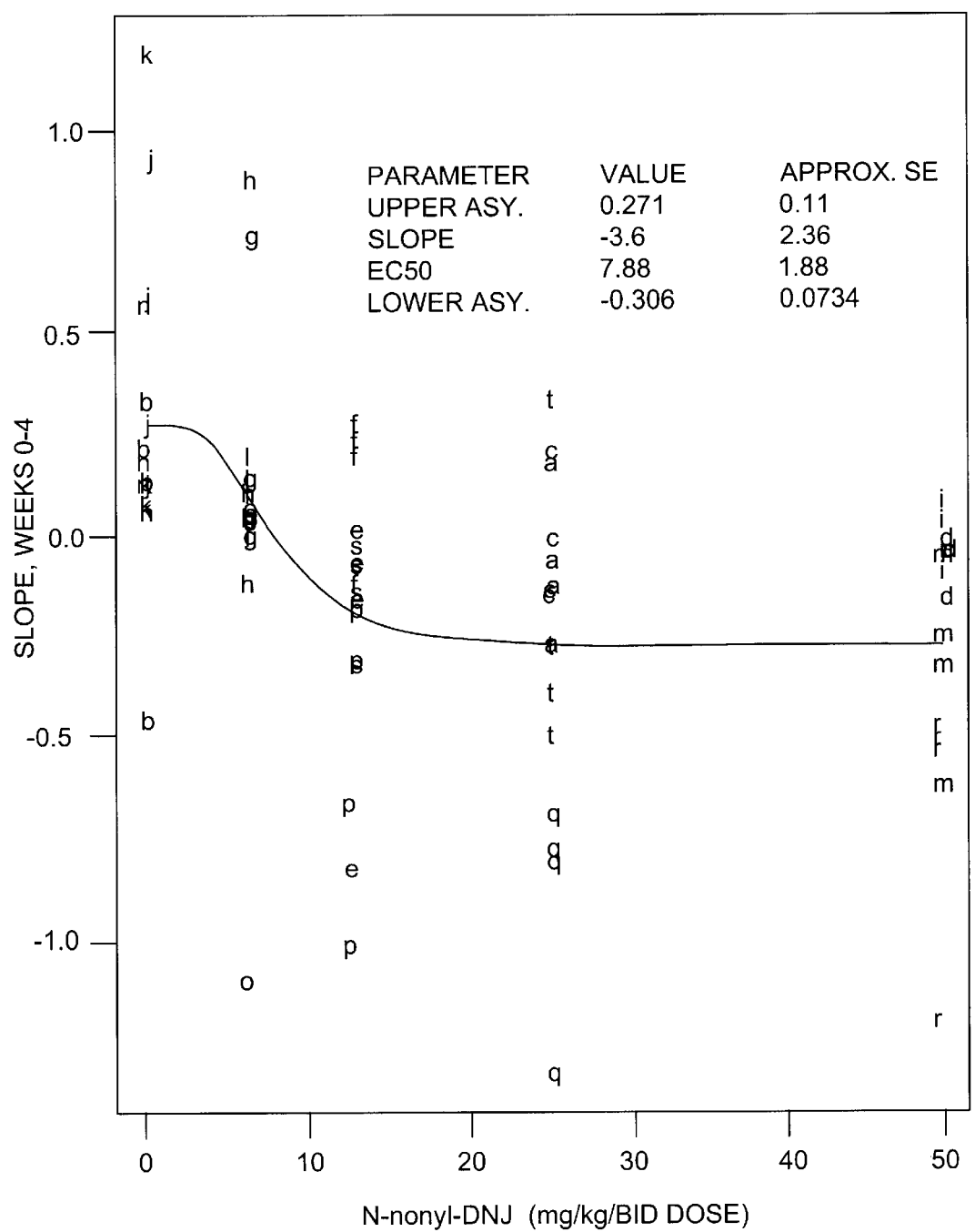
FIG. 3 shows the slope of Log(IPDNA+10) to week versus dose. A distinct letter is used for each animal. The fitted line is from a four parameter logistic model. The parameters of the fitted curve and their approximate standard errors are shown on the plot.

FIGS. 2 and 3 show letters to indicate animals. Table 4 shows two of the animal codes, the sex, and the dose.

TABLE 4

Animal Codes, Sex, and Dose

| Animal Number | Letter Code | Sex | Dose |
|---|---|---|---|
| F95343 | b | F | 0 |
| M96364 | n | M | 0 |
| F96304 | k | F | 0 |
| F96301 | j | F | 0 |
| M96285 | h | M | 6.25 |
| F96283 | g | F | 6.25 |
| F96391 | o | F | 6.25 |
| M96305 | l | M | 6.25 |
| F96271 | f | F | 12.5 |
| M96256 | e | M | 12.5 |
| M96404 | s | M | 12.5 |
| F96392 | p | F | 12.5 |
| F96163 | c | F | 25 |
| M96414 | t | M | 25 |
| F96393 | q | F | 25 |
| M95322 | a | M | 25 |

TABLE 4-continued

Animal Codes, Sex, and Dose

| Animal Number | Letter Code | Sex | Dose |
|---|---|---|---|
| M96286 | i | M | 50 |
| F96231 | d | F | 50 |
| F96402 | r | F | 50 |
| M96363 | m | M | 50 |

EXAMPLE 6

Antiviral Study to Test the Activity of N-nonyl-DNJ in Combination with 3TC in a Woodchuck Model of Hepatitis B Virus Infection The combined activity of N-nonyl-DNJ and the nucleoside analog 3TC can be assessed using the woodchuck model of hepatitis B virus infection. Twenty-eight woodchucks with persistent woodchuck hepatitis virus (WHV) infection can be utilized. Groups of woodchucks can be treated orally with 3TC alone (s.i.d.), with N-nonyl-DNJ alone (b.i.d.), or with combinations of the two drugs. The antiviral activity of the individual drugs and combinations can be assessed by measuring serum WHV DNA during treatment, and comparing the results of treated groups to placebo treated controls.

Twenty-eight woodchucks with established persistent WHV infection can be used, all of which were experimentally infected with WHV during the first week of life. All can be WHsAg positive at the time the study is initiated.

A total of eight experimental groups can be used. Woodchucks in each group can be stratified on the basis of gender, body weight, and age. 3TC can be administered orally as an aqueous suspension of Epivir (Glaxo-Wellcome) tablets one time per day. N-nonyl-DNJ can also be administered orally in aqueous solution, in two divided doses. Treatment with both drugs can be followed by the administration of 4 to 5 mls of semisynthetic liquid woodchuck diet to insure complete ingestion of the drugs.

The experimental groups can be as follows:

| Group ID | No. | 3TC (mg/kg/day) | N-nonyl-DNJ (mg/kg/day) |
|---|---|---|---|
| 1 | 4 | 0.0 | 0.0 |
| 2 | 3 | 3.0 | 0.0 |
| 3 | 3 | 9.0 | 0.0 |
| 4 | 3 | 0.0 | 4.0 |
| 5 | 3 | 0.0 | 12.0 |
| 6 | 4 | 1.5 | 2.0 |
| 7 | 4 | 4.5 | 6.0 |
| 8 | 4 | 9.0 | 12.0 |

Woodchucks can be anesthetized (50 mg/kg ketamine, 5 mg/kg zylazine), weighed, and blood samples obtained prior to initial treatment, at weekly intervals during the six week period of treatment, and at 1, 2, and 4 weeks following treatment. Serum can be harvested and divided into aliquots. One aliquot can be used for analysis of WHV DNA by dot blot hybridization and for WHsAg by ELISA. CBCs and clinical biochemical profiles can be obtained prior to treatment and at the end of treatment. A second aliquot can be maintained as an archive sample. Other aliquots of serum can be used for drug analysis and special WHV DNA analyses.

EXAMPLE 7

Preparation of N-[2-(4-Trifluoromethylphenyl)-ethyl]-glucamine

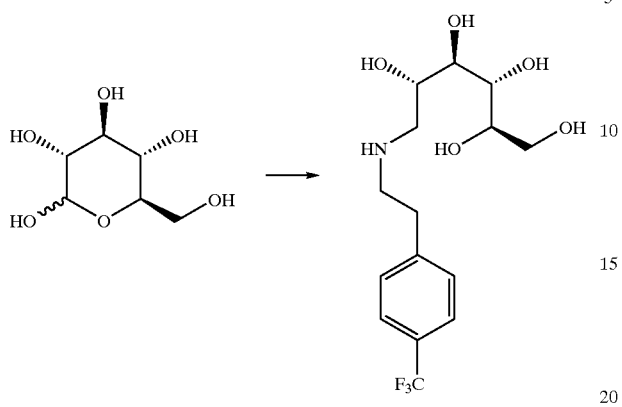

Ethanol (40 ml) is added to a pressure shaker bomb. One part of glucose is dissolved in the solvent followed by one part of 2-(4-trifluoromethylphenyl)-ethylamine. Hydrochloric acid is added to a pH of about 8 to 9. Wet 50% palladium on carbon 0.1 of a part of glucose is added and the mixture is agitated at about 40 degrees centigrade under about 3 atm of hydrogen gas until hydrogen uptake ceases. The hydrogen is vented and the catalyst is removed by filtration and the filtrated is washed with ethanol and the washings are added to the filtrate. The pH of the solution is lowered to about pH=4 with additional hydrochloric acid and the solvents removed on a rotary evaporator under reduced pressure.

EXAMPLE 8

Anti-Hepatitis B Virus Activity of N-Substituted-Glucamine Compounds in vitro The anti-hepatitis B virus activity and effect on cell viability of a number of different N-substituted-glucamine compounds is assessed using an in vitro assay employing chronically hepatitis B virus secreting HepG2.2.15 cells. The method employed is essentially that described in Block et al. (1994) Proc. Natl. Acad. Sci. USA 91:2235–2239. The compounds are of Formula I where R is: [2-(4-trifluoromethylphenyl)-ethyl], 4-(4-trifluoromethylphenyl)-butyl, 4-(4-trifluoromethylphenyl)-butane-1-carbonyl, 4-(4-trifluoromethyloxyphenyl)-butyl, 4-(4-trifluoromethyloxyphenyl)-butane-1-carbonyl, 2-cyclohexylethyl, 2-(4-thiapyran)-ethyl, 5-(morpholinyl-pentyl, 4-(4-pyridineoxy)-butyl, 3-(3-pyridyl)-propyl, 4-(4-trifluoromethylthiaphenyl)-butyl, 7-(trifluoromethylsulfonyl)-heptyl, 4-(4-trifluoromethylthia-phenyl)-butyl, 8-(trifluoromethylsulfonylamino)-octyl, 12,12,12-trifluoro-6,8-dioxa-dodecyl, 10,10,10-trifluoro-5-oxa-decyl, 12,12,12,11,11-pentafluoro-6-oxa-dodecyl, 9,9,9-trifluoro-2-oxa-nonyl, 5-(4-trifluoromethylphenyl)-4-oxa-butyl, 4-(4-trifluoromethylphenyl)-3-oxa-propyl, 4-(4-trifluoromethylphenyl)-3-oxa-propanoyl, 5-cyclohexyl-4-oxabutyl, 5-(4-trifluoromethoxyphenyl)-4-oxa-butyl and 5-(4-trifluoromethylthiaphenyl)-4-oxa-butyl.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A salt of an N-substituted glucamine compound and an antibacterial compound selected from the group consisting of (−)-2'-deoxy-3'-thiocytidine-5'-triphosphate (3TC), 1-(2'-deoxy-2'-fluoro-beta-D-arabinofuranosyl)-5-iodocytosine triphosphate (FIACTP), acyclovir triphosphate (ACVTP), E-5-(2-bromovinyl)-2'-deoxyuridine triphosphate, and 9-beta-D-arabinofuranosyl-9H-purine-6-amine-5'-monophosphate monohydrate (Ara-AMP), said glucamine compound corresponding to Formula I:

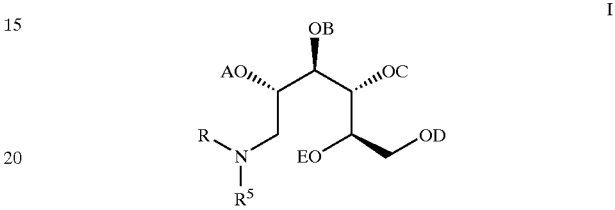

wherein:

R and $R^5$ are independently selected from the group consisting of substituted alkenylcarbonyl, alkynylcarbonyl, arylalkylcarbonyl, aryloxyalkylcarbonyl, haloalkylcarbonyl, hydroxyalkylcarbonyl, haloalkyloxyalkylcarbonyl, cycloalkyloxyalkylcarbonyl, alkoxyalkylcarbonyl, cycloalkylalkylcarbonyl, alkoxycarbonyl, alkylcarbonyl, aryloxyalkoxyalkylcarbonyl, alkylcarbonyloxyalkylcarbonyl, arylcarbonyloxyalkylcarbonyl, alkylcarbonylaminoalkylcarbonyl, arylcarbonylaminoalkylcarbonyl, alkoxycarbonylaminoalkylcarbonyl, aminocarbonylaminoalkylcarbonyl, aminothiocarbonyl, aminoalkylcarbonyl, arylalkenylcarbonyl, carboxyalkylcarbonyl, alkoxycarbonylalkylcarbonyl, aminocarbonylalkylcarbonyl, aminothiocarbonylalkylcarbonyl, aminosulfonealkylcarbonyl, arylalkynylcarbonyl, heterocycloalkylcarbonyl, heteroarylthiaalkylcarbonyl, heterocyclooxyalkylcarbonyl, heterocyclothiaalkylcarbonyl, arylthiaalkylcarbonyl, monohaloalkylcarbonyl, cycloalkylalkyloxyalkylcarbonyl, cycloalkylcarbonyl, cycloalkenylcarbonyl, arylcarbonyl, cycloalkenylalkylcarbonyl, cycloalkenylalkenylcarbonyl, cycloalkenylalkynylcarbonyl, bicycloalkenylalkylcarbonyl, tricycloalkenylalkylcarbonyl, tetracycloalkenylalkylcarbonyl, bicycloalkenoxyalkylcarbonyl, tricycloalkenoxyalkylcarbonyl, tetracycloalkenyloxyalkylcarbonyl, cycloalkylalkenylcarbonyl, cycloalkylalkynylcarbonyl, aralkylcarbonyl, aralkoxyalkylcarbonyl, aralkoxyalkenylcarbonyl, aralkoxyalkynylcarbonyl, aralkenoxyalkylcarbonyl, aralkenoxyalkenylcarbonyl, heterocycloalkenylcarbonyl, heteroarylalkenylcarbonyl, heteroarylalkynylcarbonyl, aryloxyalkenylcarbonyl, aryloxyalkynylcarbonyl, dihydroxyalkylcarbonyl, hydroxyalkenylcarbonyl, dihydroxyalkenylcarbonyl, hydroxyalkynylcarbonyl, haloalkoxyalkenylcarbonyl, haloalkoxyalkynylcarbonyl, or hydroxysulfonealkylcarbonyl, wherein R and R⁵ are independently substituted by one or more substituents selected from the group consisting of amino, substituted amino, disubstituted amino, heterocyclo containing at least one nitrogen, or heteroaryl containing at least one basic nitrogen, R and R⁵ are independently selected from the group consisting of substituted alkenylcarbonyl, alkynylcarbonyl, arylalkylcarbonyl, aryloxyalkylcarbonyl, haloalkylcarbonyl, hydroxyalkylcarbonyl, haloalkyloxyalkylcarbonyl, cycloalkyloxyalkylcarbonyl, alkoxyalkylcarbonyl, cycloalkylalkylcarbonyl, alkoxycarbonyl, alkylcarbonyl, aryloxyalkoxyalkylcarbonyl, alkylcarbonyloxyalkylcarbonyl, arylcarbonyloxyalkylcarbonyl, alkylcarbonylaminoalkylcarbonyl, arylcarbonylaminoalkylcarbonyl, alkoxycarbonylaminoalkylcarbonyl, aminocarbonylaminoalkylcarbonyl, aminothiocarbonyl, aminoalkylcarbonyl, arylalkenylcarbonyl, carboxyalkylcarbonyl, alkoxycarbonylalkylcarbonyl, aminocarbonylalkylcarbonyl, aminothiocarbonylalkylcarbonyl, aminosulfonealkylcarbonyl, arylalkynylcarbonyl, heterocycloalkylcarbonyl, heteroarylthiaalkylcarbonyl, heterocyclooxyalkylcarbonyl, heterocyclothiaalkylcarbonyl, arylthiaalkylcarbonyl, monohaloalkylcarbonyl, cycloalkylalkyloxyalkylcarbonyl, cycloalkylcarbonyl, cycloalkenylcarbonyl, arylcarbonyl, cycloalkenylalkylcarbonyl, cycloalkenylalkenylcarbonyl, cycloalkenylalkynylcarbonyl, bicycloalkenylalkylcarbonyl, tricycloalkenylalkylcarbonyl, tetracycloalkenylalkylcarbonyl, bicycloalkenoxyalkylcarbonyl, tricycloalkenoxyalkylcarbonyl, tetracycloalkenyloxyalkylcarbonyl, cycloalkylalkenylcarbonyl, cycloalkylalkynylcarbonyl, aralkylcarbonyl, aralkoxyalkylcarbonyl, aralkoxyalkenylcarbonyl, aralkoxyalkynylcarbonyl, aralkenoxyalkylcarbonyl, aralkenoxyalkenylcarbonyl, heterocycloalkenylcarbonyl, heteroarylalkenylcarbonyl, heteroarylalkynylcarbonyl, aryloxyalkenylcarbonyl, aryloxyalkynylcarbonyl, dihydroxyalkylcarbonyl, hydroxyalkenylcarbonyl, dihydroxyalkenylcarbonyl, hydroxyalkynylcarbonyl, haloalkoxyalkenylcarbonyl, haloalkoxyalkynylcarbonyl, or hydroxysulfonealkylcarbonyl, wherein R and R⁵ are independently substituted by one or more substituents selected from the group consisting of amino, substituted amino, disubstituted amino, heterocyclo containing at least one nitrogen, or heteroaryl containing at least one basic nitrogen, A, B, C, D and E are independently hydrido, lower alkyl or acyl;

A and B taken together with the atoms to which they are attached may form a five or six membered heterocyclic ring;

B and C taken together with the atoms to which they are attached may form a five or six membered heterocyclic ring;

C and D taken together with the atoms to which they are attached may form a five or six membered heterocyclic ring;

C and E taken together with the atoms to which they are attached may form a five or six membered heterocyclic ring;

and D and E taken together with the atoms to which they are attached may form a five or six membered heterocyclic ring.

2. A salt according to claim 1 wherein the antiviral compound is (−)-2'-deoxy-3'-thiocytidine-5'-triphosphate (3TC).

3. A salt according to claim 2 wherein the antiviral compound is (−)-2'-deoxy-3'-thiocytidine-5'-triphosphate (3TC).

4. A salt according to claim 3 wherein A, B, C and D are acyl.

5. A salt according to claim 4 wherein A, B, C and D are alkanoyl.

6. A salt according to claim 5 wherein A, B, C and D are butanoyl.

7. A salt of an N-substituted glucamine compound and an antibacterial compound selected from the group consisting of (−)-2'-deoxy-3'-thiocytidine-5'-triphosphate (3TC), 1-(2'-deoxy-2'-fluoro-beta-D-arabinofuranosyl)-5-iodocytosine triphosphate (FIACTP), acyclovir triphosphate (ACVTP), E-5-(2-bromovinyl)-2'-deoxyuridine triphosphate, and 9-beta-D-arabinofuranosyl-9H-purine-6-amine-5'-monophosphate monohydrate (Ara-AMP), said glucamine compound corresponding to Formula I:

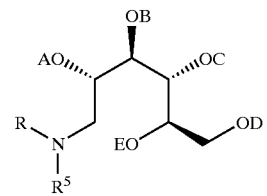

wherein:

R and R⁵ are independently selected from the group consisting of H, aryloxyalkoxyalkyl, alkylcarbonyloxyalkyl, alkyl, arylcarbonyloxyalkyl, aminoalkyl, alkylcarbonylaminoalkyl, arylcarbonylaminoalkyl, alkoxycarbonylaminoalkyl, aminocarbonylaminoalkyl, aminothiocarbonylaminoalkyl, alkenyl, alkynyl, alkoxyalkyl, hydroxyalkyl, arylalkyl, arylalkenyl, carboxyalkyl, alkoxycarbonylalkyl, aminocarbonylalkyl, aminothiocarbonylalkyl, aminosulfonealkyl, arylalkynyl, heterocycloalkyl, heteroarylalkyl, heteroaryloxyalkyl, heteroarylthiaalkyl, heterocyclooxyalkyl, heterocyclothiaalkyl, aryloxyalkyl, arylthiaalkyl, haloalkyl, haloalkyloxyalkyl, carbonyl, cycloalkyloxyalkyl, cycloalkylalkyloxyalkyl, perhaloalkylaralkyl, cycloalkyl, cycloalkylalkyl, cycloalkenyl, aryl, cycloalkenylalkyl, cycloalkenylalkenyl, cycloalkenylalkynyl, bicycloalkenylalkyl, tricycloalkenylalkyl, tetracycloalkenylalkyl, bicycloalkenoxyalkyl, tricycloalkenoxyalkyl, tetracycloalkenyloxyalkyl, cycloalkylalkenyl, cycloalkylalkynyl, aralkyl, aralkoxyalkyl, aralkoxyalkenyl, aralkoxyalkynyl, aralkenoxyalkyl, aralkenoxyalkenyl, heterocycloalkenyl, heteroarylalkenyl, heteroarylalkynyl, aryloxyalkenyl, aryloxyalkynyl, dihydroxyalkyl, hydroxyalkenyl, dihydroxyalkenyl, hydroxyalkynyl, haloalkoxyalkenyl, haloalkoxyalkynyl, hydroxysulfonealkyl, $R^7$ or $R^8$, wherein $R^7 = R^1X^1(R^2X^2)_m(R^3X^3)_n(R^4X^4)_pR^{13}$;
$R^8 = R^9X^9(R^{10}X^{10})_q(R^{11}X^{11})_r(R^{12}X^{12})_sR^{13}$ $R^1$ and $R^9$ are independently selected from the group consisting of alkyl, aryl, alkenyl, alkynyl, hydrogen or haloalkyl;

$R^2$, $R^3$, $R^4$, $R^{10}$, $R^{11}$, $R^{12}$ and $R^{13}$ are independently selected from the group consisting of alkylene, alkenylene, alkynylene or haloalkylene;

$X^1$, $X^2$, $X^3$, $X^4$, $X^9$, $X^{10}$, $X^{11}$ and $X^{12}$ are independently oxygen, sulfur, sulfoxide or sulfone;

m, n, p, q, r and s are independently 0, 1, 2 or 3;

$$m+n+p \leq 3$$

$$q+r+s \leq 3$$

A, B, C, D and E are independently hydrido, lower alkyl or acyl;

A and B taken together with the atoms to which they are attached may form a five or six membered heterocyclic ring;

B and C taken together with the atoms to which they are attached may form a five or six membered heterocyclic ring;

C and D taken together with the atoms to which they are attached may form a five or six membered heterocyclic ring;

C and E taken together with the atoms to which they are attached may form a five or six membered heterocyclic ring;

and D and E taken together with the atoms to which they are attached may form a five or six membered heterocyclic ring.

8. A salt according to claim 7 wherein the antiviral compound is (−)-2'-deoxy-3'-thiocytidine-5'-triphosphate (3TC).

9. A salt according to claim 8 wherein R is hydrogen and $R^5$ is alkenyl.

10. A salt according to claim 9 wherein $R^5$ is n-nonenyl.

11. A salt according to claim 8 wherein A, B, C and D are acyl.

12. A salt according to claim 11 wherein A, B, C and D are alkanoyl.

13. A salt according to claim 12 wherein A, B, C and D are butanoyl.

* * * * *